(12) United States Patent
Nowakowski et al.

(10) Patent No.: US 12,128,414 B2
(45) Date of Patent: Oct. 29, 2024

(54) AUTOMATED METHOD FOR PERFORMING AN ASSAY

(71) Applicant: Mesa Biotech, Inc., San Diego, CA (US)

(72) Inventors: Mark Nowakowski, San Diego, CA (US); Michael Wang, San Diego, CA (US); Robert B Cary, Santa Fe, NM (US); Hong Cai, Los Alamos, NM (US); Conrad Lindberg, Fallbrook, CA (US); Martin Bouliane, Carlsbad, CA (US); Donald J Thomas, Vista, CA (US)

(73) Assignee: MESA BIOTECH LLC, Carlsbad, CA (US)

( * ) Notice: Subject to any disclaimer, the term of this patent is extended or adjusted under 35 U.S.C. 154(b) by 100 days.

(21) Appl. No.: 17/929,369

(22) Filed: Sep. 2, 2022

(65) Prior Publication Data
US 2024/0076724 A1 Mar. 7, 2024

Related U.S. Application Data

(63) Continuation of application No. 15/137,983, filed on Apr. 25, 2016, now abandoned.
(Continued)

(51) Int. Cl.
*B01L 7/00* (2006.01)
*B01L 3/00* (2006.01)
(Continued)

(52) U.S. Cl.
CPC ........... *B01L 7/52* (2013.01); *B01L 3/502723* (2013.01); *B01L 3/50273* (2013.01);
(Continued)

(58) Field of Classification Search
None
See application file for complete search history.

(56) References Cited

U.S. PATENT DOCUMENTS

| 3,667,607 A | 6/1972 | Brandt |
| 4,235,601 A | 11/1980 | Deutsch et al. |

(Continued)

FOREIGN PATENT DOCUMENTS

| CN | 1254844 A | 5/2000 |
| CN | 1680574 A | 10/2005 |

(Continued)

OTHER PUBLICATIONS

Selvaraju, S.B. et al. Evaluation of Three Influenza A and B Real-Time Reverse Transcription-PCR Assays and a New 2009 H1N1 Assay for Detection of Influenza Viruses, Journal of Clinical Microbiology, Nov. 2010, p. 3870-3875 (Year: 2010).*

(Continued)

*Primary Examiner* — Xiaoyun R Xu

(57) ABSTRACT

An automated method for performing an assay of the present disclosure can be performed in a microfluidic device that is a lateral flow device having numerous features to ensure correct operation of the device under gravity, such as vent pockets for enabling the flow of sample fluid from one chamber to the next when the vent pocket is unsealed. Each chamber can have a reagent recess proximal to an inlet end of the chamber. A reagent pellet formed in a reagent recess can be effectively mixed with a sample as the sample flows into the chamber. A flexible circuit with patterned metallic electrical components disposed on a heat stable material can be in direct contact with fluid in the chambers and has resistive heating elements aligned with, for example, a chamber for performing an amplification reaction. A lateral flow detection chamber can include a capillary pool proximal to a sample receiving end of a lateral flow strip, (Continued)

providing effective mixing and dispersion of a sample with detection particles, as well as enhancing, uniformity of particle migration on the detection strip. The microfluidic device can be configured to be hermetically sealed, thereby preventing contamination of a testing environment.

19 Claims, 67 Drawing Sheets

Related U.S. Application Data

(60) Provisional application No. 62/322,738, filed on Apr. 14, 2016, provisional application No. 62/152,724, filed on Apr. 24, 2015.

(51) Int. Cl.
  *C12Q 1/04* (2006.01)
  *C12Q 1/6816* (2018.01)
  *C12Q 1/6844* (2018.01)

(52) U.S. Cl.
  CPC ... *B01L 3/502738* (2013.01); *B01L 3/502746* (2013.01); *B01L 3/502761* (2013.01); *B01L 3/502769* (2013.01); *C12Q 1/04* (2013.01); *C12Q 1/6816* (2013.01); *C12Q 1/6844* (2013.01); *B01L 3/502715* (2013.01); *B01L 2200/0621* (2013.01); *B01L 2200/0689* (2013.01); *B01L 2200/147* (2013.01); *B01L 2200/16* (2013.01); *B01L 2300/048* (2013.01); *B01L 2300/0822* (2013.01); *B01L 2300/0883* (2013.01); *B01L 2300/123* (2013.01); *B01L 2300/1827* (2013.01); *B01L 2400/0406* (2013.01); *B01L 2400/0445* (2013.01); *B01L 2400/0457* (2013.01); *B01L 2400/0638* (2013.01); *B01L 2400/0677* (2013.01); *B01L 2400/0694* (2013.01); *C12Q 2531/113* (2013.01); *C12Q 2560/00* (2013.01)

(56) References Cited

U.S. PATENT DOCUMENTS

| | | | |
|---|---|---|---|
| 4,663,277 A | 5/1987 | Wang |
| 4,683,195 A | 7/1987 | Mullis et al. |
| 4,683,202 A | 7/1987 | Mullis |
| 4,800,159 A | 1/1989 | Mullis et al. |
| 4,960,691 A | 10/1990 | Gordon et al. |
| 5,077,017 A | 12/1991 | Gorin et al. |
| 5,225,163 A | 7/1993 | Andrews |
| 5,354,538 A | 10/1994 | Bunce et al. |
| 5,514,785 A | 5/1996 | Van et al. |
| 5,516,488 A | 5/1996 | Bunce et al. |
| 5,516,664 A | 5/1996 | Hyman |
| 5,578,467 A | 11/1996 | Schuster et al. |
| 5,618,494 A | 4/1997 | Bunce et al. |
| 5,716,819 A | 2/1998 | Chatterjee |
| 5,736,188 A | 4/1998 | Alcock et al. |
| 5,741,647 A | 4/1998 | Tam |
| 5,824,478 A | 10/1998 | Mueller |
| 5,922,617 A | 7/1999 | Wang et al. |
| 6,007,999 A | 12/1999 | Clark |
| 6,037,127 A | 3/2000 | Ebersole et al. |
| 6,083,502 A | 7/2000 | Pastan et al. |
| 6,130,098 A | 10/2000 | Handique et al. |
| 6,146,589 A | 11/2000 | Chandler |
| 6,190,612 B1 | 2/2001 | Berger et al. |
| 6,214,587 B1 | 4/2001 | Dattagupta et al. |
| 6,261,779 B1 | 7/2001 | Barbera-Guillem et al. |
| 6,300,069 B1 | 10/2001 | Missel et al. |
| 6,335,205 B1 | 1/2002 | Bausback |
| 6,468,749 B1 | 10/2002 | Ulanovsky et al. |
| 6,471,916 B1 | 10/2002 | Noblett |
| 6,555,349 B1 | 4/2003 | O'Donnell |
| 6,743,399 B1 | 6/2004 | Weigl et al. |
| 7,094,536 B2 | 8/2006 | Kurn |
| 7,159,618 B2 | 1/2007 | Broyer et al. |
| 7,186,508 B2 | 3/2007 | Lee et al. |
| 7,195,872 B2 | 3/2007 | Agrawal et al. |
| 7,273,590 B2 | 9/2007 | Yao et al. |
| 8,173,078 B2 | 5/2012 | Yao et al. |
| 8,980,561 B1 | 3/2015 | Cai et al. |
| 9,207,236 B2 | 12/2015 | Cary |
| 9,354,199 B2 | 5/2016 | Selden et al. |
| 9,428,781 B2 | 8/2016 | Cai et al. |
| 9,731,297 B2 | 8/2017 | Glezer et al. |
| 9,944,922 B2 | 4/2018 | Cary |
| 10,316,358 B2 | 6/2019 | Cai et al. |
| 10,458,978 B2 | 10/2019 | Cary |
| 10,519,492 B2 | 12/2019 | Dejohn et al. |
| 2001/0019825 A1 | 9/2001 | Lee et al. |
| 2002/0028475 A1 | 3/2002 | Ligler et al. |
| 2002/0058252 A1 | 5/2002 | Ananiev |
| 2002/0076825 A1 | 6/2002 | Cheng et al. |
| 2002/0127574 A1 | 9/2002 | Mirkin et al. |
| 2002/0172969 A1 | 11/2002 | Burns et al. |
| 2002/0177135 A1 | 11/2002 | Doung et al. |
| 2002/0179445 A1 | 12/2002 | Alajoki et al. |
| 2002/0192839 A1 | 12/2002 | Mink et al. |
| 2003/0003514 A1 | 1/2003 | Kovalenko |
| 2003/0008308 A1 | 1/2003 | Enzelberger et al. |
| 2003/0044862 A1 | 3/2003 | Giaccia et al. |
| 2003/0054176 A1 | 3/2003 | Pantano et al. |
| 2003/0064364 A1 | 4/2003 | Lockhart et al. |
| 2003/0100128 A1 | 5/2003 | Kenjyou et al. |
| 2003/0170686 A1 | 9/2003 | Hoet et al. |
| 2003/0190608 A1 | 10/2003 | Blackburn |
| 2004/0029177 A1 | 2/2004 | Nadaoka et al. |
| 2004/0053256 A1 | 3/2004 | Lee et al. |
| 2004/0058378 A1 | 3/2004 | Kong et al. |
| 2004/0086897 A1 | 5/2004 | Mirkin et al. |
| 2004/0110167 A1 | 6/2004 | Gerdes et al. |
| 2004/0152122 A1 | 8/2004 | Hwang et al. |
| 2004/0209309 A1 | 10/2004 | Muldoon et al. |
| 2005/0014192 A1 | 1/2005 | Kurn |
| 2005/0032729 A1 | 2/2005 | Shyamala |
| 2005/0032730 A1 | 2/2005 | Von et al. |
| 2005/0042627 A1 | 2/2005 | Chakrabarti et al. |
| 2005/0047972 A1 | 3/2005 | Lauks et al. |
| 2005/0079492 A1 | 4/2005 | Burgess et al. |
| 2005/0112780 A1 | 5/2005 | Song |
| 2005/0136443 A1 | 6/2005 | Shigemori |
| 2005/0221281 A1 | 10/2005 | Ho |
| 2005/0227275 A1 | 10/2005 | Jung et al. |
| 2005/0243321 A1 | 11/2005 | Cohen et al. |
| 2005/0250141 A1 | 11/2005 | Lambert et al. |
| 2006/0024813 A1 | 2/2006 | Warthoe |
| 2006/0040408 A1 | 2/2006 | Jones et al. |
| 2006/0041058 A1 | 2/2006 | Yin et al. |
| 2006/0127886 A1 | 6/2006 | Kaylor et al. |
| 2006/0154286 A1 | 7/2006 | Kong et al. |
| 2006/0160078 A1 | 7/2006 | Cardy et al. |
| 2006/0177873 A1 | 8/2006 | Dowd et al. |
| 2006/0239859 A1 | 10/2006 | Ohman et al. |
| 2006/0246601 A1 | 11/2006 | Song et al. |
| 2006/0286570 A1 | 12/2006 | Rowlen et al. |
| 2007/0015166 A1 | 1/2007 | Nilsen |
| 2007/0020768 A1 | 1/2007 | Rundstrom et al. |
| 2007/0039835 A1 | 2/2007 | Rossier et al. |
| 2007/0231798 A1 | 10/2007 | Collins |
| 2008/0124720 A1 | 5/2008 | Sowerby et al. |
| 2008/0145835 A1 | 6/2008 | Alajem et al. |
| 2008/0207892 A1 | 8/2008 | Iwaki et al. |
| 2008/0280285 A1 | 11/2008 | Chen et al. |
| 2009/0047673 A1 | 2/2009 | Cary |
| 2009/0047691 A1 | 2/2009 | Huwig et al. |
| 2009/0053106 A1 | 2/2009 | Wu et al. |
| 2009/0130719 A1 | 5/2009 | Handique |
| 2009/0181411 A1 | 7/2009 | Battrell et al. |
| 2009/0186357 A1 | 7/2009 | Mauk et al. |

(56) References Cited

U.S. PATENT DOCUMENTS

| | | |
|---|---|---|
| 2009/0246782 A1 | 10/2009 | Kelso et al. |
| 2010/0015695 A1 | 1/2010 | Cho et al. |
| 2010/0119416 A1 | 5/2010 | Tajima |
| 2010/0173310 A1 | 7/2010 | Bousse et al. |
| 2010/0203532 A1 | 8/2010 | Makrigiorgos |
| 2010/0248273 A1 | 9/2010 | Campbell et al. |
| 2010/0276005 A1 | 11/2010 | Allain et al. |
| 2011/0039261 A1 | 2/2011 | Hillebrand et al. |
| 2011/0117540 A1 | 5/2011 | Cary |
| 2011/0160090 A1 | 6/2011 | Cary |
| 2012/0040445 A1 | 2/2012 | Bouma et al. |
| 2014/0045191 A1 | 2/2014 | Dejohn et al. |
| 2014/0141484 A1 | 5/2014 | Campbell et al. |
| 2014/0170707 A1 | 6/2014 | Hwang et al. |
| 2015/0184255 A1 | 7/2015 | Cai et al. |
| 2016/0083716 A1 | 3/2016 | Cary |
| 2016/0222442 A1 | 8/2016 | Cary |
| 2016/0310948 A1 | 10/2016 | Nowakowski et al. |
| 2016/0362725 A1 | 12/2016 | Cai et al. |
| 2017/0160271 A1 | 6/2017 | Cary |
| 2017/0233794 A1 | 8/2017 | Cai et al. |
| 2018/0304260 A1 | 10/2018 | Thomas et al. |
| 2019/0330681 A1 | 10/2019 | Cai et al. |
| 2020/0216876 A1 | 7/2020 | Dejohn et al. |
| 2020/0292532 A1 | 9/2020 | Cary |

FOREIGN PATENT DOCUMENTS

| | | |
|---|---|---|
| CN | 1954214 A | 4/2007 |
| CN | 101400993 A | 4/2009 |
| CN | 101680013 A | 3/2010 |
| EP | 0805215 A2 | 11/1997 |
| EP | 1972938 A1 | 9/2008 |
| GB | 2261284 A | 5/1993 |
| JP | 05-240872 A | 9/1993 |
| JP | 2001-518614 A | 10/2001 |
| JP | 2005508495 A | 3/2005 |
| JP | 2005-185972 A | 7/2005 |
| JP | 2005-532827 A | 11/2005 |
| JP | 2006-520190 A | 9/2006 |
| JP | 2007-503958 A | 3/2007 |
| JP | 2008-521432 A | 6/2008 |
| JP | 2009-100761 A | 5/2009 |
| JP | 2009524063 A | 6/2009 |
| JP | 2010148494 A | 7/2010 |
| JP | 2014-515611 A | 7/2014 |
| KR | 20000036176 A | 6/2000 |
| KR | 20130099648 A | 9/2013 |
| TW | 200632318 A | 9/2006 |
| WO | 94/23055 A1 | 10/1994 |
| WO | 97/03207 A1 | 1/1997 |
| WO | 00/29112 A1 | 5/2000 |
| WO | 2004/007078 A1 | 1/2004 |
| WO | 2004/090555 A1 | 10/2004 |
| WO | 2004/092342 A2 | 10/2004 |
| WO | 2005/045408 A1 | 5/2005 |
| WO | 2005/098439 A2 | 10/2005 |
| WO | 2006/098804 A2 | 9/2006 |
| WO | 2006/122311 A2 | 11/2006 |
| WO | 2007/030505 A1 | 3/2007 |
| WO | 2007/059167 A2 | 5/2007 |
| WO | 2007/083388 A1 | 7/2007 |
| WO | 2008/105814 A2 | 9/2008 |
| WO | 2009/103843 A2 | 8/2009 |
| WO | 2009/137055 A1 | 11/2009 |
| WO | 2009/137059 A1 | 11/2009 |
| WO | 2010/037012 A2 | 4/2010 |
| WO | 2010/105074 A1 | 9/2010 |
| WO | 2011/087813 A2 | 7/2011 |
| WO | 2012/083189 A3 | 8/2012 |
| WO | 2012/145725 A2 | 10/2012 |
| WO | 2012/145730 A2 | 10/2012 |
| WO | 2015/019626 A1 | 2/2015 |

OTHER PUBLICATIONS

Lee, C-Y., et al. Integrated microfluidic systems for cell lysis, mixing/pumping and DNA amplification, J. Micromech. Microeng. 15 (2005) 1215-1223 (Year: 2005).*

Yang, et al., "PCR-based diagnositcs for infectious diseases: uses, limitations, and future applications in acute-care settings", The Lancet Infectious Diseases, Jun. 2004, 337-348.

Young, et al., "Polyvinylpyrrolidone-Agarose Gel Electrophoresis Purification of Polymerase Chain Reaction-Amplifiable DNA from Soils", Applied and Environmental Microbiology, Jun. 1993, 1972-1974.

Zaytseva, et al., "Multi-analyte single-membrane biosensor for the serotype-specific detection of Dengue virus", Anal. Bioanal. Chem., 2004, 46-53.

Zeng, et al., "High GC Amplification: A Comparative Study of Betaine, DMSO, Formamide and Glycerol as Additives", Life Science Journal, 2006, 67-71.

Zhang, et al., "PCR microfluidic devices for DNA amplification", Biotechnology Advances, 2006, 243-284.

Zijlmans, et al., "Detection of Cell and Tissue Surface Antigens Using Up-Converting Phosphors: A New Reporter Technology", Analytical Biochemistry, 1999, 30-36.

Zuiderwijk, et al., "An amplication-free hybridization-based DNA assay to detect Streptococcus pneumoniae utilizing the up-convewrting phosphor technology", Clinical Biochemistry, 2003, 401-403.

Huang, et al., "A capillary-driven microfluidic device for rapid dan detection with extremely low sample consumption", 17th International Conference on Miniaturized Systems for Chemistry and Life Sciences, pp. 191-193, 2013.

18786984.7, Extended European Search Report, Dec. 10, 2020, 8 pages.

"Jikken Igaku Bessatsu Mokuleki De Eraberu PCR Jikken Protocol", Jan. 1, 2011, 50-53.

"Kodak DCS Quick Start Guide", 2005.

"Microarray technology: An array of opportunities", Nature, Apr. 25, 2002, 885-891.

"nanoComposix", http://www.nanocomposix.com/pages/gold-colloid, 2014.

Akane, et al., Identification of the Heme Compound Copurified with Deoxyribonucleic Acid (DNA) from Bloodstains, a Major Inhibitor of Polymerase Chain Reaction (PCR) Amplification1.,., Journal of Forensic Sciences, Mar. 1994, 362-372.

Iakobashvili, et al., "Low temperature cycled PCR protocol for Kienow fragment of DNA polymerase I in the resence of proline", Nucleic Acids Research, 1999, 1566-1568.

Al-Soud, et al., "Effects of Amplification Facilitators on Diagnostic PCR in the Presence of Blood, Feces, and Meal", Dec. 2000, 4463-4470.

Albretsen, et al., "Optimal Conditions for Hybridization with Oligonucleolides: A Study with myc—Oncogene DNA Probes", Analytical Biochemistry, 1988, 193-202.

An, et al., "Characterization of a Thermostable UvrD Helicase and Its Participation in Helicase-dependenl Amplificalion", The Journal of Biological Chemistry, Aug. 12, 2005, 28952-28958.

Andreotti, et al., "Immunoassay of infectious agents", BioTechniques Euro Edition, Oct. 2003, 850-859.

Ausbel, et al., "Current Protocols in Molecular Biology", John Wiley & Sons, Inc., 1992, 15.6.1-15.6.4.

Aveyard, et al., "One Step Visual Detection of PCR Products with Gold Nanoparticles and a Nucleic Acid Lateral Flow (NALF) Device", Chemical Communications, 2007.

Baeumner, "Biosensors for environmental pollutants and food contaminants", Anal Bioanal Chem, 2003, 434-445.

Baeumner, et al., "A rapid biosensor for viable B. anthracis spores", Anal. Bioanal. Chem., 2004, 15-23.

Baeumner, et al., "A Universal Nucleic Acid Sequence Biosensor with Nanomolar Detection Limits", Analytical Chemistry, Feb. 15, 2004, 888-894.

(56) References Cited

OTHER PUBLICATIONS

Baeumner, et al., "Biosensor for Dengue Virus Detection: Sensitive, Rapid, and Serotype Specific", Analytical Chemistry, Mar. 15, 2002, 1442-1448.
Barany, "The Ligase Chain Reaction in a PCR World", Genome Research, Aug. 1991, 5-16.
Barnes, "PCR amplification of up to 35-kb DNA with high fidelity and high yield from A bacteriophage emplates", Proc. Nall. Acad. Sci., vol. 91, Mar. 1994, 2216-2220.
Baskaran, et al., "Uniform Amplification of a Mixture of Deoxyribonucleic Acids with Varying GC Content", Genome Research, Jul. 1996, 633-638.
Berthelet, et al., "Rapid, direct extraction of DNA from soild for PCR analysis using polyvinylpyrrolidone spin Columns", FEMS Microbiology Letter, 1996, 17-22.
Biagini, et al., "Rapid, Sensitive, and Specific Lateral-Flow Immunochromatographic Device to Measure Anti-Anthrax Protective Antigen Immunoglobulin Gin Serum and Whole Blood", Clinical and Vaccine Immunology, May 2006, 241-546.
Blake, et al., "Thermodynamic effects offormamide on DNa stability", Nucleic Acids Research, 1996, 2095-2103.
Boom, et al., "Rapid and Simple Method for Purification of Nucleic Acids", Journal of Clinical Microbiology, Mar. 1990, 195-503.
Boom, et al., "Rapid Purification of Hepatitis B Virus DNA from Serum", Journal of Clinical Microbiology, Sep. 1991, 1804-1811.
Braasch, et al., "Locked nucleic acid {LNA): fine-tuning the recognition of DNa and RNA", Chemistry & Biology, 2001, 731-735.
Braun, et al., "Exponential DNA Replication by Laminar Convection", Physical Review Letters, Oct. 10, 2003, 158103-1-158103-4.
Bright, et al., "Incidence of adamantane resistance among influenza A {H3N2) viruses isolated worldwide from 1994 to 2005: a cause for concern", Lancet, Sep. 22, 2005, 1175-1181.
Brlansky, et al., "Colonization of the Sharpshooter Vectors, Oncometopia nigricans and Homalodisca coagulata, by Kylem-LOimited Bacteria", Phytopathology, 1983, 530.535.
Brlansky, et al., "Transmission of the Citrus Variegated Chlorosis Bacterium Xylella fastidiosa with the Sharpshooter Oncometopia nigricans", Plant Disease, Nov. 2002, 1237-1239.
Buck, et al., "Design Strategies and Performance of Custom DNA Sequencing Primers", BioTechniques, 1999, 228-536.
Buhro, et al., "Semiconductor nanocrystals: Shapemallers", Nature Materials, Mar. 2003, 138-139.
Burns, et al., "An Integrated Nanoliter DNA Analysis Device", Science, Oct. 16, 1998, 484-487.
Cai, et al., "Oscillating Amplification Reaction for Nucleic Acids", U.S. Appl. No. 51/477,437, filed Apr. 20, 2011.
Capaldi, et al., "Signal amplification through nucleotide extension and excision on a dendritic DNA platform", Nucleic Acids Research, 2000, i-vii.
Carney, et al., "Present and future applications of gold in rapid assays", IVD Technology, Mar. 1, 2006, 1-8.
Carter, et al., "Lateral flow microarrays: a novel platform for rapid nucleic acid detection based on miniaturized ateral flow chromatography", Nucleic Acids Research, 2007, 1-11.
Caruthers, et al., "Helicase structure and mechanism", Curr Opin Struc Biol, 2002, 123-133.
Cary, "An Integrated Low Cost Nucleic Acid Analysis Platform for the Rapid Detection of Plan Pathogens", Jan. 6, 2011.
Chang, et al., "Culture and Serological Detection of the Xylem-Limited Bacterium Causing Citrus Variegated Chlorosis and Its Identification as a Strain of Xylella fastidiosa", Current Microbiology, 1993, 137-142.
Chanteau, et al., "Early diagnosis of bubonic plague using F1 antigen capture ELISA assay and rapid immunogold dipstick", Int. J_ Med. Microbiol., 2000, 279-283.
Cheek, et al., "Chemiluminescence Detection for Hybridization Assays on the Flow-Thru Chip, a Three-Dimensional Microchannel Biochip[", Analytical Chemistry, Dec. 15, 2001, 5777-5783.
Cheng, et al., "Chip PCR. II. Investigation of different PCR amplification systems in Microfabricated silicon-glass hips", Nucleic Acids Research, 1996, 380-385.
Chin, et al., "Lab-on-a-chip devices for global health: Past Studies and future opportunities", Lab Chip, 2007, 41-57.
Ciapina, et al., "A nested-PCR assay for detection of Xylella fastidiosa in citrus plants and sharpshooter leafhoppers", Journal of Applied Microbiology, 2004, 546-551.
Cirino, et al., "Multiplex diagnostic platforms for detection of biothreat agents", Expert Rev. Mol. Diagn., 2004, 841-857.
Compton, "Nucleic acid sequence-based amplification", Nature, Mar. 7, 1991, 91-92.
Cook, et al., "Synthesis and hybridization of a series of biotinylated oligonucleotides", Nucleic Acids Research, 1988, 1077-4095.
Corstjens, et al., "Use of Up-Converting Phosphor Reporters in Lateral-Flow Assays to Detect Specific Nucleic Acid Sequences: A Rapid, Sensitive DNA Test to Identify Human Papillomavirus Type 16 Infection", Clinical Chemistry, 2001, 1885-1893.
Collins, "Purification and characterization ofThermus thermophilus UvrD", Extremophiles, 2003, 35-41.
Cubero, et al., "Genetic Relationship among Worldwide Strains of Xanthomonas Causing Canker in Citrus Species and Design of New Primers for Their Identification by PCR", Applied and Environmental Microbiology, Mar. 2002, 1257-1264.
Cubero, et al., "Quantitative PCR Method for Diagnosis of Citrus Bacterial Canker", Applied and Environmental Microbiology, Jun. 2001, 2849-2852.
Davis, et al., "Pierce's Disease of Grapevines: Isolation of the Causal Bacterium", Science, Jan. 6, 1978, 775-778.
Dawson, et al., "Identification of A/H5N1 Influenza Viruses Using a Single Gene Diagnostic Microarray", Anal. Chem., 2007, 378-384.
Day, et al., "Immobilization of polynucleotides on magnetic particles", Biochem. J., 1991, 735-740.
De Jong, et al., "Oseltamivir Resistance during Treatment of Influenza A (H5N1) Infection", New England Journal of Medicine, Dec. 22, 2005, 2667-2672.
Deiman, et al., "Characteristics and Applications of Nucleic Acid Sequence-Based Amplification (NASBA)", Molecular Biotechnology, 2002, 163-179.
Dineva, et al., "Simultaneous Visual Detection of Multiple Viral Amplicons by Dipstick Assay", Journal of Clinical Microbiology, Aug. 2005, 4015-4021.
Dobkin, et al., "RNA Replication: Required Ilermediates and the Dissociation of Template, Product, and QB Replicase", Biochemistry, 1979, 2038-2044.
Dong, et al., "A coupled complex of T4 Dna replication helicase (gp41) and polymerase (gp43) can perform rapid and processive DNA strand-displacement synthesis", Proc. Nall. Acad. Sci. USA, Dec. 1996, 14456-14461.
Duck, et al., "Probe Amplifier System Based on Chimeric Cycling Oligonucleotides", Biotechniques, 1990, 142-148.
Easterday, et al., "Specific detection of Bacillus Anthracis using a TaqMan mismatch amplification mutation assay". BioTechniques, 2005, 731-735.
Easterday, et al., "Use of Single Nucleotide Polymorphisms in the plxR Gene for Specific Identification of Bacillus Anthracis", Journal of Clinical Microbiology, Apr. 2005, 1995-1997.
Edwards, et al., "Optimization of DNA-tagged dye-encapsulating liposomes for lateral-flow assays based on sandwich hybridization", Anal. Bioanal. Chem., 2006, 1335-1343.
Eggerding, "A One-step Coupled Amplification and Oligonucleolide Ligation Procedure for Multiplex Genetic Typing", PCR Methods and Applications, Cold Spring Harbor Laboratory Press, 1995, 337-345.
Elliott, et al., "Use of laser microdissection greatly improves the recovery of DNA from sperm on microscope slides", Forensic Science International, 2003, 28-36.
Extended European Search Report issued by the European Patent Office for Application No. 16784104.8, dated Feb. 12, 2019, 11 pages.

(56) References Cited

OTHER PUBLICATIONS

Findlay, et al., "Automated Closed-Vessel System for inVilro Diagnostics Based on Polymerase Chain Reaction", Clinical Chemistry, 1993, 1927-1933.
Fisher, et al., "Development of a Quantum Dot-Lateral Flow Assay", BEACON e-news at Jet Propulsion Laboratory, 2003.
Fong, et al., "Rapid Solid-Phase Immunoassay for Detection of Melhicillin-Resislanl *Staphylococcus aureus* Using Cycling Probe Technology", Journal of Clinical Microbiology, Jul. 2000, 2525-2529.
Frackman, et al., "Belaine and DMSO: Enhancing Agents for PCR", Promega Noles, 1998, 27.
Fu, et al., "Controlled reagent transport in disposable 2D paper networks", Lab Chip, 2010, 918-920.
Fukuta, et al., "Development of immunocapture reverse transcription loop-mediated isothermal amplification for the detection of tomato spotted will virus from chrysanthemum", Journal of Virological Methods, 2004, 49-55.
Gani, et al., "Potential Impact of Antiviral Drug Use during Influenza Pandemic", Emerging Infectious Diseases, Sep. 2005, 1355-1362.
Gill, "Application of Low Copy No. DNA Profiling", Croatian Medical Journal, 2001, 228-232.
Gill, et al., "An investigation of the rigor of interpretation rules for STRs derived from less than 100 pg of DNA", Forensic Science International, 2000, 17-40.
Glynou, et al., "Oligonucleolide-Funclionalized Gold Nanoparlices as Probes in a Dry-Reagent Strip Biosensor for DNA Analysis by Hybridization", Analytical Chemistry, Aug. 15, 2003, 4155-4160.
Goda, Tatsuro, et al., "Label-Free Potentiometry for Detecting DNa Hybridization Using Peptide Nucleic Acid and DNA Probes", Sensors, vol. 13, 2013, 2267-2278.
Goheen, et al., "Association of a Rickettsialike Organism with Pierce's Disease of Grapevines and Alfalfal Swarf and Heat Therapy of the Disease in Grapevines", Phytopathology, Mar. 1973, 341-345.
Goldmeyer, et al., "Development of a Novel One-Tube Isothermal Reverse Transcription Thermophilic Helicase-Dependent Amplification Platform for Rapid RNA Detection", Journal of Molecular Diagnostics, Nov. 2007, 639-644.
Grainge, et al., "Biochemical analysis of components of the pre-replication complex of Archaeoglobus fulgidus", Nucleic Acids Research, 2003, 4888-4898.
Groody, "Detection of Foodborne Pathogens Using DNA Probes and a Dipstick Format", Molecular Biotechnology, 1996, 323-327.
Guatelli, et al., "Isothermal, in vitro amplification of nucleic acids by a multienzyme reaction modeled after retroviral eplication", Proc. Natl. Acad. Sci. USA, Mar. 1990, 1874-1878.
Guo, et al., "Direct fluorescence analysis of genetic polymorphisms by hybridization with oligonucleotide arrays on Jlass supports", Nucleic Acids Research, 1994, 5456-5465.
Harmon, et al., "Biochemical Characterization of the DNA Helicase Activity of the *Escherichia coli* RecQ Helicase", The Journal of Biological Chemistry, 2001, 232-243.
Hartley, et al., "Biosensor for the specific detection of a single viable B. Anthracis spore", Anal. Bioanal. Chem., 2003, 319-327.
Hartung, et al., "Detection of Xanthomonas campestris pv. Citri by the Polymerase Chain Reaction Method", Applied and Environmental Microbiology, Apr. 1993, 1143-1148.
Hartung, et al., "Rapid and Sensitive Colorimetric Detection of Xanthomonas axonopodis pv. citri by Immunocapture nd a Nested-Polymerase Chain Reaction Assay", Phytopathology, 1996, 95-101.
Heller, "DNA microarray technology: devices, systems, and applications", Annu. Rev. Biomed. Eng., 2002, 129-153.
Hendson, et al., "Genetic Diversity of Pierce's Disease Strains and other Pathotypes of Xylella Fastidiosa", Applied nd Environmental Microbiology, Feb. 2001, 895-903.
Henegariu, et al., "Multiplex PCR: Critical Parameters and Step-by-Step Protocol", BioTechniques, 1997, 504-511.
Henke et al., "Betaine improves the PCR amplification of GC-rich DNA sequences", Nucleic Acids Research, vol. 25, No. 19, Oxford University Press, 1997, 3957-3958.
Hill, et al., "Acquisition and Retention of Xylella Fastidiosa by an Efficient Vector, Graphocephala atropunctata", Dhytopathology, 1997, 209-212.
Hill, et al., "Fluorescent Amplified Fragment Length Polymorphism Analysis of Bacillus anthracis, Bacillus cereus, anc Bacillus thuringiensis Isolates", Applied and Environmental Microbiology, Feb. 2004, 1068-1080.
Hill, et al., "Populations of Xylella fastidiosa in Plants Required for Transmission by an Efficient Vector", Dhytopathology, 1997, 1197-1201.
Hopkins, "Xylella Fastidiosa: Xylem-Limited Bacterial Pathogen of Plants", Ann. Rev. Phytopathol., 1989, 271-290.
Huber, et al., "Accessing Single Nucleotide Polymorphisms in Genomic DNA by Direct Multiplex Polymerase Chain Reaction Amplification on Oligonucleotide Microarrays", Analytical Biochemistry, 2002, 25-33.
Huckle, "Point-Of-care diagnostices: will the hurdles be overcome this time?", Expert Review of Medical Devices, 2006, 421-426.
Hutton et al., "Activity of Endonuclease S1 in Denaturing Solvents: Dimethylsulfoxide, Dimethylformamide, Formamide and Formaldehyde", Biochemical and Biophysical Research Communications, vol. 66, No. 3, Academic Press, Inc., 1975, 942-948.
Jacobi, et al., "Development of a multiplex immunocapture RT-PCR assay for detection and differentiation of tomato nd tobacco mosaic tobamoviruses", Journal of Virological Methods, 1998, 167-178.
Jacobsen, et al., "Direct isolation of poly{A)+ RNA from 4 M guanidine thiocyanate-lysed cell extracts using locked ucleic acid-oligo(T) capture", Nucleic Acid Research, 2004, 1031-1042.
Jensen, et al., "DMSO and Betaine Greatly Improve Amplification of GC-Rich Constructs in De Novo Synthesis", PLoS One, Jun. 11, 2010, e11024.
Jobling, et al., "Encoded Evidence: DNA in Forensic Analysis", Nature Reviews: Genetics, Oct. 2004, 739-751.
Kandimalla, et al., "Design, biochemical, biophysical and biological properties of cooperative antisense Jligonucleotides", Nucleic Acids Research, 1995, 3578-3584.
Kane, Michael D., et al., "Assessment of the sensitivity and specificity of oligonucleotide (50mer) microarrays", Nucleic Acids Research, Vo. 28, No. 22, Oxford University Press, 2000, 4552-4557.
Kaplan, et al., "DnaB from Thermus aquaticus Unwinds Forked Duplex DNA with an Asymmetric Tail Length Dependence", The Journal of Biological Chemistry, Mar. 12, 1999, 6889-6897.
Kempitiya, et al., "Localized microwave heating in microwells for parallel DNA amplification applications", Applied Physics Letters, 2009, 064106-1-064106-3.
Keohavong, et al., "Fidelity of DNa polymerases in DNA amplification", Proc. Nall. Acad. Sci. USA, Dec. 1989, 9253-9257.
Kieleczawa, et al., "DNA Sequencing by Primer Walking with Strings of Conlinguous Hexamers", Science, Dec. 11, 1992, 1787-1791.
Kievits, et al., "NASBA {TM) isothermal enzymatic in vitro nucleic acid amplification oplimzed for the diagnosis of HIV-1 infection", Journal of Virological Methods, 1991, 273-286.
Kilbourne, et al., "The total influenza vaccine failure of 1947 revisited: Major inlrasubtypic antigenic change can explain failure of vaccine in a post-World War II epidemic", PNAS, Aug. 6, 2002, 10748-10752.
Kim et al., "Recombinant fragment assay for gene targeting based on the polymerase chain reaction", Nucleic Acids Research, vol. 16, No. 18, IRL Press Limited, Oxford, England, 1988, 8887-8903.
Kimura, et al., "One-step immobilization ofr poly(dT)-modified DNA onto non-modified plastic substrates by UV rradialion for microarrays", Biochemical and Biophysical Research Communications, 2006, 477-484.
Koch, "Technology Platforms for Pahrmacogenomic Diagnostic Assays", Nature Reviews Drug Discovery, Sep. 2004, 749-761.
Kohn, "An Immunochromatographic Technique", Immunology, 1968, 863-865.

(56) References Cited

OTHER PUBLICATIONS

Koonjul, "Inclusion of polyvinylpyrrolidone in the polymerase chain reaction reverses the inhibitory effects of polyphenolic contamination of RHNA", Nucleic Acids Research, 1999, 915-916.
Kornberg, et al., DNA Replication, 1992, 298-299; 356-365.
Kozwich, et al., "Development of a Novel, Rapid Integrated Cryptosporidium Parvum Detection Assay", Applied and Environmental Microbiology, Jul. 2000, 2711-2717.
Kwoh, et al., "Transcription-based amplification system and detection of amplified human immunodeficiency virus type 1 with a bead-based sandwich hybridization formal", Proc. Nall. Acad. Sci. USA, Feb. 1989, 117301177.
Landegren, et al., "A Ligase-Medialed Gene Detection Technique", Science, Aug. 26, 1988, 1077-1080.
Lane, et al., "The thermodynamic advantage of DNA oligonucleolide 'slacking hybridization' reactions: energetics of a DNA nick", Nucleic Acids Research, 1997, 611-616.
Leone, et al., "Direct detection of potato leafroll virus in potato tubers by immunocapture and the isothermal nuclic Acid amplification method NASBA", Journal of Virological Methods, 1997, 19-27.
Liao, et al., "Miniature RT-PCT system for diagnosis of RNA-based viruses", Nucleic Acids Research, Oct. 12, 2005, 1-7.
Lim, et al., "Current and Developing Technologies for Monitoring Agents of Biolerrorism and Biowarfare", Clinical Microbiology Reviews, Oct. 2005, 583-607.
Liu, et al., "Self-Contained, Fully Integrated Biochip for Sample Preparation, Polymerase Chain Reaction Amplification and DNA Microarray Detection", Anal. Chem., vol. 76, 2004, 1824-1831.
Lockley, et al., "Colorimetric detection of immobilised PCR products generated on a solid support", Nucleic Acids Research, 1997, 1313-1314.
Loens, et al., "Evaluation of NucliSens easyMAG for Automated Nucleic Acid Extraction from Various Clinical Specimens", Journal of Clinical Microbiology, Feb. 2007, 421-425.
Lonnberg, et al., "Chromatographic performance of a thin microporous bed of nitrocellulose", Journal of Chromatography B, 2001, 107-120.
Lowe, et al., "Multiplexed, Particle-Based Detection of DNa Using Flow Cytometry with 3DNA Dendrimers for Signal Amplificalion", Cytometry Part A, 2004, 135-144.
Ilyushina, et al., "Detection of amantadine-resistant variants among avian influenza viruses isolated in North America and Asia", Virology, 2005, 102-106.
Mackay, "Real-lime PCR in the microbiology laboratory", Clin Microbiol Infecl., 2004, 190-212.
Malek, et al., "Nucleic acid sequence-based amplification (NASBA)", Protocols for Nucleic Acid Analysis by Nonradioactive Probes, ed. Peter G. Isaac, 1994, 253-260.
Masny, et al., "Ligation mediated PCR performed at low denaturation temperatures-PCT melting profiles", Nucleic Acids Research, 2003, 1-6.
Michalet, et al., "Properties of Fluorescent Semiconductor Nanocrystals and their Application to Biological Labeling" Single Mol., 2001, 261-276.
Miyoshi, et al., "Molecular Crowding Regulates the Structural Switch of the DNA G-Quadruplex", Biochemistry, Nov. 20, 2002, 15017-15024.
Monteiro, et al., "Complex Polysaccharides as PCR Inhibitors in Feces: Helicdobacter pylori Model", Journal of Clinical Microbiology, Apr. 1997, 995-998.
Mouritzen et al., "Single Nucleotide Polymorphism Genotyping Using Locked Nucleic Acid (LNA(Trademark))," January, vol. 3, No. 1, pp. 27-38 (2003).
Mumford, et al., "Rapid single-tube immunocapture RT-PCT for the detection of two yam potyviruses", Journal of Virological Methods, 1997, 73-79.
Musso, et al., "Betaine, Dimethyl Sulfoxide, and 7-Deaza-dGTP, a Powerful Mixture for Amplification of GC-Rich DNJ Sequences", Journal of Molecular Diagnostics, Nov. 2006, 544-550.
Nicholson, et al., "Influenza", The Lancet, Nov. 22, 2003, 1733-1745.
O'Meara, et al., "Capture of Single-Stranded DNa Assisted by Oligonucleotide Modules", Analytical Biochemistry, 1998, 195-203.
O'Meara, et al., "Cooperative Oligonucleotides Mediating Direct Capture of Hepatitis C Virus RNa from Serum", Journal of Clinical Microbiology, Sep. 1998, 2454-2459.
Palese, et al., "Influenza vaccines: present and future", The Journal of Clinical Investigation, Jul. 2002, 9-13.
Pannucci, et al., "Virulence signatures: microarray-based approaches to discovery and analysis", Biosensors and Biolelectronics, 2004, 706-718.
Pastinen, et al., "A System for Specific, High-throughput Genotyping by Allele-specific Primer Extension on Microarrays", Genome Research, 2000, 1031-1042.
PCR Amplification, Protocols and Applications Guide, https://www.promega.ca/resources/product-guides-and-selectors/protocols-and-applications-guide/per-amplification/, 2016.
Pemov, et al., "DNA analysis with multiplex microarray-enhanced PCR", Nucleic Acid Research, 2005, 1-9.
Petrik, "Diagnostic applications of microarrays", Transfusion Medicine, 2006, 233-247.
Peytavi, et al., "Microfluidic Device for Rapid (<15 min) Automated Microarray Hybridization", Clinical Chemistry, 2005, 1836-1844.
Piepenburg, et al., "DNA Detection Using Recombination Proteins", PLoS Biology, Jul. 2006, 1115-1121.
Pooler, et al., "Detection of Xylella fastidiosa in potential insect vectors by immunomagnetic separation and nested polymerase chain reaction", Letters in Applied Microbiology, 1997, 1230126.
Pooler, et al., "Specifric PCR Detection and Identification of Xylella fastidiosa Strains Causing Citrus Variegated Chlorosis", Current Microbiology, 1995, 377-381.
Pristoupil, "Microchromatography and Microelectrophoresis on Nitrocellulose Membranes", Chromatographic Reviews, 1970, 109-125.
Purcell, et al., "Fate of Pierce's Disease Strains of Xylella fastidiosa in Common Riparian Plants in Californial", Diani Disease, 1999, 825-830.
Purcell, et al., "Pierce's Disease Bacterium: Mechanism of Transmission by Leafhopper Vectors", Science, Nov. 16, 1979, 839-841.
Rajendrakumar et al., "DNA helix destabilization by praline and betaine: possible role in the salinitiy tolerance process," FEBS Letters, vol. 410, Federation of European Biochemical Sciences, 1997, 201-205.
Ralser, et al., "An efficient and economic enhancer mix for PCR", Biochemical and Biophysical Research Communications, 2006, 747-751.
Rao, et al., "Developing rapid, point-Of-care, multiplex detection for use in lateral flow devices", Smart Medical and Biomedical Sensor Technology III, Proc. of SPIE, 2005.
Rapley, "Enhancing PCR Amplification and Sequencing Using DNA-Binding Proteins", Molecular Biotechnology, Dec. 1994, 295-298.
Rees et al., "Betaine can eliminate the base pair composition dependence of DNA melting", Biochemistry, 1993 [Abstract], 1993.
Reinhartz, et al., "A novel rapid hybridization technique: paper chromatography hybridization assay (PACHA)", Gene, 1993,221-226.
Rodriguez, et al., "Detection and Diversity Assessment of Xylella fastidiosa in Field-Collected Plant and Insect Samples by Using 16S rRNA and gyrB Sequences", Applied and Environmental Microbiology, Jul. 2003, 4249-4255.
Romero, et al., "Amplification and cloning of a long RNA virus genome using immunocapture-long RT-PCR", Journal of Virological Methods, 1997, 159-163.
Roper, et al., "Advances in Polymerase Chain Reaction on Microfluidic Chips", Analytical Chemistry, 2005, 3887-3894.
Rouse, et al., "Microarray technology—an intellectual property retrospective", Pharmacogenomics, 2003, 1462-2416.
Rule, et al., "Rapid method for visual identification of specific DNA sequences based on DNA-tagged liposomes", Clinical Chemistry, 1996, 1206-1209.

(56) References Cited

OTHER PUBLICATIONS

Saiki, et al., "Primer-Directed Enzymatic Amplification of DNA with a Thermostable DNA Poymerase", Science, Jan. 29, 1988, 487-491.
Sambrook, et al., Molecular Cloning: A Laboratory Manual, 2001, 9.47-9.55.
Sarkar, et al., "Formamide can dramatically improve the specificity of PCR", Nucleic Acids Research, Dec. 25, 1990, 7465.
Schildkraut, et al., "Dependence of the Melting Temperature of DNA on Salt Concentration", Biopolymers, 1965, 195-208.
Schuchard et al., "Two-Step "Hot" PCR Amplification of GC-Rich Avian c-yc Sequences", BioTechniques, vol. 14, No. 3, 1993, 390-394.
Schwab, et al., "Immunoaffinity concentration and purification of waterborne enteric viruses for detection by reverse transcriptase PCR", 1996, 2086-2094.
Shoffner, et al., "Chip PCR. I. Surface passivation of microfabricated silicon-glass chips for PCR", Nucleic Acids Research, 1996, 375-379.
Singh, et al., "LNA (locked nucleic acids): synthesis and high-affinity nucleic acid recognition", Chem. Commun., 1998, 455-456.
Spiess, "Trehalose Is a Potent PCR Enhancer: Lowering of DNA Melting Temperature and Thermal Stabilization of Taq Polymerase by the Disaccharide Trehalose", Clinical Chemistry, Jul. 2004, 1256-1259.
Spiro, et al., "A Bead-Based Method for Multiplexed Identification and Quantitation of DNA Squences Using Flow Cytometry", Applied and Environmental Microbiology, Oct. 2000, 4258-4265.
Stears, et al., "A novel, sensitive detection system for high-density microarrays using dendrimer technology", Physiol. Genomics, 2000, 93-99.
Sterne, "The use of Anthrax Vaccines Prepared from Avirulent (Uncapsulated) Variants of Bacillus anthracis", Onderstepoort Journal of Veterinary Science and Animal Industry, Oct. 1939, 307-312.
Stiver, "The treatment of influenza with antiviral drugs", CMAJ, Jan. 7, 2003, 49-57.
Sunen, et al., "Recovery and detection of enterovirus, hepatits A virus and Norwalk virus in hardshell clams (Mercenaria mercenaria) by RT-PCT methods", Journal of Virological Methods, 1999, 179-187.
Tennikova, et al., "An Introduction to Monolithic Disks as Stationary Phases for High Performance Biochromatography", J. High Resol. Chromatogr., 2000, 27-38.
Tennikova, et al., "High-performance membrane chromatography: highly efficient separation method for proteins in on-exchange, hydrophobic interaction and reversed-phase models", Journal of Chromatography, 1993, 279-288.
Thommes, et al., "Membrane Chromatography-An Integrative Concept in the Downstream Processing of Proteins", Biotechnol. Prog., 1995, 357-367.
Tsai, et al., "Rapid Method for Separation of Bacterial DNA from Humic Substances in Sediments for Polymerase Chain Reaction", Applied and Environmental Microbiology, Jul. 1992, 2292-2295.
Van Ness, et al., "Isothermal reactions for the amplification of oligonucleotides", PNAS, Apr. 15, 2003, 4504-4509.
Varadaraj et al., "Denaturants or cosolvents improve the specificity of PCR amplification of a G + C-rich DNA using genetically engineered DNA polymerases", Gene, 140, Elsevier Science B.V., 1994, 1-5.
Vincent, et al., "Helicase-dependent isothermal DNa amplification", EMBO Reports, 2004, 795-800.
Wahlestedt, et al., "Potent and nontoxic antisense oligonucleolides containing locked nucleic acids", PNAS, May 9, 2000, 5633-5638.
Walker, et al., "Isothermal in vitro amplification of DNA by a restriction enzyme/DNA apolymerase system", Proc. Natl. Acad. Sci. USA, Jan. 1992, 392-396.
Walker, et al., "Strand displacement amplification-an isothermal, in vitro DNA amplification technique", Nucleic Acid Research, 1992, 1691-1696.
Wang et al., "Identifying Influenza Viruses with Resequencing Microarrays," Emerging Infectious Diseases, April, vol. 12, No. 4, pp. 638-646. (2006).
Wang, et al., "Droplet-based micro oscillating-flow PCR chip", Journal of Micromechanics and Microengineering, 2005, 1369-1377.
Webby, et al., "Are we ready for pandemic influenza?", Science, Nov. 28, 2003, 1519-1522.
Webster, et al., "Potential Impact of Antiviral Drug Use during Influenza Pandemic", American Scientist, 2003, 122-129.
Wei, et al., "Using a microfluidic device for 1 ul DNA micrarray hybridization in 500 s", Nucleic Acids Research, 2005, 1-11.
Weighardt, et al., "A Simple Procedure for Enhancing PCR Specificity", PCR Methods and Applications, Aug. 1, 1993, 77-81.
Wells, et al., "Isolation, Culture, and Palhogenicity of the Bacterium Causing Phony Disease of Peach", Dhytopathology, 1983, 859-862.
Wetzel, et al., "A highly sensitive immunocapture polymerase chain reaction method for plum pox potyvirus election", Journal of Virological Methods, Jul. 1992, 27-37.
Wickenheiser, "Trace DNA: A Review, Discussion of Theory, and Application of the Transfer of Trace Quantities of DNA Through Skin Contact", J Forensic Sci, 2002, 442-450.
Wilding, et al., "PCR in a Silicon Microstructure", Clinical Chemistry, 1994, 1815-1818.
Wilson, "Inhibition and Facilitation of Nucleic Acid Amplification", Applied and Environmental Microbiology, 1997, 3741-3751.

\* cited by examiner

AUTOMATED METHOD FOR PERFORMING AN ASSAY

CROSS-REFERENCE TO RELATED APPLICATIONS

This application is a continuation of U.S. patent application Ser. No. 15/137,983 (filed Apr. 25, 2016); which claims priority to and the benefit of U.S. Provisional Patent Application No. 62/322,738 (filed Apr. 14, 2016) and U.S. Provisional Patent Application No. 62/152,724 (filed Apr. 24, 2015). The disclosures of the foregoing applications are incorporated herein by reference in their entireties for any and all purposes.

BACKGROUND OF THE INVENTION

Field of the Invention (Technical Field)

Embodiments of the present invention relate to an integrated device and related methods for detecting and identifying nucleic acids. The device may be fully disposable or may comprise a disposable portion and a reusable portion.

BACKGROUND ART

Note that the following discussion may refer to a number of publications and references. Discussion of such publications herein is given for more complete background of the scientific principles and is not to be construed as an admission that such publications are prior art for patentability determination purposes.

As the public health impact and awareness of infectious and emerging diseases, biothreat agents, genetic diseases and environmental reservoirs of pathogens has increased, the need for more informative, sensitive and specific point-of-use rapid assays has increased the demand for polymerase chain reaction (PCR)-based tools. Nucleic acid-based molecular testing by such methods as PCR-based amplification is extremely sensitive, specific and informative. Unfortunately, currently available nucleic acid tests are unsuitable or of limited utility for field use because they require elaborate and costly instrumentation, specialized laboratory materials and/or multiple manipulations dependent on user intervention. Consequently, most samples for molecular testing are shipped to centralized laboratories, resulting in lengthy turn-around-times to obtain the required information.

To address the need for rapid point-of-use molecular testing, prior efforts have focused on product designs employing a disposable cartridge and a relatively expensive associated instrument. The use of external instrumentation to accomplish fluid movement, amplification temperature control and detection simplifies many of the engineering challenges inherent to integrating the multiple processes required for molecular testing. Unfortunately, dependence upon elaborate instrumentation imposes tremendous economic barriers for small clinics, local and state government and law enforcement agencies. Further, dependence upon a small number of instruments to run tests could cause unnecessary delays during periods of increased need, as occurs during a suspected biowarfare agent release or an emerging epidemic. Indeed, the instrument and disposable reagent cartridge model presents a potentially significant bottleneck when an outbreak demands surge capacity and increased throughput. Additionally, instrumentation dependence complicates ad hoc distribution of test devices to deployment sites where logistic constraints preclude transportation of bulky associated equipment or infrastructure requirements are absent (e.g. reliable power sources).

Gravity has been described as a means of fluid movement in existing microfluidic devices. However, the typical device does not allow for programmable or electronic control of such fluid movement, or the mixing of more than two fluids. Also, some devices utilize a pressure drop generated by a falling inert or pre-packaged fluid to induce a slight vacuum and draw reactants into processing chambers when oriented vertically, which increases storage and transport complexities to ensure stability of the pre-packaged fluids. Existing devices which teach moving a fluid in a plurality of discrete steps require frangible seals or valves between chambers, which complicates operation and manufacture. These devices do not teach the use of separate, remotely located vents for each chamber.

Typical microfluidic devices make use of smaller reaction volumes than are employed in standard laboratory procedures. PCR or other nucleic acid amplification reactions such as loop mediated amplification (LAMP), nucleic acid based sequence amplification (NASBA) and other isothermal and thermal cycling methods are typically conducted in testing and research laboratories using reaction volumes of 5 to 100 microliters. These reaction volumes accommodate test specimen volumes sufficient to ensure the detection of scarce assay targets in dilute specimens. Microfluidic systems that reduce reaction volumes relative to those employed in traditional laboratory molecular testing necessarily also reduce the volume of specimen that can be added to the reaction. The result of the smaller reaction volume is a reduction in capacity to accommodate sufficient specimen volume to ensure the presence of detectable amounts of target in dilute specimens or where assay targets are scarce.

SUMMARY OF THE INVENTION

The present invention is a cassette for detecting a target nucleic acid, the cassette comprising a plurality of chambers, a plurality of vent pockets connected to the chambers, and a heat labile material for sealing one or more of the vent pockets, wherein at least one the vent pocket comprises a protrusion. The protrusion preferably comprises a dimple or an asperity and preferably sufficiently prevents molten heat labile material from attaching to a heat stable material disposed adjacent to the heat labile material to prevent resealing of the vent pocket after the heat labile material is ruptured.

The present invention is also a cassette for detecting a target nucleic acid, the cassette comprising a plurality of chambers, a plurality of vent pockets connected to the chambers, a heat labile material for sealing one or more of the vent pockets, a heat stable material, and a gasket disposed between the heat labile material and the heat stable material, the gasket comprising an opening encompassing the plurality of vent pockets. The gasket is preferably sufficiently thick to provide a sufficient air volume to equilibrate pressures and ensure free air movement between open vent pockets. The cassette preferably comprises a flexible circuit, the flexible circuit comprising patterned metallic electrical components disposed on the heat stable material. The gasket preferably comprises a second opening, or is limited in dimension, such that the flexible circuit will be in direct contact with fluid in at least one of the chambers. The electrical components preferably comprise resistive heating elements or conductive traces. The resistive heating elements are preferably aligned with the vent pockets and the chambers. The cassette preferably comprises one or more ambient temperature sensors for adjusting a heating temperature, heating time, and/or heating rate of one or more of the chambers.

The present invention is also a cassette for detecting a target nucleic acid, the cassette comprising a vertically oriented detection chamber, a lateral flow detection strip disposed in the detection chamber oriented such that a sample receiving end of the detection strip is at the bottom end of the detection strip, and a space in the detection chamber below the lateral flow detection strip for receiving fluid comprising amplified target nucleic acids, the space comprising sufficient capacity to accommodate an entire volume of the fluid at a height that enables the fluid to flow up the detection strip by capillary action without flooding or otherwise bypassing regions of the detection strip. The space preferably comprises detection particles such as dye polystyrene microspheres, latex, colloidal gold, colloidal cellulose, nanogold, or semiconductor nanocrystals. The detection particles preferably comprise oligonucleotides complementary to a sequence of the amplified target nucleic acids or ligands, such as biotin, streptavidin, a hapten or an antibody, capable of binding to the amplified target nucleic acids. The detection particles have preferably been dried, lyophilized, or present on at least a portion of the interior surface as a dried mixture of detection particles in a carrier, such as a polysaccharide, a detergent, or a protein, to facilitate resuspension of the detection particles. A capillary pool of the fluid preferably forms in the space, providing improved mixing and dispersion of the detection particles to facilitate comingling of the detection particles with the amplified target nucleic acid. The cassette optionally performs an assay having a volume less than about 200 µL, and preferably less than about 60 µL.

The present invention is also a cassette for detecting a target nucleic acid, the cassette comprising one or more recesses for containing at least one lyophilized or dried reagent, at least one of the recesses comprising one or more structures for directing fluids to facilitate rehydration of the at least one dried or lyophilized reagent, the recesses disposed in one or more channels connected to the chambers or in one or more of the channels. The structures preferably comprise ridges, grooves, dimples, or combinations thereof.

The present invention is also a cassette for detecting a target nucleic acid, the cassette comprising at least one chamber comprising a feature to prevent fluid vertically entering a top of the chamber from flowing directly into an outlet of the chamber. The feature preferably deflects the fluid to the side of the chamber opposite from the outlet. The resulting flow path of the fluid preferably comprises a horizontal component, thereby sufficiently increasing the effective length of the flow path and sufficiently decreasing the flow velocity of the fluid to restrict the amount of fluid exiting the outlet. The feature preferably creates a swirling of fluid within the chamber, thereby increasing mixing of reagents within the fluid. The feature is preferably triangular or trapezoidal in shape. The outlet is optionally tapered. A channel located downstream of the outlet optionally comprises turns for increasing an effective length of the channel. The feature is preferably located near or at a bottom of the chamber or near a middle of the chamber.

The present invention is also a method of controlling vertical flow of a fluid through a chamber in a cassette for detecting a target nucleic acid, the method comprising deflecting a flow of fluid entering a top of the chamber, thereby preventing the fluid from flowing directly into an outlet of the chamber. The method preferably comprises reducing a flow velocity of the fluid, thereby reducing a distance the fluid flows down a channel connected to the outlet before the fluid stops. The method preferably comprises dividing a flow of the fluid into the chamber into a first fluid flow that contacts a wall of the chamber and is directed upward, and, a second fluid flow that enters the outlet. The first fluid flow preferably swirls in the chamber, thereby increasing mixing of reagents within the fluid. The second fluid flow preferably forms a meniscus and travels through a channel connected to the outlet, the meniscus increasing pressure in closed air space in the channel downstream of the fluid until the pressure stops the flow of fluid in the channel. The outlet is optionally tapered, thereby increasing compressible air volume at the entrance to the outlet. The method optionally comprises providing turns in a channel connected to the outlet, thereby increasing an effective path length of the channel and reducing a flow velocity of fluid in the channel.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate embodiments of the present invention and, together with the description, serve to explain the principles of the invention. The drawings are only for the purpose of illustrating certain embodiments of the invention and are not to be construed as limiting the invention. In the drawings.

DETAILED DESCRIPTION OF THE INVENTION

Figure 44:
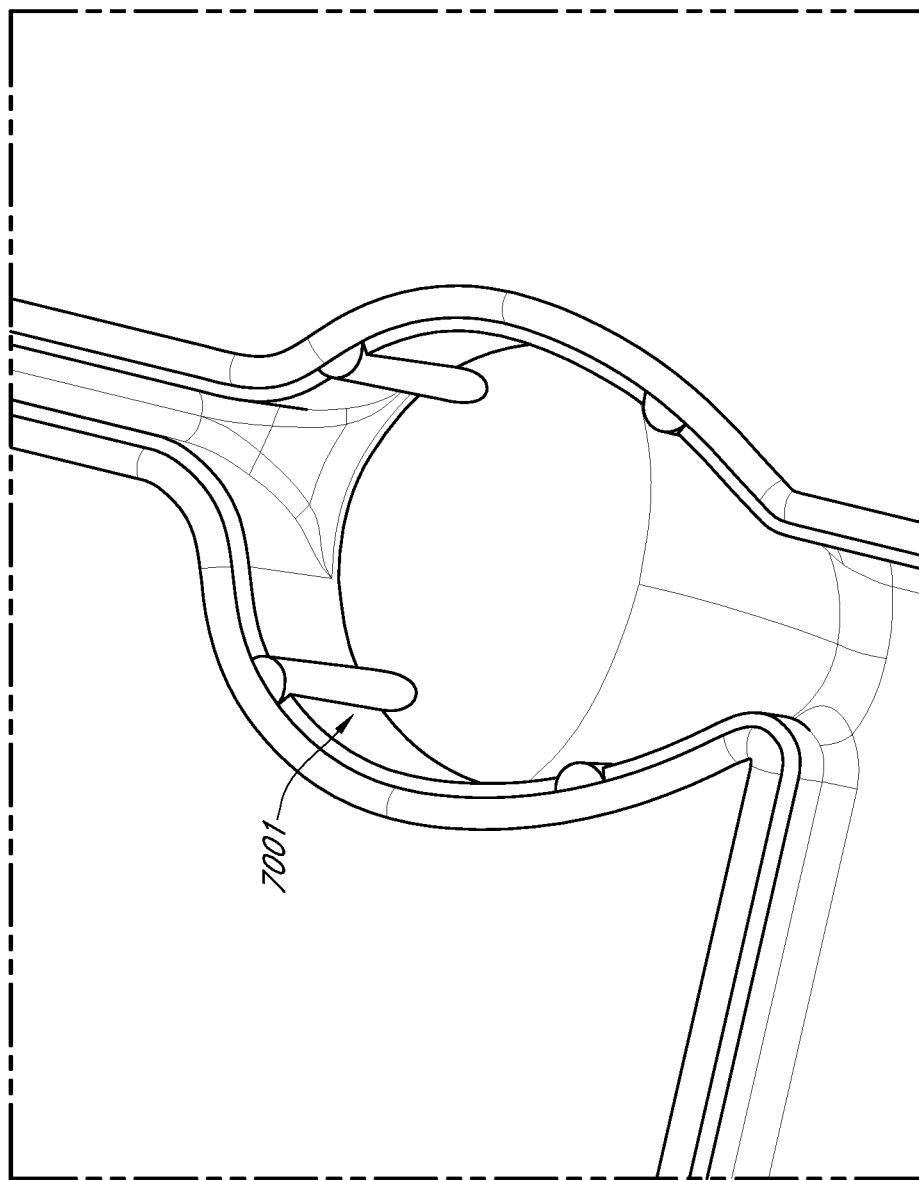
FIG. 44 shows a reagent recess comprising internal features for directing fluid flow.

An embodiment of the present invention is a sealable disposable platform for detecting a target nucleic acid, the disposable platform preferably comprising a sample chamber for receiving a sample comprising the target nucleic acid, an amplification chamber connected via a first channel to the sample chamber and connected via a second channel to a first vent pocket, a labeling chamber connected via a third channel to the amplification chamber and connected via a fourth channel to a second vent pocket, a detection subsystem connected to the labeling chamber via a fifth channel and connected via a sixth channel to a third vent pocket, a plurality of resistive heating elements, and one or more temperature measuring devices, wherein the vent pockets are each sealed from communication with an air chamber by a heat labile material in a suitable form, such as a membrane, a film, or a plastic sheet located in a vicinity of one or more of the resistive heating elements. The disposable platform optionally comprises a seal to seal the platform prior to the initiation of the detection assay. The disposable platform preferably comprises recesses along channels between chambers to accommodate the incorporation of dried or lyophilized reagents into the disposable platform. These recesses may optionally comprise structures on one or more of the surfaces facing the reagent(s) to assist with directing fluids, preferably using capillarity or surface tension effects, to the enclosed dried reagents to facilitate rehydration of the dried reagents. Such features may comprise ridges, such as ridge 7001 of FIG. 44, grooves, dimples or other structures to direct fluids to the internal space of the recess as the fluid passes through the recess, or otherwise assist in fluid flow to the internal space of the recess during fluid flow. Alternatively, a recess may be directly located within one (or more) of the chambers.

The disposable platform optionally further comprises a sample preparation stage comprising an output in direct fluid connection with an input of the sample chamber. Dimensions of a substantially flat surface of the amplification chamber are preferably approximately the same as dimensions of a substantially flat surface of a resistive heating element in thermal contact with the amplification chamber. The amplification chamber optionally contains an amplification solution and a recess in the channel from the sample chamber to the amplification chamber optionally comprises a lyophilized amplification reagent mix, and there is preferably a recess in the channel from the amplification chamber to the labeling chamber comprising dried or lyophilized detection particles. The amplification and labeling chambers are preferably heatable using resistive heating elements. The detection subsystem preferably comprises a lateral flow strip that comprises detection particles. The chambers, the channels, and the vent pockets are preferably located on a fluid assembly layer, and the electronic elements of the device are preferably located on a separate layer comprising a printed circuit board, the separate layer bonded to the fluid assembly layer or placed in contact with the fluid assembly layer by a docking unit. The detection subsystem is preferably located on the fluid assembly layer or optionally on a second fluid assembly layer. The volume of at least one of the chambers is preferably between approximately 1 microliter and approximately 150 microliters. The disposable platform preferably further comprises a connector for docking the disposable platform with a docking unit or docking unit, which preferably maintains the disposable platform in a vertical or tilted orientation and optionally provides electrical contacts, components and/or a power supply.

An embodiment of the present invention is a method for detecting one or more target nucleic acids, the method preferably comprising dispensing a sample comprising the target nucleic acid in a sample chamber of a disposable platform; orienting the disposable platform vertically or at a tilt; opening a first vent pocket connected to an amplification chamber to an enclosed air volume, thereby enabling the sample to flow into the amplification chamber, reacting the sample with a previously lyophilized amplification reagent mix located in a recess of the channel between sample chamber and amplification chamber, amplifying the target nucleic acid in the amplification chamber, opening a second vent pocket connected to a labeling chamber to an enclosed air volume, thereby enabling the amplified target nucleic acid to flow into the labeling chamber, labeling the amplified target nucleic acid using detection particles in a recess in the channel between the amplification chamber and the labeling chamber, opening a third vent pocket connected to a detection subsystem to an enclosed air volume, thereby enabling the labeled target nucleic acid to flow into the detection subsystem, and detecting the amplified target nucleic acid. The amplifying step preferably comprises amplifying the target nucleic acid using a resistive heating element located within the disposable platform in a vicinity of the amplification chamber. The method preferably further comprises passively cooling the amplification chamber. The method preferably further comprises heating the labeling chamber during the labeling step using a resistive heating element located within the disposable platform in a vicinity of the labeling chamber. The method preferably further comprises controlling operation of the disposable platform by using a docking unit which is not an external instrument.

Embodiments of the present invention comprise a disposable platform which integrates external instrument-independent means of conducting all requisite steps of a nucleic acid molecular assay and complements current immuno-lateral flow rapid assays with a new generation of nucleic acid tests offering more informative and sensitive analyses. Embodiments of the present invention facilitate the broader use of rapid nucleic acid testing in small clinics and austere or remote settings where infectious disease, biothreat agent, agriculture and environmental testing are the most likely to have the greatest impact. Certain embodiments of the present invention are completely self-contained and disposable which enables "surge capacity" in times of increased demand by allowing parallel tests to be run without external instrument-imposed bottlenecks. Additionally, in those application areas where a low cost disposable cartridge coupled with an inexpensive battery-powered or AC adapter energized docking unit is preferable, an embodiment of the invention where a simple docking unit is employed further reduces test costs by placing reusable components in a reusable yet inexpensive base. The platform technology disclosed herein offers sensitivity similar to laboratory nucleic acid amplification-based methods, minimal user intervention and training requirements, sequence specificity imparted by both amplification and detection, multiplex capacity, stable reagents, compatibility with low-cost large-scale manufacturing, battery or solar powered operation to allow use in austere settings, and a flexible platform technology allowing the incorporation of additional or alternative biomarkers without device redesign.

Embodiments of the present invention provide systems and methods for low-cost, point-of-use nucleic acid detection and identification suitable to perform analyses in locations remote from a laboratory environment where testing would ordinarily be performed. Advantageously, nucleic acid amplification reaction volumes can be in the same volume range commonly used in traditional laboratory testing (e.g. 5-150 µL). The reaction conducted in embodiments of the present invention is thus directly comparable to accepted laboratory assays, and allows the accommodation of the same specimen volumes typically employed in traditional molecular testing. Furthermore, the amplification of nucleic acids preferably takes place in a hermetically sealed test cassette that is preferably permanently sealed prior to the initiation of amplification. Retaining amplified nucleic acids within a sealed system prevents contamination of the testing environment and surrounding areas with amplification products and therefore reduces the likelihood subsequent tests will generate false positive results. The integration of a sealing system into the test cassette enables the use of a corresponding seal engagement system in the docking unit to enforce the formation of a seal at the time of assay initiation. In an embodiment of the invention, a rack and pinion mechanism is employed to slide a test cassette integrated sealing mechanism into place to ensure seal closure prior to amplification. A sensor placed in the docking unit interrogates the test cassette to confirm the seal has been formed prior to initiating the test reaction.

Embodiments of the present invention may be produced using injection molding processes and ultrasonic welding to achieve high-throughput manufacture and low cost disposable components. In some embodiments one or more recesses are provided in the fluidic component to each accommodate a dried reagent pellet. The recesses enable the use of lyophilized or otherwise dried materials to be present in the fluidic component during final assembly when ultrasonic welding may be used without disruption of the pellet by any energy introduced to the system during the welding.

Embodiments of the present invention may be used to detect the presence of a target nucleic acid sequence or sequences in a sample. Target sequences may be DNA such as chromosomal DNA or extra-chromosomal DNA (e.g. mitochondrial DNA, chloroplast DNA, plasmid DNA, etc.) or RNA (e.g. rRNA, mRNA, small RNAs, or viral RNA). Similarly, embodiments of the invention may be used to identify nucleic acid polymorphisms including single nucleotide polymorphisms, deletions, insertions, inversions and sequence duplications. Further, embodiments of the invention may be used to detect gene regulation events such as gene up- and down-regulation at the level of transcription. Thus, embodiments of the invention may be employed for such applications as: 1) the detection and identification of pathogen nucleic acids in agricultural, clinical, food, environmental and veterinary samples; 2) detection of genetic biomarkers of disease; and 3) the diagnosis of the presence of a disease or a metabolic state through the detection of relevant biomarkers of the disease or metabolic state, such as gene regulation events (mRNA up- or down regulation or the induction of small RNAs or other nucleic acid molecules generated or repressed during a disease or metabolic state) that occur in response to the presence of a pathogen, toxin, other etiologic agent, environmental stimulus or metabolic state.

Embodiments of the present invention comprise a means of target nucleic acid sample preparation, amplification, and detection upon addition of a nucleic acid sample, comprising all aspects of fluid control, temperature control, and reagent mixing. In some embodiments of the invention, the device provides a means of performing nucleic acid testing using a portable power supply such as a battery, and is fully disposable. In other embodiments of the invention, a disposable nucleic acid test cartridge works in conjunction with a simple reusable electronic component which can perform all of the functions of laboratory instrumentation such as an external instrument typically required for nucleic acid testing without requiring the use of such laboratory instrumentation or external instrument.

Embodiments of the present invention provide for a nucleic acid amplification and detection device comprising, but not limited to, a housing, a circuit board, and a fluidic or microfluidic component. In certain embodiments, the circuit board may contain a variety of surface-mount components such as resistors, thermistors, light-emitting diodes (LEDs), photo-diodes, and microcontrollers. In certain embodiments the circuit board may comprise a flexible circuit board comprising a heat stable substrate such as polyimide. Flexible circuits may, in some embodiments, comprise copper or other conductive coatings or layers deposited onto or bonded to the heat stable substrate. These coatings can be etched or otherwise patterned to so as to comprise the resistive heating elements used for biochemical reaction temperature control and/or conductive traces to accommodate such heaters and/or surface mount components, such as resistors, thermistors, light-emitting diodes (LEDs), photo-diodes, and microcontrollers. The fluidic or microfluidic component is the device portion which receives, contains, and moves aqueous samples and may be made from a variety of plastics and by a variety of manufacturing techniques, including ultrasonic welding, bonding, fusing or lamination, laser cutting, water-jet cutting, and/or injection molding. The fluidics and circuit board components are held together either reversibly or irreversibly, and their thermal coupling may be enhanced by heat conducting materials or compounds. The housing preferably serves in part as a cosmetic and protective sheath, hiding the delicate components of the microfluidic and circuit board layers, and may also serve to facilitate sample input, buffer release, nucleic acid elution, seal formation and the initiation of processes required for device functionality. For example, the housing may incorporate a sample input port, a mechanical system for the formation or engagement of a seal, a button or similar mechanical feature to allow user activation, buffer release, sample flow initiation, nucleic acid elution, and thermal or other physical interface formation between electronic components and fluidic components.

In some embodiments of the invention, the fluidic or microfluidic component comprises a series of chambers in controlled fluid communication where the chambers are optionally temperature-controlled, thereby subjecting the fluid contained therein to programmable temperature regimens. In some embodiments of the invention, the fluidic or microfluidic component comprises five chambers, preferably including an expansion chamber, a sample input chamber, a reverse transcription chamber, an amplification chamber, and a detection chamber. The sample input chamber preferably comprises a conduit to the expansion chamber, a sample input orifice where a nucleic acid containing sample may be added, a first recess wherein dried materials may be placed during manufacture for mixing with the input sample, an egress conduit leading to a second recess wherein dried materials may be placed during manufacture and a conduit leading therefrom to the reverse transcription chamber. In other embodiments functions of two or more of the chambers are consolidated into a single chamber, enabling the use of fewer chambers.

The first and second recesses may also comprise lyophilized reagents that may include, for example, suitable buffers, salt, deoxyribonucleotides, ribonucleotides, oligonucleotide primers, and enzymes such as DNA polymerase and reverse transcriptase. Such lyophilized reagents are preferably solubilized upon entrance of the nucleic acid sample into the recess. In some embodiments of the invention the first recess comprises salts, chemicals and buffers useful for the lysis of biological agents and/or the stabilization of nucleic acids present in the input sample. In some embodiments of the invention the input sample is heated in the sample input chamber to accomplish the lysis of cells or viruses present in the sample. In some embodiments of the invention the second recess comprises lyophilized reagents and enzymes such as reverse transcriptase useful for the synthesis of cDNA from RNA. In an embodiment of the invention the second recess is sufficiently isolated from the sample input chamber to allow materials within the second recess to maintain a lower temperature than the temperature of the sample input chamber during heating. In some embodiments of the invention the reverse transcription chamber comprises a conduit comprising a third recess comprising lyophilized reagents for the amplification of nucleic acids. The sample input chamber, the reverse transcription chamber, the amplification chamber and the detection chamber are preferably situated in register with and in sufficient proximity to the heater elements on the heater circuit board to provide thermal conduction when mounted to the heater board either directly or through insertion of the fluidic or microfluidic component or cassette into a docking unit. Similarly, electronic components present on the heater circuit board are preferably placed in physical contact or proximity to vent pockets in the fluidic component to enable electronic control by opening of the vent. The heater circuit board physical layout is designed to provide registration with elements of the fluidic or microfluidic component such that resistive heating elements of the heater circuit board for lysis, reverse transcription, amplification, hybridization, and/or fluid flow control are situated to form a thermal interface with elements of the fluidic component with which they interact.

In some embodiments of the invention the fluidic or microfluidic component preferably comprises five chambers, including a sample input chamber, a lysis chamber, a reverse transcription chamber, an amplification chamber, and a detection chamber and recesses for dried or lyophilized reagents located along the channels between each chamber. In this embodiment reverse transcription of RNA to cDNA and the amplification of cDNA occur in separate chambers. In this embodiment, a first recess, located along the conduit leading from the sample input cup to the lysis chamber, comprises salts, chemicals (e.g. dithiothreitol) and buffers (e.g. to stabilize, increase, or decrease pH) useful for the lysis of biological agents and/or the stabilization of nucleic acids present in the input sample. In some embodiments of the invention the input sample is heated in the heat lysis chamber having first flowed from the sample input cup through the first recess wherein the sample has optionally comingled with the substances that comprise the first recess. In other embodiments of the invention, lysis is accomplished by means of chemical treatment resulting from the comingling of the sample with chemicals in the first recess and the incubation of the sample in the presence of these chemicals in the lysis chamber.

After substantial completion of treatment in the lysis chamber, the sample solution is released by means of electronic control of a heater that non-mechanically ruptures a vent to allow the sample solution to flow via a channel through a second recess and into the reverse transcription chamber. Said second recess may optionally comprise lyophilized reagents that may include suitable buffers, salt, deoxyribonucleotides, ribonucleotides, oligonucleotide primers, and enzymes such as DNA polymerase and/or reverse transcriptase required to accomplish the reverse transcription of RNA in the sample into cDNA. Following the substantial completion of a reverse transcription reaction, a second vent is opened to release the sample solution to flow through a channel and third recess comprised of reagents required for nucleic acid amplification such as lyophilized reagents that may include suitable buffers, salt, deoxyribonucleotides, ribonucleotides, oligonucleotide primers, and enzymes such as DNA polymerase and into an amplification chamber.

Following the substantial completion of nucleic acid amplification in the amplification chamber a third vent is opened to release the sample solution to a channel leading to the detection chamber. Said channel may optionally but preferably comprise a fourth recess comprising dried or lyophilized detection reagents such as chemicals and/or detection particle conjugates useful for the detection of nucleic acids in the detection chamber. The detection chamber preferably comprises a capillary pool, reagents for the detection of the amplified nucleic acid and a lateral flow detection strip. The capillary pool preferably provides a space of sufficient capacity to accommodate the entire volume of fluid in the detection chamber at a height that enables the fluid to flow up the detection strip by capillary action without flooding or otherwise bypassing the regions of the detection strip designed to receive the fluid for correct capillary migration up the detection strip. In some embodiments of the invention the detection reagents are lyophilized reagents. In some embodiments of the invention the detection reagents comprise dyed polystyrene microspheres, colloidal gold, semiconductor nanocrystals, or cellulose nanoparticles. The sample solution comingles with the detection reagents in the detection chamber and flows by capillary action up the detection strip. Microheaters in register with the detection chamber may optionally be employed to control the temperature of the solution as it migrates up the detection strip.

In some embodiments of the invention the amplification reaction is an asymmetric amplification reaction wherein one primer of each primer pair in the reaction is present at a concentration different from the other primer of a given pair. Asymmetric reactions can be useful for the generation of single-stranded nucleic acid for the facilitation of detection by hybridization. Asymmetric reactions can also be useful for generating amplicons in a linear amplification reaction allowing quantitative or semi-quantitative analysis of target levels in a sample.

Other embodiments of the invention comprise a nucleic acid reverse transcription, amplification and detection device that is integrated with a sample preparation device. Embodiments including the sample preparation device provide a means for the communication of fluids between sample preparation subsystem output ports or valves and the input port or ports of the fluidic or microfluidic components of the device.

Other embodiments of the invention comprise a means of splitting the input sample into two or more fluid paths in the fluidic or microfluidic component. A means of splitting the input sample comprises a branched conduit to carry input fluids to a metering chamber of a volume designed to divide the fluid across multiple fluid paths. Each metering chamber comprises a channel conduit to a vent pocket and a channel conduit to the next chamber in the fluid path, for example a lysis chamber or a reverse transcription chamber or an amplification chamber.

Unless otherwise defined, all terms of art, notations and other scientific terminology used herein are intended to have the meanings commonly understood by those of skill in the art to which this invention pertains. The techniques and procedures described or referenced herein are generally well understood and commonly employed using conventional methodologies by those skilled in the art, such as, for example, the widely utilized molecular cloning methodologies described in Sambrook et al., Molecular Cloning: A Laboratory Manual 3rd. edition (2001) Cold Spring Harbor Laboratory Press, Cold Spring Harbor, N.Y. and Current Protocols in Molecular Biology (Ausbel et al., eds., John Wiley & Sons, Inc. 2001. As appropriate, procedures involving the use of commercially available kits and reagents are generally carried out in accordance with manufacturer defined protocols and/or parameters unless otherwise noted.

As used throughout the specification and claims, the terms 'target nucleic acid' or 'template nucleic acid' mean a single-stranded or double-stranded DNA or RNA fragment or sequence that is intended to be detected.

As used throughout the specification and claims, the terms 'microparticle' or 'detection particle' mean any compound used to label nucleic acid product generated during an amplification reaction, including fluorescent dyes specific for duplex nucleic acid, fluorescently modified oligonucleotides, and oligonucleotide-conjugated quantum dots or solid-phase elements such as a polystyrene, latex, cellulose or paramagnetic particles or microspheres.

As used throughout the specification and claims, the term 'chamber' means a fluidic compartment where fluid resides for some period of time. For example, a chamber may be the sample chamber, amplification chamber, labeling chamber, or the detection chamber.

As used throughout the specification and claims, the term "cassette" is defined as a disposable or consumable cassette, housing, component, or cartridge used in performing an assay or other chemical or biochemical analysis. A cassette may be single use or multiple use.

As used throughout the specification and claims, the term 'pocket' means a compartment that serves as a venting mechanism. A pocket is preferably adjacent or overlaid to a resistor or other mechanism to open the pocket. For example, unlike fluidic chambers as described above, a pocket created in the fluidic component of the cassette may have one open face that aligns with a resistor on the PCA. This open face is preferably covered by a thin membrane, film, or other material to create a sealed cavity that is easily ruptured by energizing the underlying resistor.

As used throughout the specification and claims, the term 'channel' means a narrow conduit within the fluidic assembly which typically connects two or more chambers and/or pockets or combinations thereof, including, for example, an inlet, outlet, or a vent channel. In the case of an inlet or outlet channel, fluid sample migrates through the channel. In the case of a vent channel, the conduit preferably remains clear of fluid and connects a fluidic chamber to a vent pocket.

As used throughout the specification and claims, the term "external instrument" means a reusable instrument that has one or more of the following characteristics: performs a mechanical action on a disposable assay or cassette other than sealing the cassette, including but not limited to piercing buffer packets and/or pumping or otherwise actively providing a transport force for fluids, comprises moving parts to control valves and other components for fluid flow control in the cassette or disposable assay, controls fluid flow other than by selective heating of the assay, or requires periodic calibration.

As used throughout the specification and claims, the term "docking unit" means a reusable device that controls assays but does not have any of the characteristics listed above for external instruments.

Embodiments of the present invention are devices for low-cost, point-of-use nucleic acid testing suitable to perform analyses in locations remote from a laboratory environment where testing would ordinarily be performed. Certain devices comprise fluidic and electronic components or layers, optionally encased by a protective housing. In embodiments of the present invention, the fluidic component is composed of plastic and comprises a series of chambers and pockets connected by narrow channels in which chambers are oriented vertically with respect to one another during operation. The fluidic component is overlaid or otherwise placed in physical contact with electronic components, preferably controlled via a microcontroller, such as a printed circuit board containing off-the-shelf surface mount devices (SMDs), and/or a flexible circuit comprising etched conductive material to form resistive heating elements and optionally containing SMDs. In some embodiments of the device, the entire assembly is disposable. In other embodiments, the fluidic and physically bonded electronic layers are disposable, while a small inexpensive controlling unit is reusable. In another embodiment, the fluidic component is disposable, and a small controlling docking unit or docking unit is reusable. For all embodiments, the present invention may be integrated with a nucleic acid sample preparation device such as that described in International Publication No. WO 2009/137059 A1, entitled "Highly Simplified Lateral Flow-Based Nucleic Acid Sample Preparation and Passive Fluid Flow Control" (incorporated herein by reference), and/or use methods described therein.

Embodiments of the present invention comprise an integrated nucleic acid testing device that can be manufactured inexpensively with established manufacturing processes. The invention provides molecular test data while retaining the simplicity from the end-user perspective of widely accepted hand-held immunoassays, overcoming the challenges of regulating fluid temperatures within the device, transporting small sample volumes in sequential steps, reagent addition, reagent mixing, detecting nucleic acids. In some embodiments of the invention subsystems for collecting, interpreting, reporting and/or transmitting assay results are incorporated into the invention. Embodiments of the present invention are uniquely adapted to utilize off-the-shelf electronic elements that may be constructed by standard assembly techniques, and requires no or few moving parts. Furthermore, the fluid layer design enables the use of readily available plastics and manufacturing techniques. The result is an inexpensive, disposable, and reliable device capable of nucleic acid isolation, amplification, and detection without the need for a dedicated laboratory infrastructure.

Existing nucleic acid testing devices generally use sophisticated heating elements such as deposited film heaters and Peltier devices that add significant cost and/or require specialized manufacturing methods. In embodiments of the invention, heating of the reaction solution is preferably accomplished by use of simple resistive surface-mount devices that may be purchased for pennies or less and are assembled and tested by common manufacturing standards. By layering fluidic chambers over these resistive elements and associated sensor elements, the fluid temperature of the reaction solutions may be conveniently regulated. The broad use of SMD resistors and flexible circuits in the electronics industry ensures that the present invention is amenable to well established quality control methods. In other embodiments of the invention, resistive heating is realized using heating elements formed by patterns fabricated in the conductive layer of a flexible circuit substrate. Many nucleic acid amplification techniques, such as PCR, require not only rapid heating of the reaction solution but rapid cooling as well. Reaction chambers in the present invention are preferably heated on one side and the ambient temperature across the opposite face is used to help reduce fluid temperature. In addition, vertical orientation of embodiments of the device allows for more rapid cooling by passive convection than if the device was oriented horizontally, thus, reducing the thermal cycle period without the use of costly devices such as Peltier devices. In some embodiments of the invention a fan is used to facilitate cooling.

Fluid control is another challenge associated with low-cost nucleic acid test device designs. Devices known in the art generally employ electromechanical, electrokinetic, or piezoelectric pumping mechanisms to manipulate fluids during device operation. These pumping elements increase both device complexity and cost. Similarly, valves making use of elaborate micromechanical designs or moving parts can increase fabrication costs and reduce reliability due to complications such as moving part failure or bio-fouling. Unlike previously described nucleic acid testing devices, embodiments of the present invention utilize hydrostatic pressure under microcontroller control together with capillary forces and surface tension to manipulate fluid volumes. The vertical orientation of some embodiments of the present invention allows for the reaction solution to cascade from chamber to chamber under microcontroller control to accommodate required manipulations of the assay. Fluid may be held in individual reaction chambers through a balance of channel size, hydrostatic pressure and surface tension, where surface tension and hydrostatic pressure prohibits fluid advancement by gas displacement. A sample advances to the lower chamber preferably only after activation of a simple venting mechanism under microcontroller control. Once open, the vent allows fluid to move from a first chamber to a second chamber by means of providing a path for displaced air to escape from the second chamber as fluid enters. Each chamber (or each channel between chambers) within the fluidic component preferably connects to a sealed vent pocket through a narrow vent channel. The vent pocket is preferably sealed on one face with a thin, heat labile plastic membrane or sheet that is easily ruptured by heating a small surface mount resistor underlying, near, or adjacent to the membrane or sheet. Once the vent of a lower chamber is opened, fluid advancement proceeds, even under low hydrostatic pressures.

As more specifically described below, the fluidic or microfluidic vent mechanism used in some embodiments of the present invention preferably employs a heating element in thermal and (optional) physical contact with a heat labile seal to enable electronic control of fluid movement by means of venting a chamber of lower elevation to allow a fluid from a chamber of higher elevation to flow into the lower chamber. In one embodiment, a resistor is mounted on a printed circuit board, using widely used and well-established electronics manufacturing methods, and placed in physical contact with a channel seal comprising a heat labile material. When energized the surface mount resistor generates sufficient heat to rupture the seal, which results in the venting of the chamber to allow equilibration of pressure in the region or chamber where fluid is being moved with the region or chamber where fluid is resident prior to venting. The equilibration of the pressure between the chambers allows the movement of fluid from a chamber of higher elevation to a chamber of lower elevation. A direct seal between higher and lower elevation chambers is preferably not employed. The channel and vent seal may be located remotely from the fluid chambers, thus facilitating fluidic device layout in configurations efficient for manufacture. The seal material may comprise any material that can seal the vent channel and be ruptured from heating as described, for example a thin plastic sheet. This approach to fluid movement control in the apparatus benefits from low materials costs, suitability for manufacture using established manufacturing techniques while providing the capacity to move fluids through a series of chambers under the control of electronic control circuits such as microprocessors or microcontrollers. The use of vents, a heat labile material to seal the vents (and not to seal the fluid chambers or fluid microchannels themselves) and an electronic means of breaking said seal with heat provides a means of controlling fluid flow through the device to enable movement of fluid at predetermined times or following the completion of specific events (for example, attaining a temperature, a temperature change or a series of temperature changes, or the completion of an incubation time or times or other events). In some embodiments, a blockage may be introduced to the channel between chambers when gas phase water must be isolated from a chamber connected by said channel. The blockage may be a soluble material that dissolves upon contact with liquid water following vent opening or a readily melted material such as paraffin that can be removed by the introduction of heat to the site of blockage.

In addition, the vent approach has a number of advantages over sealing the fluid chambers themselves. Vent pockets can be located anywhere on the fluidics layout and simply communicate with the chamber they regulate via a vent channel. From a manufacturing standpoint, vent pockets can be localized so that only a single sealing membrane for all vent pockets (which may comprise a vent pocket manifold) is affixed to the fluidic component, preferably by well established methods such as adhesives, heat lamination, ultrasonic welding, laser welding etc. In contrast, directly sealing a fluid chamber requires that the seal material be placed at different locations corresponding to each chamber location, which is more difficult to manufacture. This presents a more challenging scenario during manufacture compared to a single vent pocket manifold sealed by a single membrane. Additionally, if chambers are directly sealed, melted sealing material can remain in the channels between chambers, occluding flow. The viscosity of the sealing material may require more pressure in the fluid column than is obtained in a miniaturized gravity driven apparatus.

In embodiments of the present invention, reagent mixing requires no more complexity than other systems. Reagents necessary for nucleic acid amplification such as buffers, salts, deoxyribonucleotides, oligonucleotide primers, and enzymes are preferably stably incorporated by use of lyophilized pellets or cakes. These lyophilized reagents, sealed in a fluidic chamber, a recess in a fluidic chamber or a recess in a channel, may be readily solubilized upon contact with aqueous solution. In the case that additional mixing is required, the vertical orientation of embodiments of the present invention offers opportunities for novel methods of mixing solutions. By utilizing heaters underlying fluidic chambers, gas may be heated, delivering bubbles to the reaction solution in the chamber above when the solution contains thermally-sensitive components. Alternatively, heaters may be used to directly heat a solution to the point that boiling occurs, in the case that the solution contains no thermally-sensitive components. The occurrence of air bubbles is often undesirable in previously disclosed fluidic and microfluidic devices, as they may accumulate in fluidic chambers and channels and displace reaction solutions or impede fluid movement within the device. The vertical design of embodiments of the invention presented herein allows bubbles to rise to the fluid surface, resulting in only minimal and transient fluid displacement, effectively ameliorating any disadvantageous impacts of bubbles on the fluidic or microfluidic system. Mixing by boiling is also convenient with this vertical design as fluid displaced during the process simply returns to the original fluidic chamber by gravity after the heating elements are turned off.

In embodiments of the invention, a colorimetric detection strip is used to detect amplified nucleic acids. Lateral flow assays are commonly used in immuno-assay tests due to their ease of use, reliability, and low cost. The prior art contains descriptions of the use of lateral flow strips for the detection of nucleic acids using porous materials as a sample receiving zone which is at or near a labeling zone also comprised of a porous material and placed at or near one end of the lateral flow assay device. In these prior inventions labeling moieties are in the labeling zone. The use of porous materials as the sample receiving zone and the labeling zone results in the retention of some sample solution as well as detection particles in the porous materials. Although labeling zones comprising porous materials having reversibly immobilized moieties required for detection may be used in embodiments of the present invention, embodiments of the present invention preferably utilize detection particles or moieties held in a region of the device distinct from the sample receiving zone of the lateral flow strip and comprising nonporous materials with low fluid retention characteristics. This approach allows nucleic acid target containing samples to be labeled prior to introduction to the porous components of the sample receiving end of the lateral flow component of the device and thereby eliminates the retention and/or loss of sample material and detection particles in a porous labeling zone. This method further enables the use of various treatments of the sample in the presence of detection moieties, such as treatment with high temperatures, to accomplish denaturation of a double-stranded target or secondary structures within a single-stranded target without concern for the impacts of temperature on porous sample receiving or labeling zone materials or the lateral flow detection strip materials. Additionally, the use of a labeling zone not in lateral flow contact with the sample receiving zone but subject to the control of fluidic components such as vents allows target and label to remain in contact for periods of time controlled by fluid flow control systems. Thus embodiments of the present invention can be different than traditional lateral flow test strips wherein sample and detection particle interaction times and conditions are determined by the capillary transport properties of the materials. By incorporating the detection particles in a temperature-regulated chamber, denaturation of duplex nucleic acid is possible allowing for efficient hybridization-based detection. In alternative embodiments, fluorescence is used to detect nucleic acid amplification using a combination of LEDs, photodiodes, and optical filters. These optical detection systems can be used to perform real-time nucleic acid detection and quantification during amplification and endpoint detection after amplification.

Embodiments of the invention comprise a low cost, point-of-use system is provided wherein a nucleic acid sample may be selectively amplified and detected. Further embodiments include integration with a nucleic acid sample preparation device such as that described in International Publication No. WO 2009/137059 A1, entitled "Highly Simplified Lateral Flow-Based Nucleic Acid Sample Preparation and Passive Fluid Flow Control". An embodiment of the device preferably comprises both a plastic fluidic component and a printed circuit assembly (PCA) and/or flexible circuit, and is optionally encased in a housing that protects the active components. Temperature regulation, fluid and reagent mixing are preferably coordinated by a microcontroller. The reaction cassette is preferably oriented and run vertically so that gravity, hydrostatic pressure, capillary forces and surface tension, in conjunction with microcontroller triggered vents, control fluid movement within the device.

In embodiments of the present invention, prepared or crude sample fluid enters a sample port and fills or partially fills a sample cup. Sample may be retained, for varying periods of time, in the sample cup where dried or lyophilized reagents can mix with the sample. Such reagents as positive control reagents, control templates, or chemical reagents beneficial to the performance of the test may be introduced to the sample solution by inclusion in dry, liquid or lyophilized form in the sample cup. Other treatments such as controlled temperature incubations or heat lysis of bacterial or viral analytes may optionally be accomplished in the sample cup my means of an underlying microheater and temperature sensor system interfaced to temperature control electronics. A fluid network comprises the sample port through which sample is introduced to the cassette either manually by the user or via an automated system, e.g. a subsystem integral to the docking unit or a sample processing subsystem; the sample cup wherein sample is held to facilitate accumulation during sample introduction and to add reagents, components to perform treatments required prior to further movement of the sample into the downstream portions of the fluid network (e.g. heat treatment to perform lysis of a bacterial cell or virus); a recirculation vent passage for the equilibration of air, gas or solution pressures of the fluidic channels and/or chambers with the pressure of the expansion chamber of the cassette; a bead recess wherein a reagent bead (e.g. a bead or pellet of material, reagent, chemicals, biological agents, proteins, enzymes or other substances or mixes of these substances) in a dried/desiccated or lyophilized or semidry state may be rehydrated by the sample solution or a buffer solution introduced to the cassette prior to the addition of sample to rehydrate the bead or pellet contained therein and thus comingle the materials therein to the sample solution; a set of one or more vents that can be opened to control fluid movement within the cassette; a first chamber where the sample can be subjected to a regimen of temperatures; an optional barrier within the fluidic channel connecting the first chamber with a second chamber to preclude premature invasion of liquids and/or gases into the second chamber or to temporally control the movement of solution or gases into the second chamber; a second chamber wherein the sample solution may be subjected to further temperature regimens optionally following addition of reagents from an optional reagent bead recess optionally located between first and second chambers; a test strip recess forming a chamber wherein a test strip is mounted to detect an analyte or a reporter molecule or other substance indicative of the presence of an analyte. In some embodiments the cassette is inserted into a docking unit which performs the functions of sealing the cassette, elution, detection, and data transmission. Preferably no user intervention is required once the cassette is inserted into the docking unit, the sample is loaded, and the lid is closed.

Figure 1A:
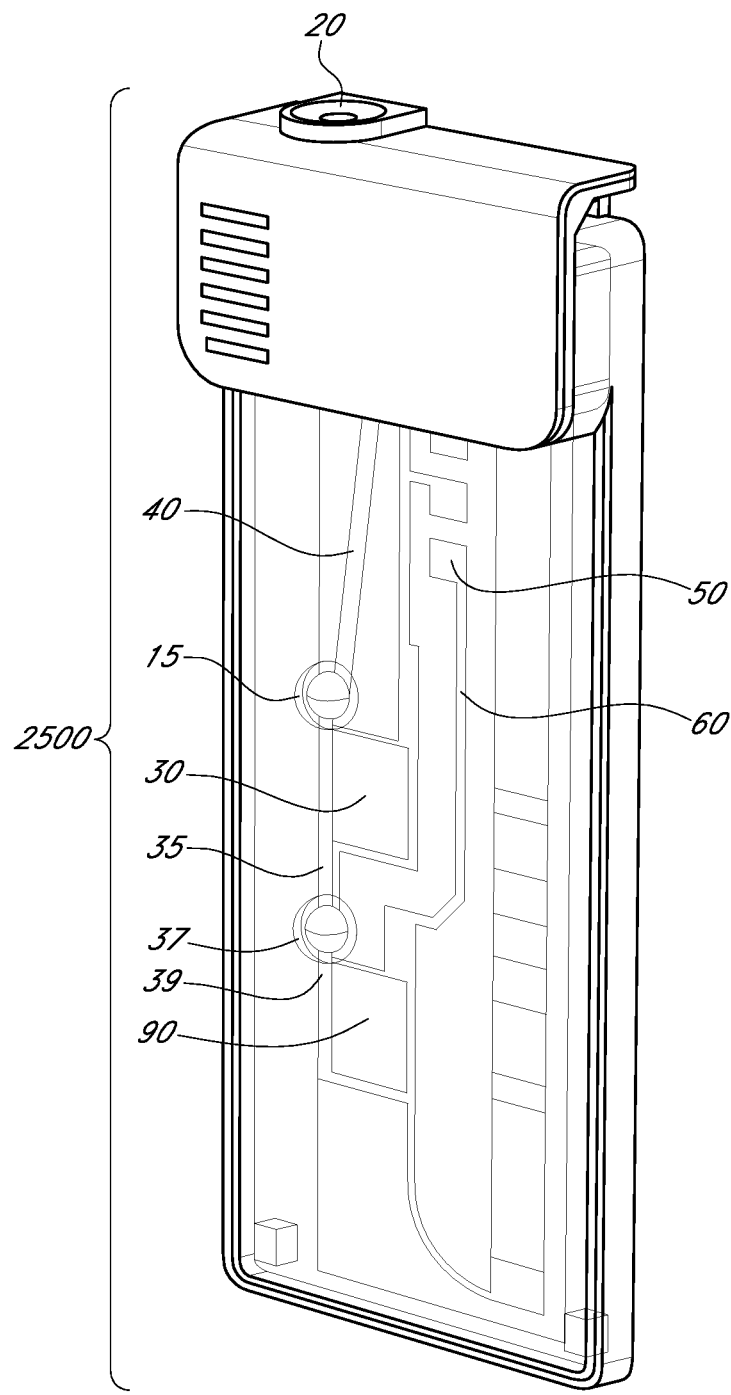
FIG. 1A is a drawing illustrating an embodiment of a test cassette of the present invention.
Figure 1B:
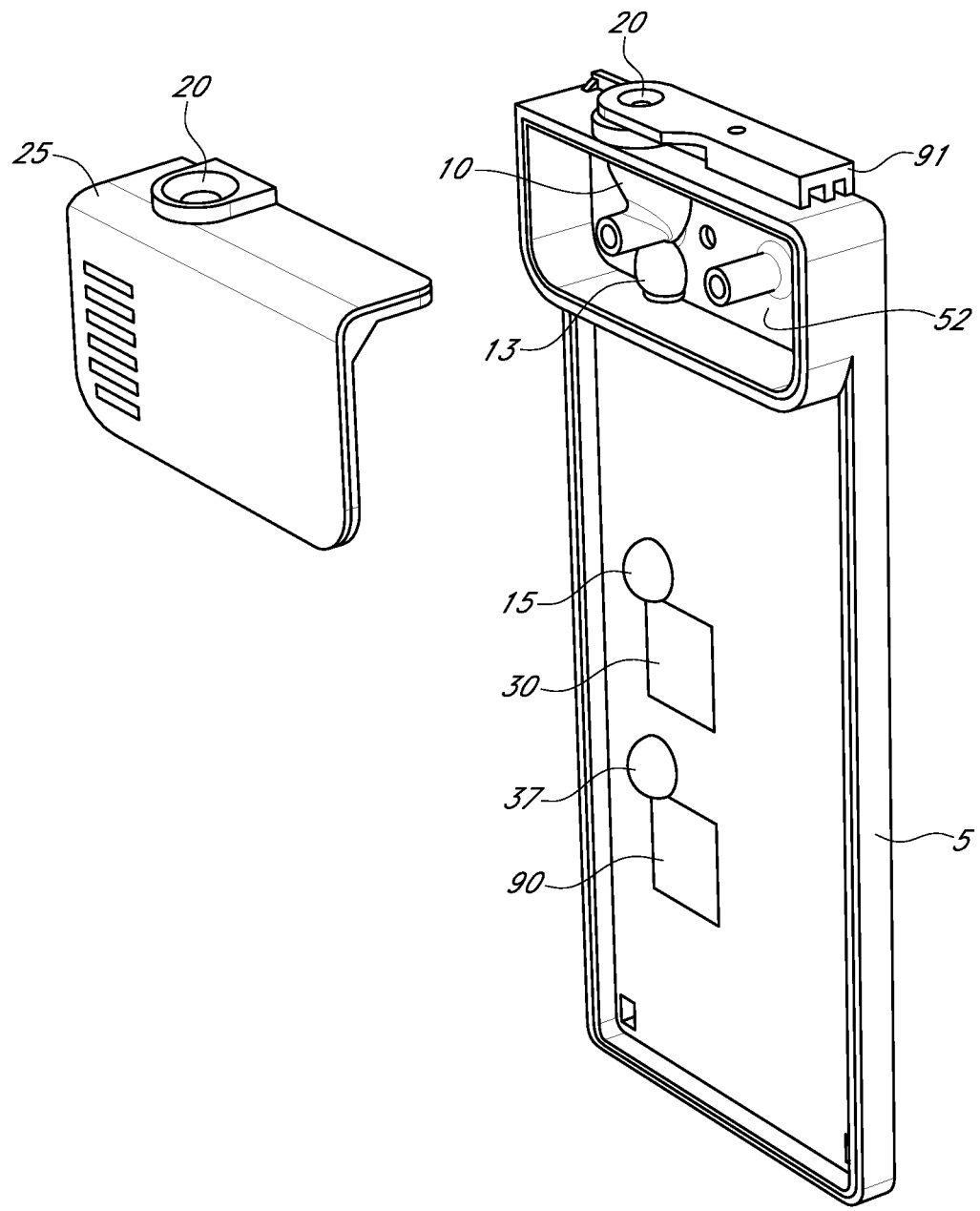
FIG. 1B is an exploded view of one embodiment of the test cassette revealing the sliding seal, sample port, sample cup and internal region of the expansion chamber.

Referring to the representative drawings of cassette 2500 in FIGS. 1-2, a nucleic acid sample is added to the sample cup 10 in fluidic component 5 through the sample port 20. Sliding seal 91 is moved to the closed position by closure of the docking unit lid at the time of assay initiation. Cover 25 holds slide 91 in place in order to seal expansion chamber 52. The nucleic acid sample may derive from an online (i.e. integrated nucleic acid preparation sub-system), a separate nucleic acid preparation process (such as one of many commercially available methods, e.g. spin-columns) followed by addition of the purified nucleic acid to the device by pipette, or an unprocessed nucleic acid containing sample. Already present in the sample cup, or preferably in recess 13 within or adjacent to the sample cup, is reagent mix 16, which may be in liquid or dry form, containing components useful for facilitating cell and virus lysis and/or stabilize liberated nucleic acids. For example, dithiothreitol and/or pH buffering reagents may be employed to stabilize nucleic acids and inhibit RNases. Similarly, reagents to accomplish acid or base mediated lysis may be used. In some embodiments the reagent mix is lyophilized to form lyophilized reagents. In some embodiments a positive control such as a virus, bacteria or nucleic acid is present in the reagent mix. Introduction of the sample to the sample cup causes reagents and samples to commingle such that the reagents act upon the sample. An optional bubble-mixing step to further mix the sample with the reagents or resuspend the reagents may optionally be performed. Fluid is then optionally heated in the sample cup 10 to lyse cells and virus particles. Fluid is then preferably directed through channel 40 to a first chamber 30 that resides below the sample cup when the device is in the vertical orientation. Reagent recess 15 is preferably situated along the inlet channel such that fluid passes through the recess to commingle with dried or lyophilized reagents contained therein prior to entering the first chamber 30. In embodiments wherein the first chamber is a reverse transcription chamber, preferably present in reagent recess 15 are all components necessary of a reverse transcription reaction such as buffering reagents, dNTPs, oligonucleotide primers, and/or enzymes (e.g. reverse transcriptase) in dried or lyophilized form. The reverse transcription chamber is preferably in contact with heater elements to provide a means for the temperature regulation necessary to support the reverse transcription of RNA into cDNA. Channel 35 connects chamber 30 to reagent recess 37. Following cDNA synthesis in chamber 30, vent 50 is opened to allow the reverse transcription reaction to flow via channel 35 into reagent recess 37. Dried or lyophilized reagents present reagent recess 37 commingle with fluid as it passes through the recess to second chamber 90 via inlet 39 such that the reagents act upon the sample in the second chamber, which is preferably an amplification chamber. Preferably present in reagent recess 37 are all components necessary for the amplification reaction, such as buffering agents, salts, dNTPs, rNTPs, oligonucleotide primers, and/or enzymes. In some embodiments the reagent mix is lyophilized to form lyophilized reagents. To facilitate multiplexed tests, wherein multiple amplicons are generated, multiplexed amplification can be accomplished by deposition of multiple primer sets within the amplification chamber(s) or preferably within reagent recesses upstream of said amplification chamber(s). Additionally, circuit board and fluidic designs in which multiple amplification and detection chambers are incorporated into the device support multiple parallel amplification reactions that may be single-plex or multiplex reactions. This approach reduces or eliminates the complications known to those skilled in the art that result from multiplexed amplification using multiple pairs of primers in the same reaction. Moreover, the use of multiple amplification reaction chambers allows simultaneous amplification under different temperature regimens to accommodate requirements for optimal amplification, such as different melting or annealing temperatures required for different target and/or primer sequences.

Following nucleic acid amplification, vent pocket 150 is opened to allow the amplification reaction product to flow via channel 135 into chamber 230. Detection strip 235 situated in chamber 230 enables the detection of target nucleic acids labeled by detection particles located on a region of detection strip 235 or optionally in capillary pool 93.

Figure 2A:
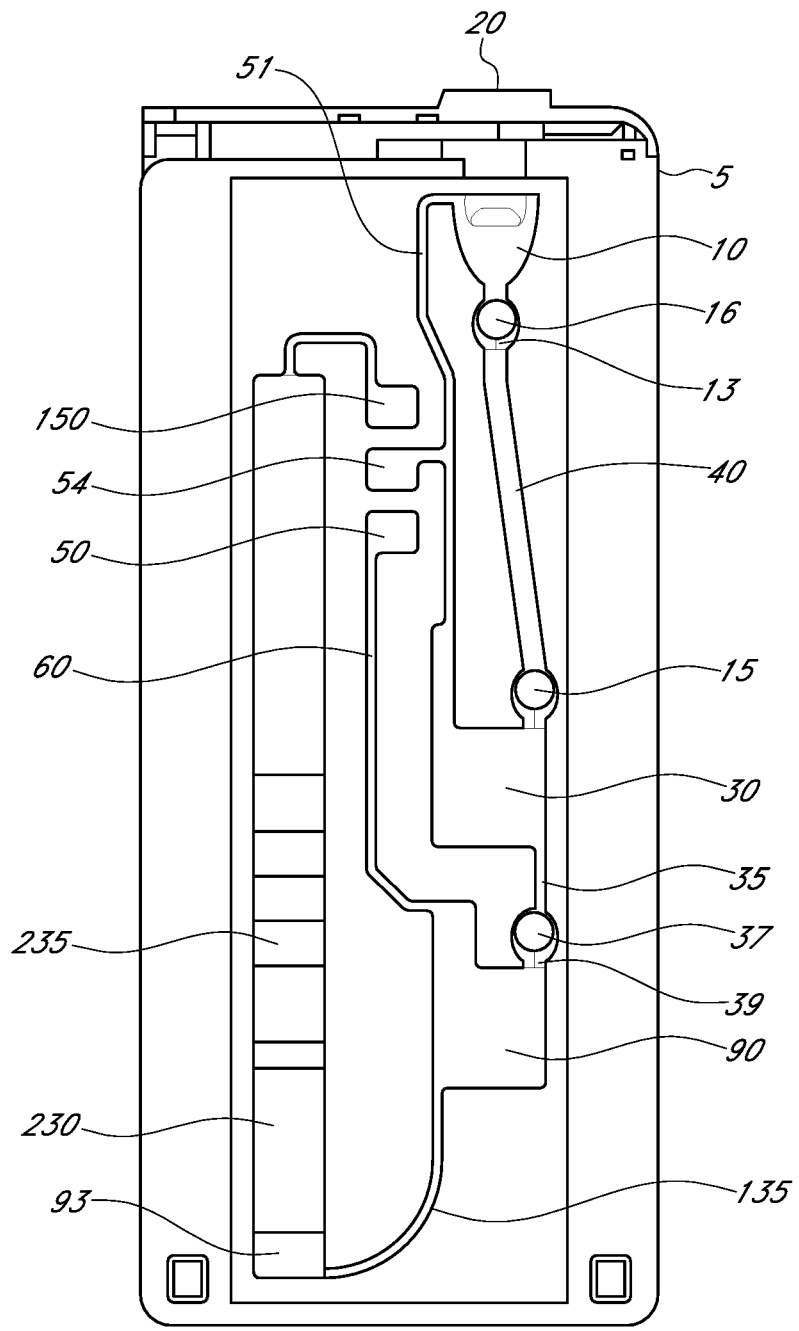
FIG. 2A is a representation of the fluidic network in one embodiment of a test cassette of the invention.
Figure 2B:
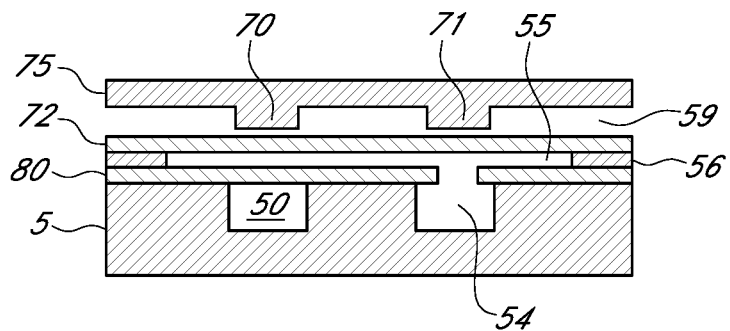
FIGS. 2B-2C are schematic representations prior to and after vent opening, respectively, of how a heat triggered vent can be employed to vent to an expansion chamber to accomplish fluid flow control in the context of a hermetically sealed test cassette.
Figure 2C:
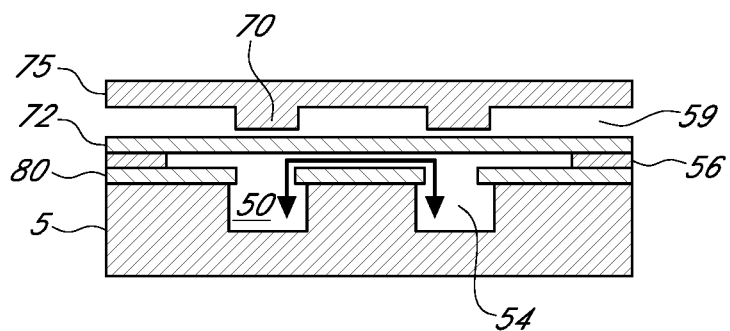
Figure 2D:
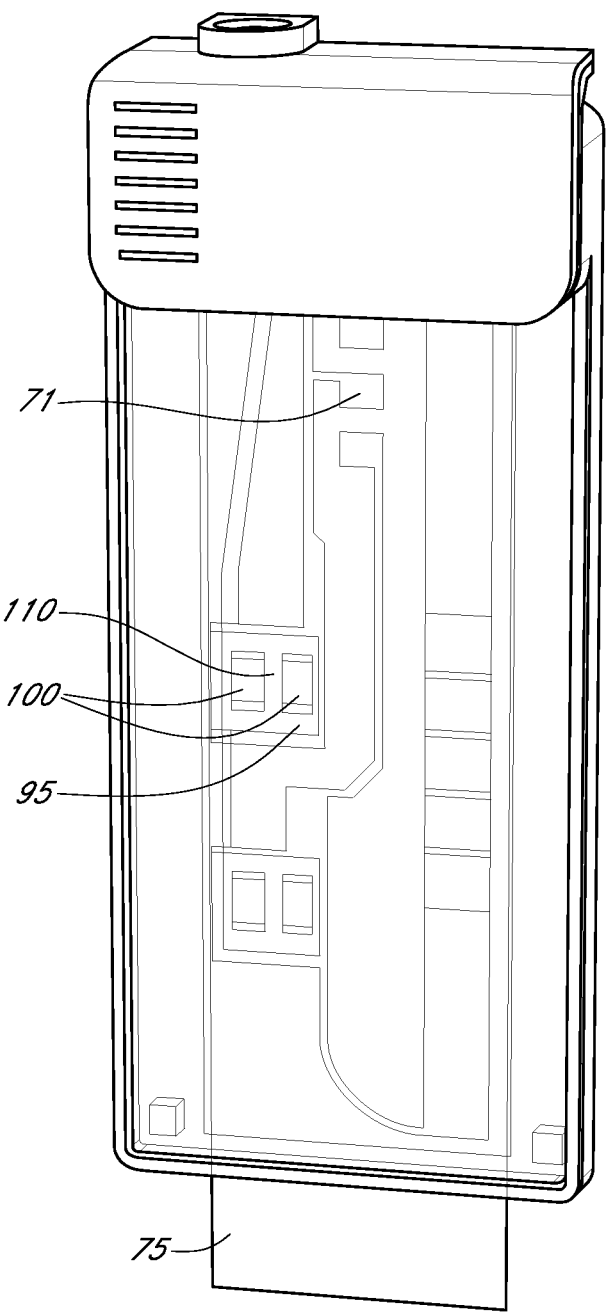
FIG. 2D is a drawing of one embodiment of a disposable test cassette showing the placement of the printed circuit assembly (PCA) comprising resistive heating elements and temperature sensors.
Figure 2E:
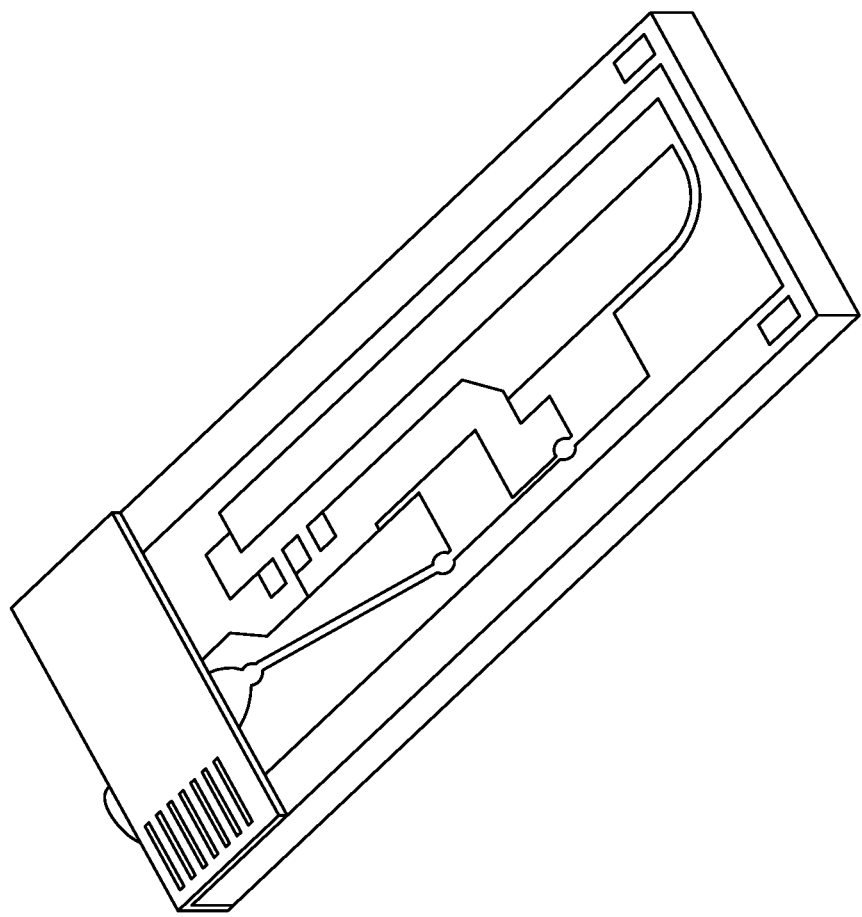
FIG. 2E is a photograph of an injection molded plastic test cassette that includes the features described in FIG. 2A.

Fluid movement from the sample cup 10 to first chamber 30 occurs because chamber 30 is vented to expansion chamber 52 via opening 51. Fluid movement from the first chamber to the second chamber of the device is preferably accomplished by the opening of a vent connected to the second chamber. When fluid enters first chamber 30, vent pocket 50, connected to the downstream chamber, is sealed, and thus fluid will not pass through channel 35 connecting the two chambers. Referring now to FIG. 2A, movement of fluid from chamber 30 to chamber 90 can be accomplished by allowing air within chamber 90 to communicate with air in expansion chamber 52 by rupturing a seal overlying vent pocket 50. Rupture of the seal at vent pocket 50 allows communication of air in chamber 90 via vent channel 60 with air in expansion chamber 52, which is connected via opening 51 to vent pocket 54. The seal at vent pocket 54 is preferably open, or was previously ruptured, as shown in FIG. 2B. As shown in FIG. 2C, rupture of the seal of vent pocket 50 allows vent pocket 50 (and thus chamber 90) to communicate with vent pocket 54 (and thus expansion chamber 52). This method of fluid movement is preferably embodied within a hermetically sealed space to contain bio-hazardous samples and amplified nucleic acids within the test cassette. To enable a hermetically sealed cassette, selectively heat resistant and heat labile materials are layered in the manner represented schematically in cross section in FIGS. 2B-2C. Referring now to FIGS. 2B-2C, heat source 70, which preferably comprises a resistor, on printed circuit board or PCA 75 is placed in register with vent pockets 50, 54 and in proximity to heat labile vent pocket seal material 80. The vent pocket seal may comprise a heat labile material such as polyolefin or polystyrene. A heat stable material (such as polyimide) 72 is preferably disposed between heat source 70 and heat labile vent pocket seal material 80 to form a hermetic barrier. In some embodiments the sealed space 55 between or surrounding vent pockets is augmented by the inclusion of an optional gasket or spacer 56 comprising an adhesive layer that bonds heat stable material 72 to heat labile material 80 and/or fluidic component 5 and maintains a hermetic seal of the test cassette in the region of the vents after one or more of the vents are opened, while preferably also providing an air gap for the communication of air between opened vents and/or the optional expansion chamber. In this embodiment, heat is transferred from heat source 70 through heat stable material 72 and sealed space 55 to the heat labile vent pocket seal material 80, rupturing it and opening vent pocket 50. A microcontroller is preferably responsible for sending electrical current to heat source 70. Vent pocket 50 preferably opens to an enclosed space such that the gas within the test cassette may remain sealed with respect to the environment outside of the test cassette. The enclosed space may comprise the air within the test cassette, optionally including a vacant air chamber to allow for gas expansion, such as an expansion chamber. As shown in FIG. 2C, opening of vent pocket 50 results in the communication of gases in the vented fluid chamber with the gas of the expansion chamber, since vent pocket 54 was previously ruptured by heat source 71, and vent pocket 54 is in gaseous communication with the expansion chamber. The resulting reduced pressure in the vented fluid chamber allows fluid to flow by gravity into the vented chamber from a chamber situated above. Other embodiments of the vent pocket may comprise seals other than a heat-sensitive membrane, and may utilize other methods of breaking the seals, such as puncturing, tearing, or dissolving. A photograph of such a cassette is shown in FIG. 2E.

Figure 45:
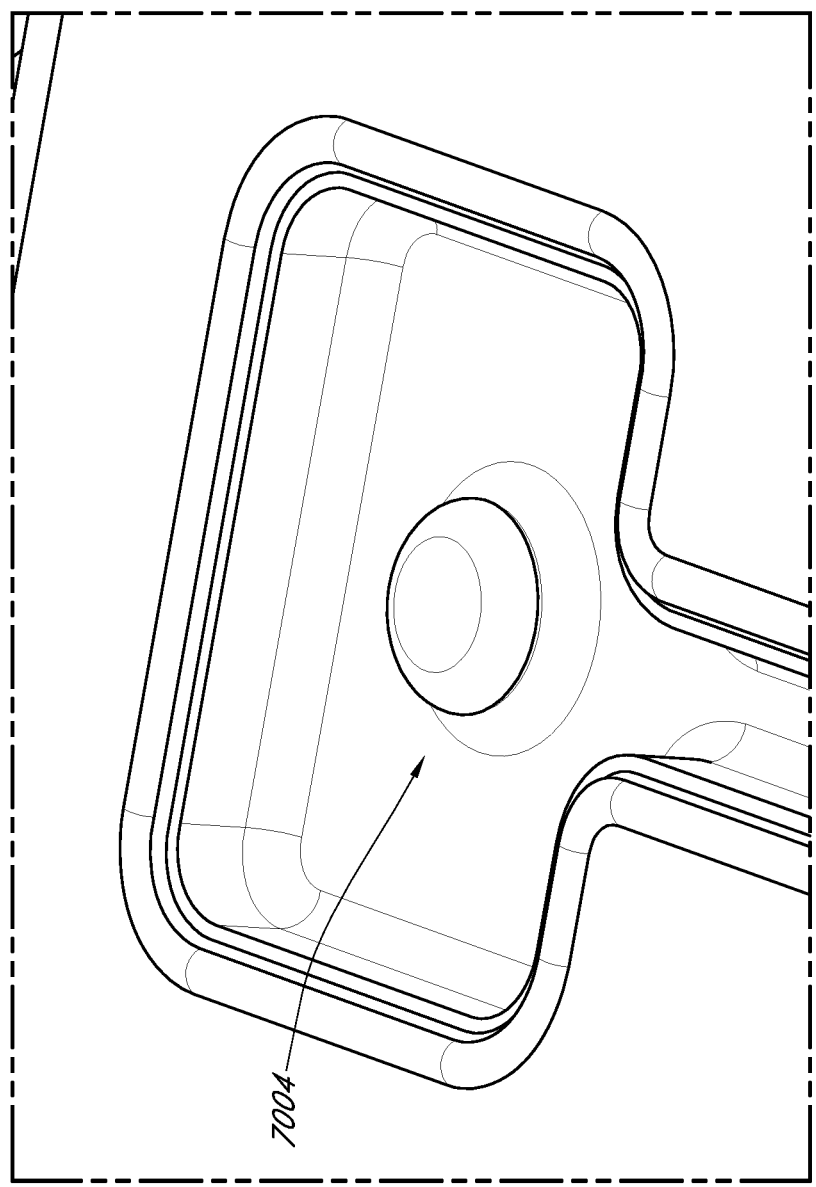
FIG. 45 shows an embodiment of a vent pocket of the present invention comprising a dimple structure.

The face opposite the open face of the vent pocket may optionally comprise a dimple, protrusion, asperity, or other similar structure, such as dimple 7004 of FIG. 45, to facilitate the formation of an opening during rupture of the vent seal material. Such a structure also preferably prevents resealing of the vent after rupture of the seal. This can occur in embodiments comprising a circuit board with surface mount components. In such embodiments the surface mount resistors can stretch the polyimide film, pushing it into the opening in the gasket and against the heat labile material. Once the seal ruptures, the molten seal material can form a secondary seal with that polyimide, thereby closing the vent. In embodiments with a flex circuit comprising metallic traces forming heating elements, the heater can cause the polyimide flex circuit to deform locally, often forming a protrusion (often comprising the heater material) extending into the opening in the gasket, possibly occluding the vent opening due to the molten seal material. Dimple 7004 can help prevent these occurrences.

Figure 3A:
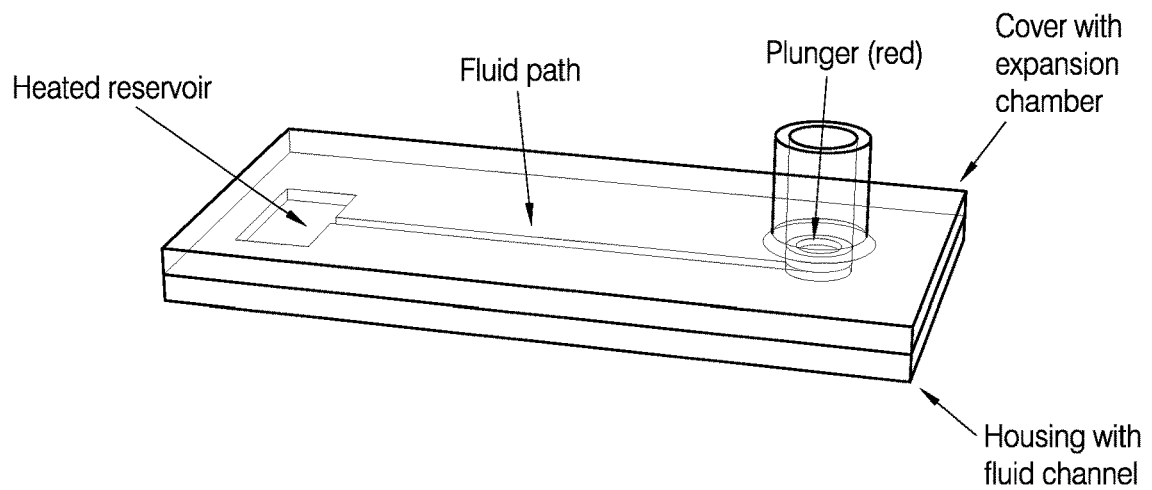
FIG. 3A is a representation of the operating principle of an embodiment of the expansion chamber.
Figure 3B:
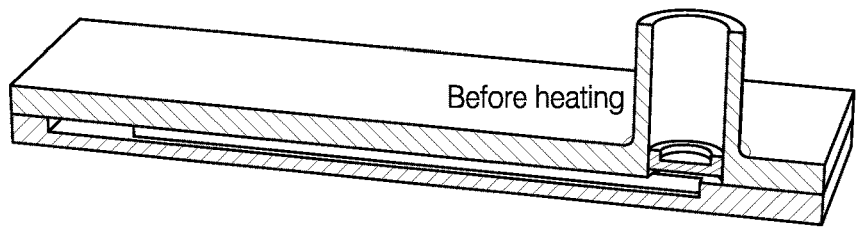
FIG. 3B is a cross-section of the piston-based expansion chamber prior to gas expansion within the test cassette.
Figure 3C:
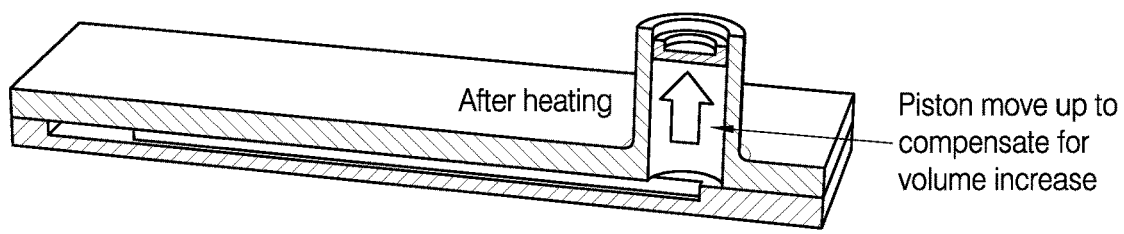
FIG. 3C is a cross-section of the piston-based expansion chamber after gas expansion within the test cassette.
Figure 4A:
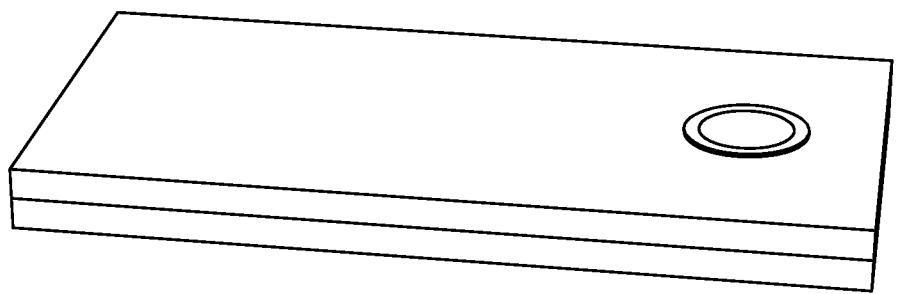
FIG. 4A is an illustration of an approach to forming an expansion chamber wherein an expandable bladder is employed to provide an expanding internal volume.
Figure 4B:
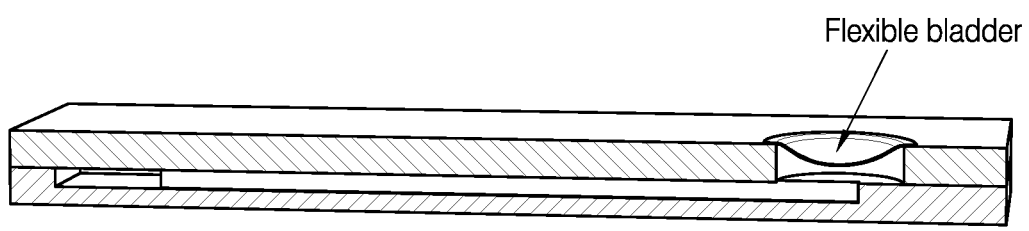
FIG. 4B is a cross-section of the bladder-based expansion chamber prior to gas expansion within the test cassette.
Figure 4C:
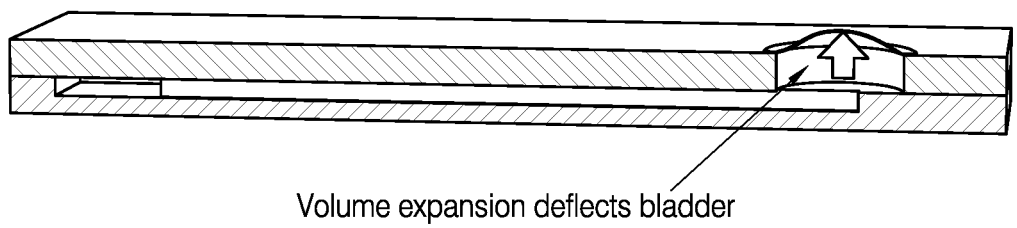
FIG. 4C is a cross-section of the bladder-based expansion chamber after gas expansion within the test cassette.
Figure 5A:
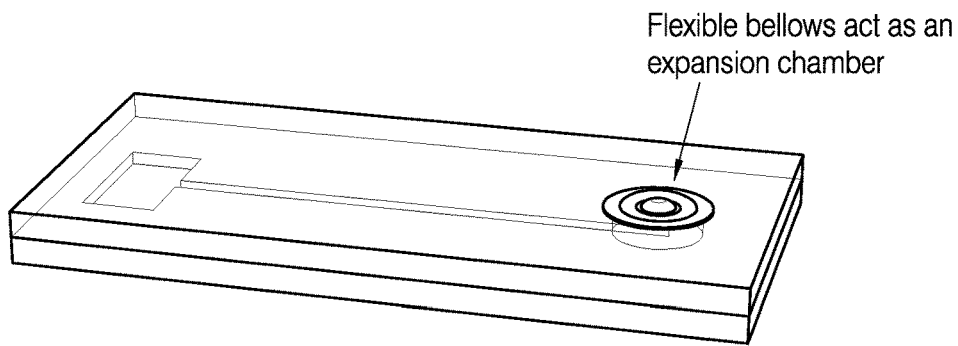
FIG. 5A is an illustration of an approach to forming an expansion chamber wherein an expandable bellows is employed to provide an expanding internal volume.
Figure 5B:
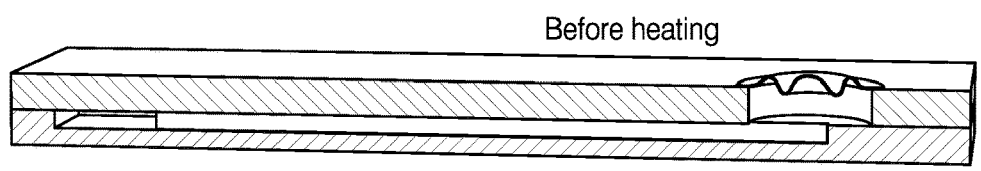
FIG. 5B is a cross-section of the bellows-based expansion chamber prior to gas expansion within the test cassette.
Figure 5C:
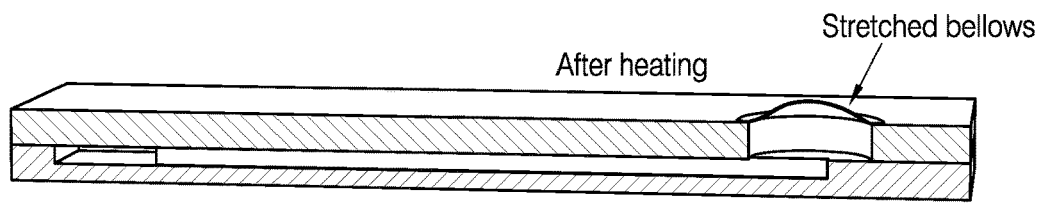
FIG. 5C is a cross-section of the bellows-based expansion chamber after gas expansion within the test cassette.
Figure 6A:
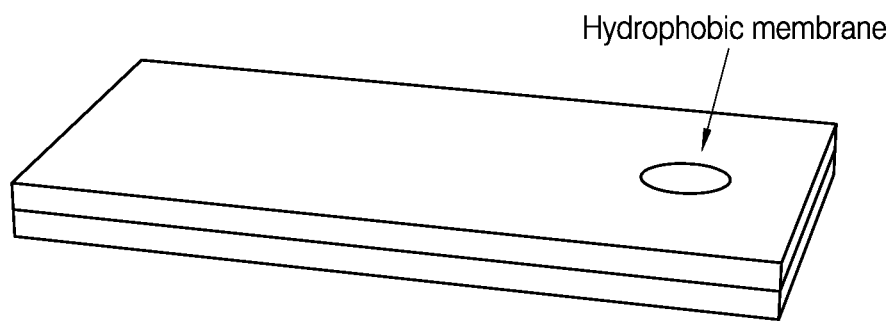
FIG. 6A illustrates the use of a semi-permeable barrier, membrane or material that allows gas to pass freely while particles such as bacteria, viruses, or large molecules such as DNA or RNA are retained within the device.
Figure 6B:
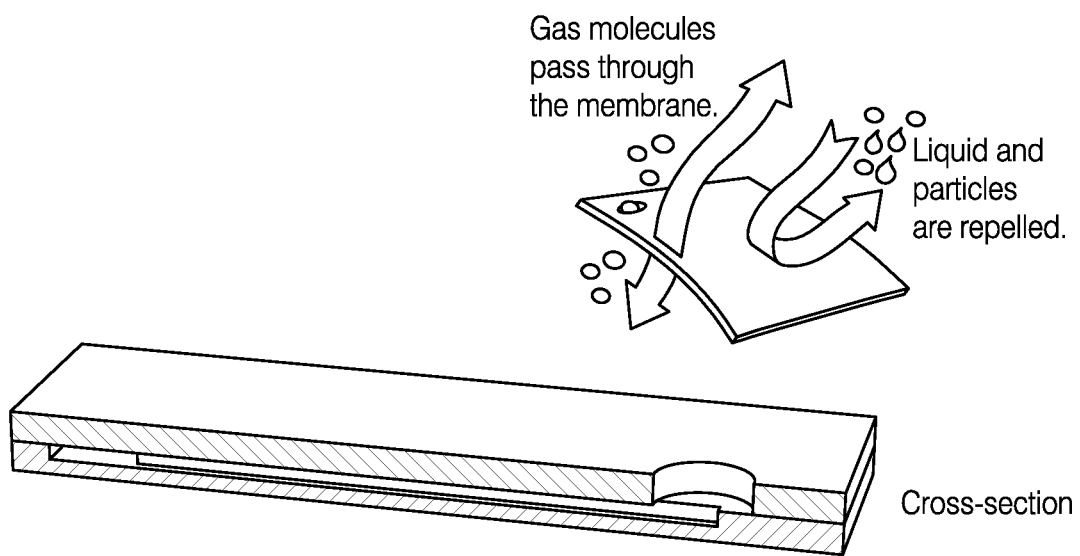
FIG. 6B is a cross-section of the semi-permeable barrier employed in lieu of an expansion chamber to equalize internal pressures with ambient pressures or to reduce internal pressure.

Sealed space 55 optionally provides a conduit to other vents, vent pockets or chambers (such as expansion chamber 52). Following vent opening, fluidic component 5 remains sealed from the external environment 59. Expansion chamber 52 preferably accommodates gas expansion during heating by buffering the air/water vapor volume either by providing a sufficiently large volume so that gas expansion from temperature changes does not significantly impact the pressure of the system, or by accommodating gas expansion by displacement of a piston (FIG. 3), a flexible bladder (FIG. 4), a bellows (FIG. 5), or a hydrophobic barrier that allows gas but not macromolecules to pass free across the barrier (FIG. 6). In FIG. 3 the expansion chamber makes use of a piston that is displaced by increasing pressure within the sealed fluidic system. The expansion chamber serves to reduce or eliminate the accumulation of pressure within the sealed system. Displacement of the piston occurs in response to increased pressure within a hermetically sealed test cassette, reducing internal pressure within the test cassette resulting from such processes as gas expansion during heating. In FIG. 4, deflection of the bladder occurs in response to increased pressure within a hermetically sealed test cassette. Displacement of the bladder reduces internal pressure within the test cassette resulting from such processes as gas expansion during heating. In FIG. 5, stretching of the bellows occurs in response to increased pressure within a hermetically sealed test cassette. Stretching of the bellows reduces internal pressure within the test cassette resulting from such processes as gas expansion during heating.

Figure 7:
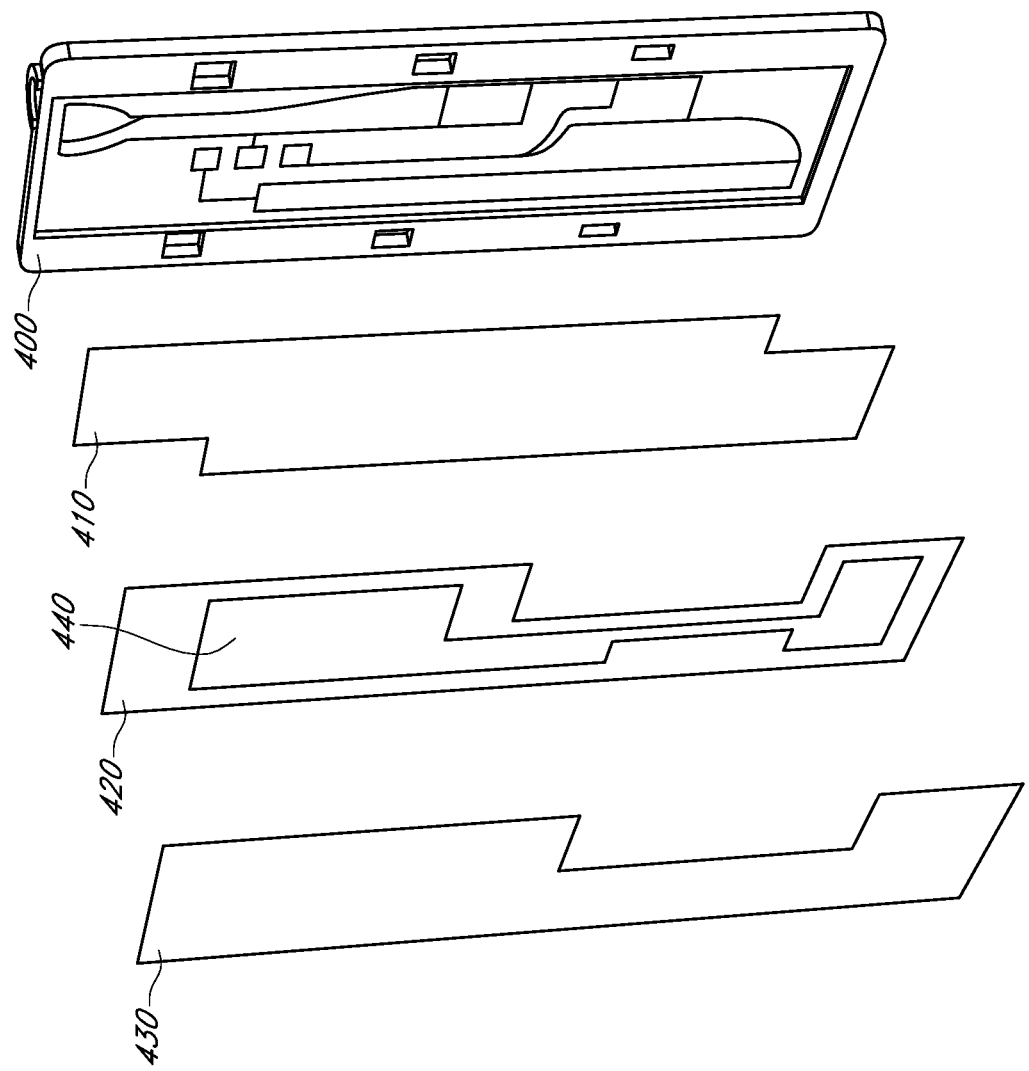
FIG. 7 is an exploded view of a test cassette design wherein an expansion chamber is created by a spacer between a layer of biaxially oriented polystyrene (BOPS) film.
Figure 8A:
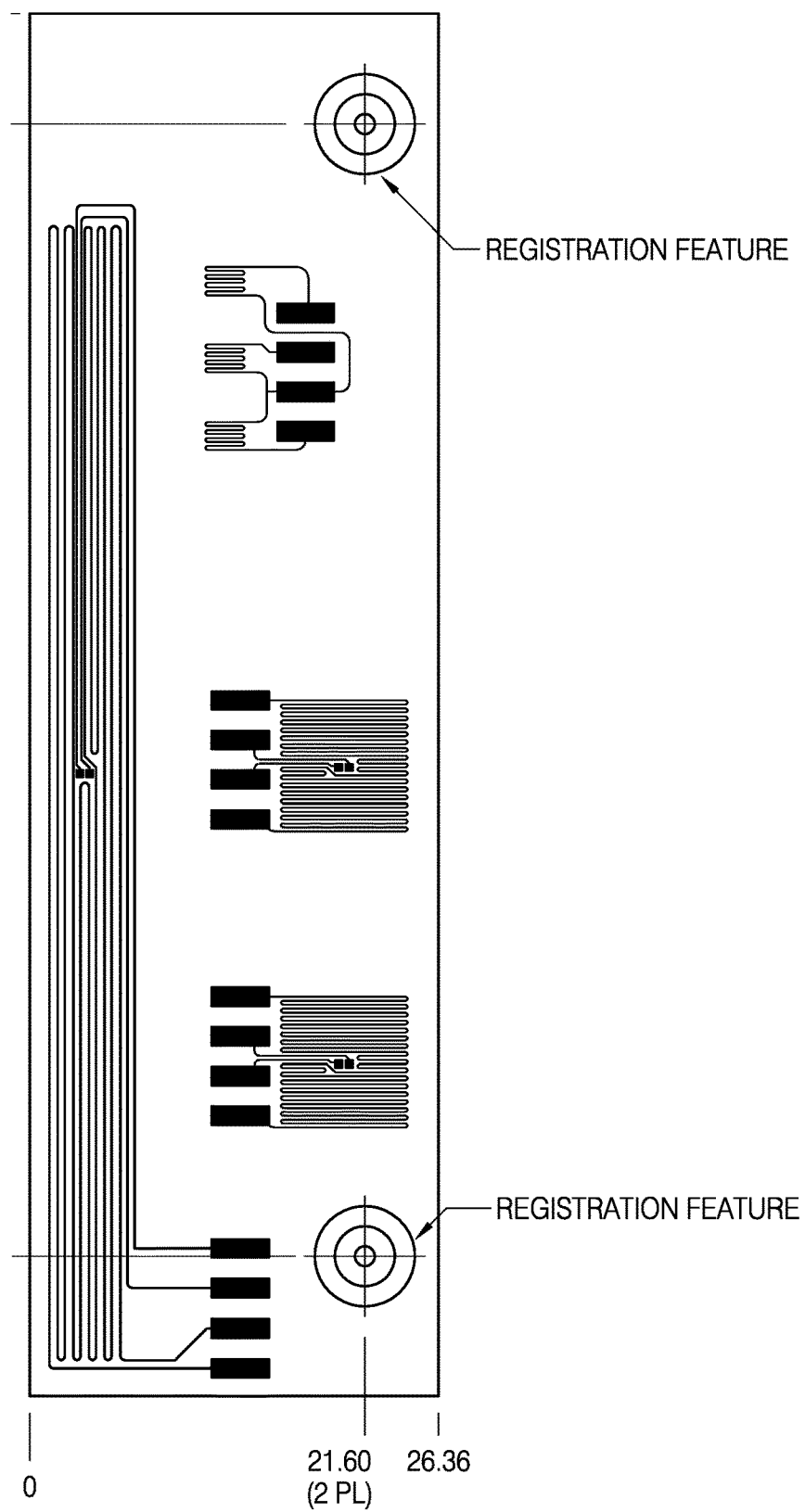
FIG. 8A is a drawing of an embodiment of a flexible circuit comprising resistive heating elements for two fluid chambers, a detection strip chamber and three vents and electrical contact pads.
Figure 8B:
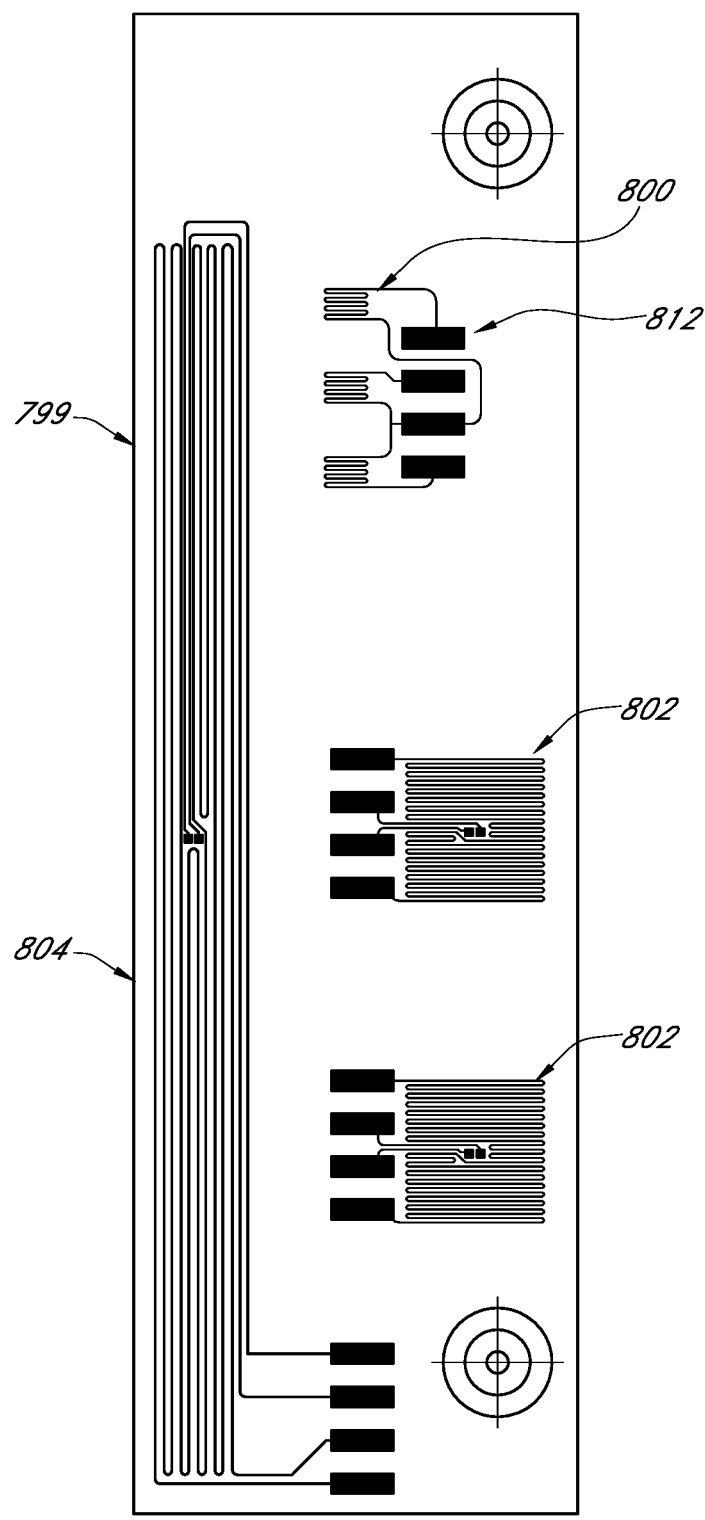
FIG. 8B is an embodiment of a flexible circuit comprising resistive heating elements for two fluid chambers, a detection strip chamber and three vents and electrical contact pads for energizing the resistive heating elements.
Figure 8C:
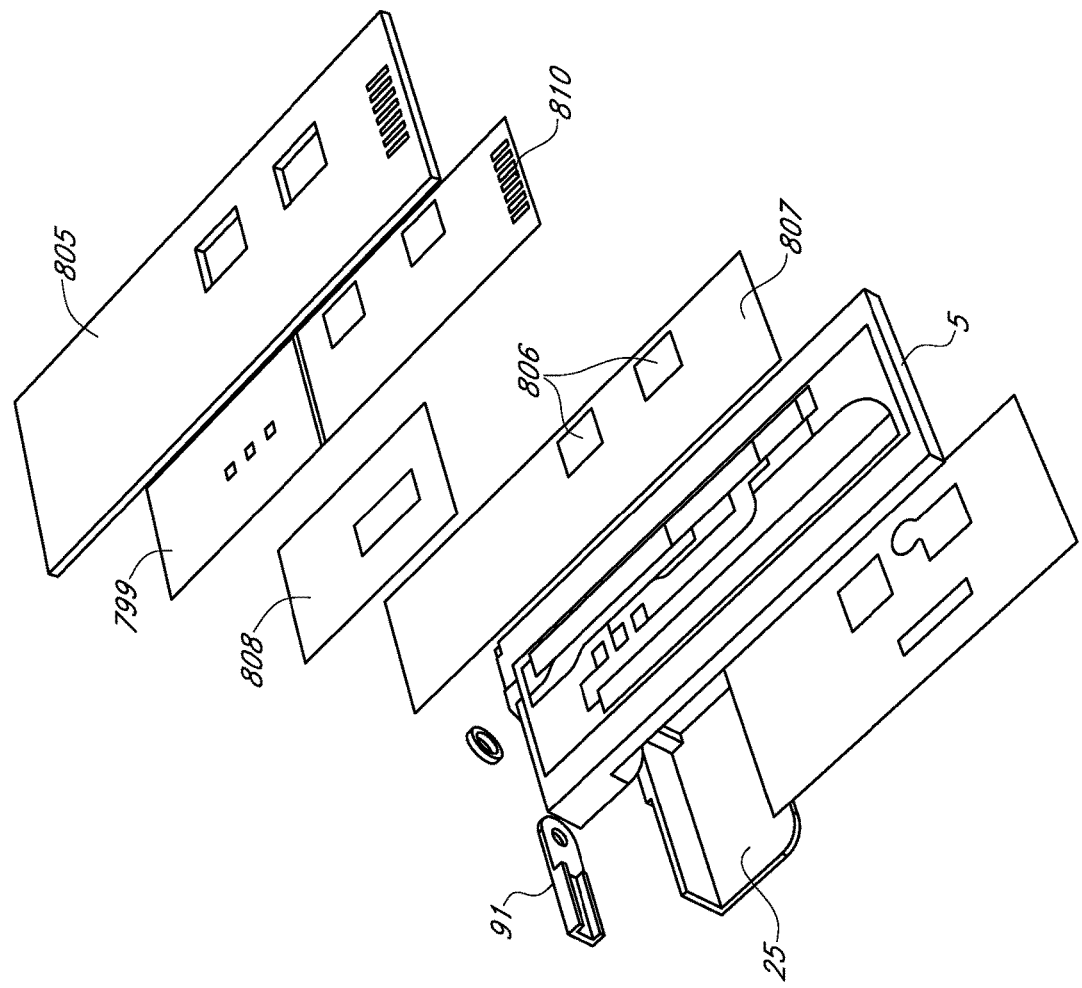
FIG. 8C is an exploded view of an embodiment of a test cassette.
Figure 8D:
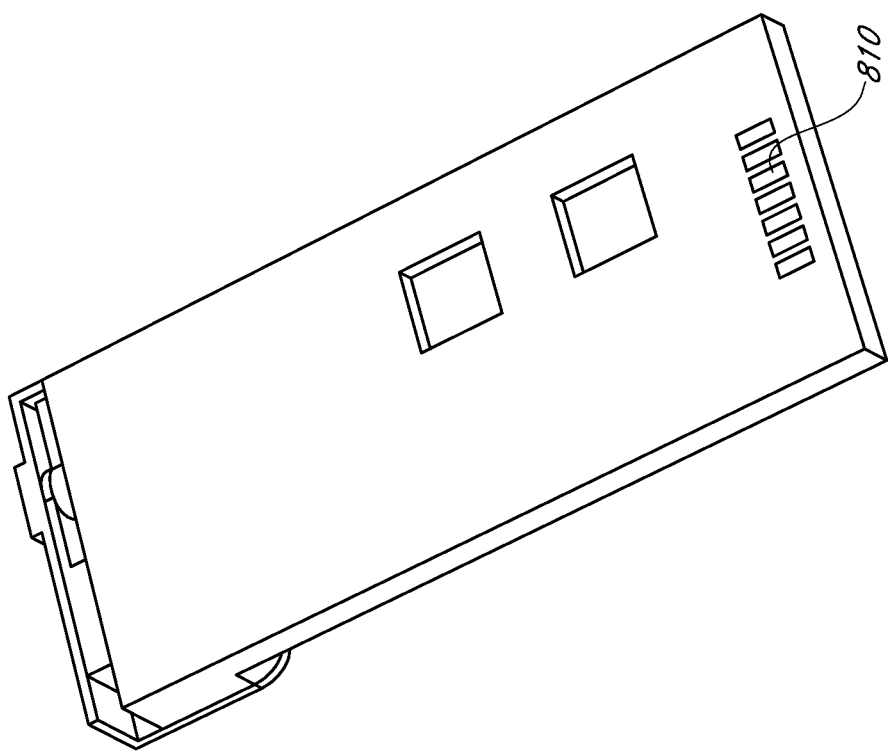
FIG. 8D is a view of the assembled test cassette of FIG. 8C.

Expansion chambers may be incorporated as a vacant air volume, such as the included volume shown in expansion chamber 52 at the top of the test cassette illustrated in FIG. 1. As illustrated in FIG. 7, to facilitate the fabrication of a cassette of minimum thickness, expansion chambers may also be incorporated into air gap 440 formed by a suitably designed gasket 420 when sealed to heat labile material 410 and heat stable material 430 to form the backing of fluidic component 400. Minimization of test cassette physical dimensions is desirable to reduce shipping costs, reduce thermal mass and provide an aesthetically pleasing and convenient design. In addition to forming air volume for gas expansion, gasket 420 generates a space between the heat stable material 430 and heat labile material 410 to facilitate free movement of air through open vents while maintaining a sealed system to prevent exposure to the environment. Gasket 420 is preferably thick enough to provide a sufficient air gap to equilibrate pressures between open vents, but is also sufficiently thin to not substantially impact the interface between the heaters and the corresponding vent pockets or the sealing of the cassette by the heat stable material. In embodiments of the present invention which comprise a flex circuit, the flex circuit may comprise a heat stable material such as polyimide, in which case the separate sheet of heat stable material 430 is not required, for example as shown in FIG. 8C. The use of an expansion chamber to reduce or equilibrate pressure within the sealed test cassette ensures that pressure disequilibria do not result in unfavorable or premature solution movements within the test cassette and that pressure accumulation does not adversely impact desired fluid movement, such as movement between chambers or through channels. This pressure control, i.e. the establishment of designated pressure distributions throughout the device, enables the system to work as designed regardless of atmospheric pressure. The expansion chamber therefore enables controlled fluid movements which are dependent upon stable pressure within the system to be employed, and also enables use of a hermetically sealed test cassette, thereby avoiding the disadvantages of the venting the test cassette to atmosphere, for example the potential release of amplicon to the atmosphere. Furthermore, the method of enabling fluid flow by reducing pressure downstream of a fluid, such as by opening a vent to the expansion chamber, eliminates the need for pumps, such as those that create a positive pressure upstream of the fluid, or other devices with moving parts. Similar advantages are possible by venting an area downstream of a fluid to a relatively larger reservoir (such as the expansion chamber) at substantially the same pressure as the downstream area, thereby enabling the fluid to flow under the force of gravity (provided the device is in the appropriate orientation). The size of the expansion chamber is preferably sufficiently large to accommodate reaction vapors produced during the assay without increasing the pressure of the system to a point where it overcomes the capillary force or gravitational force necessary for the fluid to flow.

In embodiments where the second chamber is an amplification chamber, the chamber is preferably in contact with heater elements to provide a means for the temperature regulation necessary to support nucleic acid amplification. In some embodiments of the invention, the amplification chamber may contain oligonucleotides on at least a portion of the interior surface. At the interface between wall 95 of chamber 30 and one or more heating elements 100, as illustrated in FIG. 2D, it may be advantageous to place a thermally conductive material such as a thermal grease or compound. A microcontroller preferably modulates current to the resistive heating element(s), preferably by means of metal oxide semiconductor field effect transistors (MOSFETs), based upon data collected from temperature sensor 110 on PCA 75, using simple on/off or proportional integral derivative (PID) temperature control methods or other algorithmic temperature control known to those skilled in the art.

Placing the heating elements, and in some embodiments the corresponding temperature sensor(s), on the disposable component enables the manufacture of highly reproducible thermal coupling between the temperature control subsystem and the amplification and detection chambers to which they interface. This approach enables a highly reliable means of coupling the fluidic subsystem to the electronic thermal control subsystem by forming the thermally conductive interface during manufacture. The resulting superior thermal contact between the electronic temperature control components and the fluidic subsystem results in rapid temperature equilibration, and therefore rapid assays. The use of a flexible circuit to provide disposable resistive heating elements that are fused to the rear of the fluidic component backing either directly or with an intervening gasket, allows for a low cost means of attaining excellent thermal contact, rapid temperature cycling and reproducible manufacture. Resistive heating elements for reverse transcription, amplification and fluid flow vent control can be formed directly on the flex circuit by etching the conductive layer of the flex circuit to form geometries exhibiting the required resistance. This approach eliminates the need for additional electronic components and simplifies manufacture while reducing cost.

In an embodiment of the present invention, flexible circuit 799 for resistive heating and vent opening is shown in FIG. 8. The use of a flexible heater as a component of disposable cassette allows the cassette backing to be configured to enable fluid in the heated fluid chambers to make direct contact with the material comprising the flexible heater circuit. For example, as shown in FIG. 8C, windows 806 in thermally labile material 807 (which preferably comprises BOPS) that forms the rear of the cassette may be situated over the fluid chambers to allow direct contact of fluid with flexible circuit 799. Direct contact between the flexible circuit layer and the fluid to be temperature controlled by heaters on the flexible circuit provides for a low thermal mass system capable of rapid temperature changes. To enable collection of temperature data for use in temperature regulation a temperature sensor may be optionally incorporated into the flexible circuit, and/or a non-contact means of temperature monitoring such as an infrared sensor may be employed. Resistive heating elements, such as heating element 800, in a flexible circuit can be utilized for vent rupture when they are situated in register with a vent pocket. Electrical pads 812 provide current to heating elements 800. Similarly, the flexible circuit or circuits may comprise resistive heating elements 802 and 803 for heating the fluid chambers, and optional resistive heating element 804 for regulating the temperature of the detection strip.

In this embodiment flexible circuit 799 also preferably serves as a heat stable seal to maintain a hermetically sealed cassette, similar to heat stable material 72 described above. Optionally an additional heat stable layer (for example comprising polyimide) can be placed between flexible circuit 799 and rear housing or panel 805. A spacer or gasket 808 is preferably placed around vent resistors 800 between thermally labile material 807 and flexible circuit 799 to ensure free air movement through open vents while maintaining a sealed cassette. Rear housing or panel 805 preferably comprises thin plastic and is preferably placed over the exposed surface of the flexible circuit to protect it during handling. Rear housing or panel 805 may comprise windows over the heater elements on flexible circuit 799 to facilitate cooling and temperature monitoring. Electrical contact with controlling electronics of the docking unit (described below) may optionally be provided by a set of electrical pads 810, preferably comprising an edge connector or connector pins such as spring loaded pins.

Embodiments of the test cassette chambers preferably comprise materials capable of withstanding repeated heating and cooling to temperatures in the range of approximately 30° C. to approximately 110° C. Even more preferably, the chambers comprise materials capable of withstanding repeated heating and cooling to temperatures in the range of approximately 30° C. to approximately 110° C. at a rate of temperature change on the order of approximately 10° C. to approximately 50° C. per second. The chambers are preferably capable of maintaining solutions therein at temperatures suitable for heat mediated lysis and biochemical reactions such as reverse transcription, thermal cycling or isothermal amplification protocols, preferably controlled by programming of the microcontroller. In some nucleic acid amplification applications, it is desirable to provide an initial incubation at an elevated temperature, for example a temperature between approximately 37° C. and approximately 110° C. for a period of 1 second to 5 minutes, to denature the target nucleic acid and/or to activate a hot start polymerase. Subsequently, the reaction solution is held at the amplification temperature in the amplification chamber for isothermal amplification or, for thermocycling-based amplification, is varied in temperature between at least two temperatures including, but not limited to, a temperature that results in nucleic acid duplex denaturation and a temperature suitable to primer annealing by hybridization to the target and extension of the primer through polymerase catalyzed nucleic acid polymerization. The duration of incubations at each requisite temperature in a thermal cycling regimen may vary with the sequence composition of the target nucleic acid and the composition of the reaction mix, but is preferably between approximately 0.1 seconds and approximately 20 seconds. Repeated heating and cooling is typically performed for approximately 20 cycles to approximately 50 cycles. In embodiments involving isothermal amplification methods, the temperature of the reaction solution is maintained at a constant temperature (in some cases following an initial incubation at an elevated temperature) for between approximately 3 minutes and approximately 90 minutes depending on the amplification technique used. Once the amplification reaction is complete, the amplification reaction solution is transported, by opening the vent that is in communication with a chamber below the chamber employed for amplification, to the lower chamber to accomplish further manipulations of the amplified nucleic acids. In some embodiments of the invention manipulations comprise denaturation of the amplified nucleic acids and hybridization to detection oligonucleotides conjugated to detection particles. In some embodiments of the invention, amplified nucleic acids are hybridized to detection oligonucleotides conjugated to detection particles and to capture probes immobilized on a detection strip.

In some embodiments, additional biochemical reactions may be conducted in the amplification chamber prior to, during, or after the amplification reaction. Such processes may include but are not limited to reverse transcription wherein RNA is transcribed into cDNA, multiplexing wherein multiple primer pairs simultaneously amplify multiple target nucleic acids, and real time amplification wherein amplification products are detected during the amplification reaction process. In the case of the latter, the amplification chamber may not contain a valve or outlet channel, and the amplification chamber would preferably comprise an optical window or otherwise configured to enable interrogation of amplicon concentration during the amplification reaction process. In one real-time amplification embodiment, either fluorescently labeled oligonucleotides complementary to the target nucleic acid or fluorescent dyes specific for duplex DNA are monitored for fluorescence intensity by means of an excitation light source such as LEDs or diode laser(s) and a detector such as a photodiode, and appropriate optical components including but not limited to optical filters.

Detection

Embodiments of the detection chamber 230 preferably provide for the specific labeling of amplified target nucleic acids generated in the amplification chamber. As shown in FIG. 2A, detection chamber 230 preferably comprises a capillary pool or space 93 and a detection strip 235. Detection particles comprising dye polystyrene microspheres, latex, colloidal gold, colloidal cellulose, nanogold, or semiconductor nanocrystals are preferably present in the capillary pool 93. Said detection particles may comprise oligonucleotides complementary to the target analyte or may comprise ligands capable of binding to the amplified target nucleic acid such as biotin, streptavidin, a hapten or an antibody directed against a label such as a hapten present on the target amplified nucleic acids. Detection chamber 230 may contain detection particles that are dried, lyophilized, or present on at least a portion of the interior surface as a dried mixture of detection particles in a carrier such as a polysaccharide, detergent, protein or other compound known to those skilled in the art to facilitate resuspension of the detection particles. In some embodiments the lateral flow detection strip may comprise detection particles. In other embodiments a reagent recess channel 135 leading to the detection chamber my comprise detection particles. The detection chamber may be capable of being heated and/or cooled.

Suitable detection particles include but are not limited to fluorescent dyes specific for duplex nucleic acid, fluorescently modified oligonucleotides, or oligonucleotide-conjugated dyed microparticles or colloidal gold or colloidal cellulose. Detection of amplicon involves a 'detection oligonucleotide' or other 'detection probe' that is complementary or otherwise able to bind specifically to the amplicon to be detected. Conjugation of a detection oligonucleotide to a microparticle may occur by use of streptavidin coated particles and biotinylated oligonucleotides, or by carbodiimide chemistry whereby carboxylated particles are activated in the presence of carbodiimide and react specifically with primary amines present on the detection oligonucleotide. Conjugation of the detection oligonucleotide to the detectable moiety may occur internally or at the 5' end or the 3' end. Detection oligonucleotides may be attached directly to the microparticle, or more preferably through a spacer moiety such as ethyleneglycol or polynucleotides. In some embodiments of the invention, detection particles may bind to multiple species of amplified nucleic acids resulting from such processes as multiplexed amplification. In these embodiments the specific detection of each species of amplified nucleic acid can be realized by detection on the detection strip using a method specific for each species to be detected. In such an embodiment, a tag introduced to the target nucleic acids during amplification may be used to label all amplified species present while subsequent hybridization of the labeled nucleic acids to species specific capture probes immobilized on the detection strip is employed to determine which specific species of amplified DNA are present.

In the case of a duplex DNA amplification product, heating the reaction solution following introduction to the detection chamber may facilitate detection. Melting duplex DNA or denaturing the secondary structure of single stranded DNA and then cooling in the presence of detection oligonucleotide results in the sequence-specific labeling of the amplified target nucleic acid. The heating element underlying the detection chamber may be used to heat the fluid volume for approximately 1 to approximately 120 seconds to initiate duplex DNA melting or denaturation of single stranded DNA secondary structure. As the solution is allowed to cool to room temperature, the amplified target nucleic acid may specifically hybridize to detection microparticles. The reaction volume is then preferably directed to a region of the detection chamber below the labeling chamber by opening the vent of the detection chamber.

Figure 9:
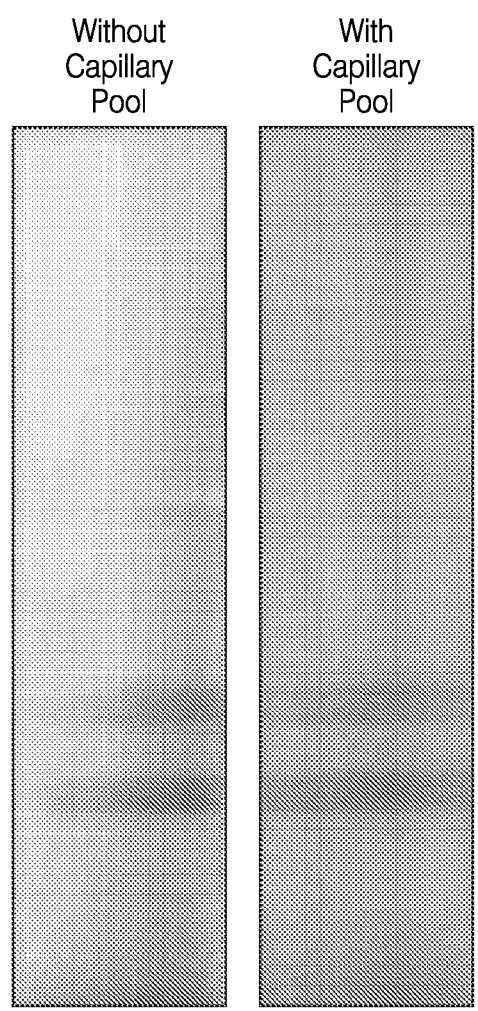
FIG. 9 depicts lateral flow strips from devices with and without a capillary pool at the sample receiving end of the strip. More uniform distribution of detection particles and more uniform signal across the strip is observed when a capillary pool is present.

For efficient labeling to occur, the solubilized detection particles are preferably well mixed with the reaction solution. In embodiments of the invention, detection particles may be localized in capillary pool 93 at the outlet of channel 135 to facilitate mixture with solution as it enters chamber 230. Detection particles in capillary pool 93 may optionally be lyophilized detection particles. The capillary pool provides improved mixing and dispersion of particles to facilitate comingling of the detection particles with the nucleic acids to which the detection particles bind. The capillary pool also increases the uniformity of particle migration on the detection strip, as shown in FIG. 9. A capillary pool is especially advantageous for low volume assays, such as those less than 200 µL, or more specifically less than about 100 µL, or even more particularly less than about 60 µL, or even more particularly about 40 µL in volume.

Embodiments of the detection chamber of the present invention provide for the specific detection of amplified target nucleic acids. In certain embodiments of the invention, detection is accomplished by capillary wicking of solution containing labeled amplicon through an absorbent strip comprised of a porous material (such as cellulose, nitrocellulose, polyethersulfone, polyvinylidine fluoride, nylon, charge-modified nylon, or polytetrafluoroethylene) patterned with lines, dots, microarrays, or other visually discernable elements comprising a binding moiety capable of specifically binding to the labeled amplicon either directly or indirectly. In some embodiments, the absorbent strip component of the device comprises up to three porous substrates in physical contact: a surfactant pad comprising amphipathic reagents to enhance wicking, a detection zone comprising a porous material (such as cellulose, nitrocellulose, polyethersulfone, polyvinylidine fluoride, nylon, charge-modified nylon, or polytetrafluoroethylene) to which at least one binding moiety capable of selectively binding labeled amplicon is immobilized, and/or an absorbent pad to provide additional absorbent capacity. Although detection particles may optionally be incorporated within the lateral flow porous materials in the detection chamber, unlike previously described lateral flow detection devices the detection particles preferably are instead held upstream in a capillary pool where substantially enhanced the formation of binding complexes between amplicon and detection particles may be conducted prior to or concomitant with the introduction of the resultant labeled nucleic acids to the porous components of the device.

A 'capture oligonucleotide' or 'capture probe' is preferably immobilized to the detection strip element of the device by any of a variety of means known to those skilled in the art, such as UV irradiation. The capture probe is designed to capture the labeled nucleic acid as solution containing the labeled nucleic acid wicks through the capture zone resulting in an increased concentration of label at the site of capture probe immobilization, thus producing a detectable signal indicative of the presence of the labeled target nucleic acid amplicon(s). A single detection strip may be patterned with one or multiple capture probes to enable multiplexed detection of multiple amplicons, determination of amplicon sequence, quantification of an amplicon by extending the linearity of the detection signal, and assay quality control (positive and negative controls).

Fluidic Component

Embodiments of the fluidic component preferably comprise plastic, such as acrylic, polycarbonate, PETG, polystyrene, polyester, polypropylene, and/or other like materials. These materials are readily available and able to be manufactured by standard methods. Fluidic components comprise both chambers and channels. Fluidic chambers comprise walls, two faces, and connect to one or more channels such as an inlet, an outlet, a recess, or a vent. Channels can connect two fluidic chambers or a fluidic chamber and a recess, and comprise of walls and two faces. Fluidic chamber design preferably maximizes the surface area to volume ratio to facilitate heating and cooling. The internal volume of a chamber is preferably between approximately 1 µL and approximately 200 µL. The area of a chamber face in contact with solution preferably corresponds with the area to which heating elements are interfaced to ensure uniform fluid temperature during heating. The shape of the fluidic chambers may be selected to mate with heating elements and to provide favorable geometries for solution ingress and egress. In some embodiments, the volume of the chamber may be larger than the fluid volume in order to provide a space for bubbles that appear during the course of device operation. Fluidic chambers may have enlarged extensions leading to vent channels, to ensure that fluid does not encroach upon the channel by capillary action or otherwise block the venting mechanism.

In some embodiments, it may be desirable to reduce or eliminate the invasion of liquid or gas phase water into a chamber prior to the time of solution release. The elevated temperatures employed in processes of some embodiments generate vapors (e.g. gas phase water) that can result in premature invasion of moisture into a channel, chamber or recess. Reduction of liquid phase or gas phase invasion may be desirable to retain, for example, the dried state of dried reagents or lyophilized reagents present in a chamber or recess. In some embodiments, channels may be temporarily blocked, completely or partially, with a material that can be removed by external forces such as heat, moisture, and/or pressure. Materials suitable for the temporary blockage of channels include but are not limited to latex, cellulose, polystyrene, hot glue, paraffin, waxes, and oils.

In some embodiments, the test cassette comprises a preferably injection molded fluidic component comprising sample cup, chambers, channels, vent pockets, and energy directors. The injection molded test cassette fluidic component is preferably comprised of a plastic suitable for ultrasonic welding to a backing plastic of similar composition. In one embodiment of the invention the test cassette fluidic component comprises a single injection molded piece that is ultrasonically welded to a backing material. The energy directors are optional features of the fluidic component that direct the ultrasonic energy to only those areas of the heat labile layer which are intended to bond to the fluidic component. The injection molded fluidic component may optionally be housed in a housing. FIG. 7 illustrates a cassette comprising a preferably injection molded fluidic component 400 (preferably comprising a polymer such as high-impact polystyrene (HIPS), polyethylene, polypropylene, or NAS 30, a styrene acrylic copolymer), a heat labile material 410 (comprising, for example, BOPS, which has relatively low melting temperature of about 239° C. and a glass transition temperature of about 100° C., which is sufficient to withstand the elevated temperatures during denaturation, or polycarbonate, which has a melting temperature of 265° C. and glass transition temperature of 150° C.), adhesive spacer 420 (comprising, for example, a silicone transfer adhesive that preferably does not incorporate a carrier, an acrylic adhesive with a polyester carrier, or any adhesive that can withstand the elevated temperatures of the device), and heat resistant layer 430. Heat labile material 410 ruptures via heat which is preferably transmitted through overlying heat resistant layer 430 (comprising, for example, polyimide or another polymer having high heat resistance). Melting of the heat labile material over the vent features of the cassette opens the vent and vent channel to the expansion chamber, thereby allowing pressure equalization within the cassette. Overlying heat resistant layer 430 preferably remains intact, thereby enabling the cassette to maintain a hermetic seal after vent opening.

In some embodiments, the adhesive spacer comprises a vacant region 440 that may serve as an expansion chamber to buffer the expansion of gases during heating to reduce the internal pressure of a sealed cassette. Heat labile layer 410 is bonded to fluidic component 400 by a bonding method or process such as ultrasonic welding or employing adhesive. The resulting part is then bonded to a spacer and a heat resistant layer. In some embodiments the heat resistant layer is constructed in such a manner that it is not present over heated chambers. In other embodiments, the heat resistant layer is present over heater chambers. In yet other embodiments, the adhesive spacer and heat resistant layers are present only over a region that is in register with the vent pocket features of the fluidic component. In this embodiment a heat resistant layer may optionally be placed directly over the heat labile material in the regions in register with the heated chambers.

In some embodiments of the invention the thickness of the fluidic chambers and channel walls are in the range of approximately 0.025 mm to approximately 1 mm, and preferably in the range of approximately 0.1 mm to approximately 0.5 mm. This thickness preferably meets requirements of both structural integrity of the fluidic component and to support sealing of the closed chamber under high temperatures and associated pressures. The thickness of channel walls, particularly vent channel walls, are preferably less than that of the chambers and in the range of approximately 0.025 mm to approximately 0.25 mm. The width of inlet and outlet channels is preferably chosen to enhance capillarity. A shallow vent channel imparts improved rigidity to the fluidic component with no adverse effect on venting. Plastic forming faces of the fluidic component is preferably thinner than that forming the walls in order to maximize heat transfer. Optional thermal breaks cut through some components of the fluidic component and surround the amplification and detection chambers, contributing to the thermal isolation of the temperature-controlled chambers.

In some embodiments of the invention, before the fluidic component 400 is bonded to the heat labile backing material 410 additional components of the test cassette such as lyophilized reagents 16, detection strip assembly 230, and detection particles may be incorporated. In some embodiments, the components may be laminated by applying pressure to ensure good adhesion. In some embodiments the components may be bonded by a combination of methods such as pressure sensitive adhesives and ultrasonic welding. Adhesives known or found to negatively impact performance of nucleic acid amplification reactions must be avoided. Acrylic- or silicon-based adhesives have been successfully used in the invention. One preferred adhesive film is S17876 supplied by Advanced Adhesives Research. Other adhesives may be used if found to be chemically compatible with employed buffers, plastics and reaction chemistries while providing robust sealing over the temperatures encountered during device operation.

Referring to FIGS. 2 and 7, vent pockets are preferably differentiated from other chambers in their construction. After construction of the fluidic component as described above, vent pockets possess an open face on the side of the fluidic component that will meet with PCA 75 either directly or in some embodiments indirectly through an intervening air gap 420 or vent pocket 54 and heat resistant material 430. To form the vent pocket, an additional plastic component is bonded to seal the chamber, preferably comprising a thin, heat labile membrane 410 adjacent to vent resistor 70 of the PCA. Film 410 comprises a material suitable for ultrasonic welding to the injection molded fluidic component such as polystyrene although other similar materials may be used. This film is well suited to both seal the vent pocket and allow for easy perforation and, thus, venting to a lower pressure chamber when current is passed through the vent resistor generating a rapid temperature increase. Preferably, the film is sufficiently stable when heated so that the material can withstand the temperatures employed in other operations of the test cassette such as heat lysis, reverse transcription and nucleic acid amplification. Use of a material with stability in the temperature ranges employed for denaturation, labeling, reverse transcription, nucleic acid amplification, and detection but with a melting temperature readily attained by resistor 70 allows a single material to be employed for the backing of the injection molded fluidic component 400 to serve as both a face of the chambers and a face of the vent pocket. In some embodiments, additional temperature stability in the areas of the temperature controlled chambers can be realized by an overlying film of heat resistant material such as polyimide. In other embodiments of the invention, a window in the heat labile film is in register with the temperature controlled chambers to allow direct contact between fluids in the chamber and the substrate of a flexible circuit fused to the rear of the test cassette.

Additional Components of the Fluidic Component

As described above, several additional components are preferably incorporated within the fluidic component of the present invention before final bonding. Reagents including buffers, salts, dNTPs, NTPs, oligonucleotide primers, and enzymes such as DNA polymerase and reverse transcriptase may be lyophilized, or freeze-dried, into pellets, spheres or cakes prior device assembly. Reagent lyophilization is well known in the art and involves dehydration of frozen reagent aliquots by sublimation under an applied vacuum. By adding specific formulations of lyoprotectants such as sugars (di- and polysaccharides) and polyalcohols to the reagents prior to freezing, the activity of enzymes may be preserved and the rate of rehydration may be increased. Lyophilized reagent pellets, spheres, or cakes are manufactured by standard methods and, once formed, are reasonably durable and may be easily placed into specific chambers of the fluidic component prior to laminating the final face. More preferably, recesses are incorporated into the fluidic network to allow pellets, spheres, or cakes of lyophilized reagents to be placed in the fluidic component prior to bonding of the fluidic component to the backing material. By selecting the fluidic network geometry and recess location and order, the sample can react with the desired lyophilized reagent at the desired time to optimize performance. For instance, by depositing lyophilized (or dried) reverse transcription (RD and amplification reagent spheres into two separate recesses in the flow paths of RT reaction chamber and amplification chamber enables optimal reverse transcription reaction without the interference of amplification enzymes. In addition, to minimize the interference of RT enzymes to subsequent amplification reaction, RT enzymes post RT reaction presented in the RT reaction could be heat inactivated prior introduction to amplification reagents to minimize their interference to amplification. Optionally, other salt, surfactants and other enhancing chemicals could be added to different recesses to modulate the performance of a assay. Moreover, these recesses facilitate comingling of the lyophilized reagents with liquids as they pass through the recess and also serve to isolate the lyophilized materials from ultrasonic energy during ultrasonic welding and to isolate lyophilized reagents from temperature extremes during heating steps of a test prior to their solubilization. In addition, the recesses ensure that the lyophilized pellets aren't compressed or crushed during manufacture, enabling them to remain porous to minimize rehydration times.

In some embodiments of the invention, detection microparticles are another additional component of the fluidic component. In some embodiments, these microparticles may be lyophilized as described for the reaction reagents above. In other embodiments, microparticles in liquid buffer may be directly applied to an interior face of a fluidic chamber and dried before final assembly of the test cassette. The liquid buffer containing the microparticles preferably also comprises sugars or polyalcohols that aid in rehydration. Incorporation of microparticles in aqueous buffer directly into the fluidic component prior to drying may simplify and reduce the final cost of manufacturing, and complete comingling of lyophilized particles with reaction solution and the denaturation of double-stranded nucleic acids or double-stranded regions of a nucleic acid into single-stranded nucleic acid may be facilitated by heating or nucleate boiling. In some embodiments, lyophilized detection particles are placed in recesses in the fluidic network. In other embodiments, lyophilized or dried detection particles are placed in a space 93 directly below the detection strip. In other embodiments detection particles are dried or lyophilized into a bibulous substrate in capillary communication with the detection strip or are dried or lyophilized directly on the detection strip. Capillary communication may be direct physical contact of the said bibulous substrate with the detection strip or indirect wherein capillary communication is over an intervening distance comprised of a channel or chamber region through which capillary transport is achieved to transport fluid from the detection particle laden bibulous substrate to the detection strip.

In some embodiments of the present invention, a lateral flow detection strip assembly is also incorporated into the fluidic component. The detection strip preferably comprises a membrane assembly comprised of at least one porous component and optionally may comprise an absorbent pad, a detection membrane, a surfactant pad, and a backing film. The detection membrane is preferably made of nitrocellulose, cellulose, polyethersulfone, polyvinylidine fluoride, nylon, charge-modified nylon, or polytetrafluoroethylene and may be backed with a plastic film. As described above, capture probe may be deposited and irreversibly immobilized on the detection membrane in lines, spots, microarrays or any pattern that can be visualized by the unaided human eye or an automated detection system such as an imaging system. Deposited oligonucleotides may be permanently immobilized by UV-irradiation of the detection membrane following capture probe deposition. The surfactant pad may comprise a porous substrate, preferably with minimal nucleic acid binding and fluid retention properties, that permits unobstructed migration of the nucleic acid product and detection microparticles. The surfactant pad may comprise materials such as glass fiber, cellulose, or polyester. In embodiments of the invention, formulations including at least one amphipathic reagent are dried on the surfactant pad to allow uniform migration of sample through the detection membrane. The absorbent pad may comprise any absorbent material, and helps to induce sample wicking through the detection membrane assembly. Using an adhesive backing film, such as a double-sided adhesive film as a base, the detection membrane component is assembled by first placing the detection membrane, followed by optional absorbent pad and/or surfactant pad in physical contact with the detection membrane with between approximately 1 mm and approximately 2 mm overlap. In some embodiments of the invention, the detection membrane may be in indirect capillary communication with the surfactant pad wherein there is a physical separation between the surfactant pad and the detection pad with the intervening space comprised of a capillary space wherein fluids may traverse the space by means of capillary action. In some embodiments, the surfactant pad or a region of the surfactant pad may comprise detection particles, dried detection particles or lyophilized detection particles.

Three Chamber Cassette

Figure 37A:
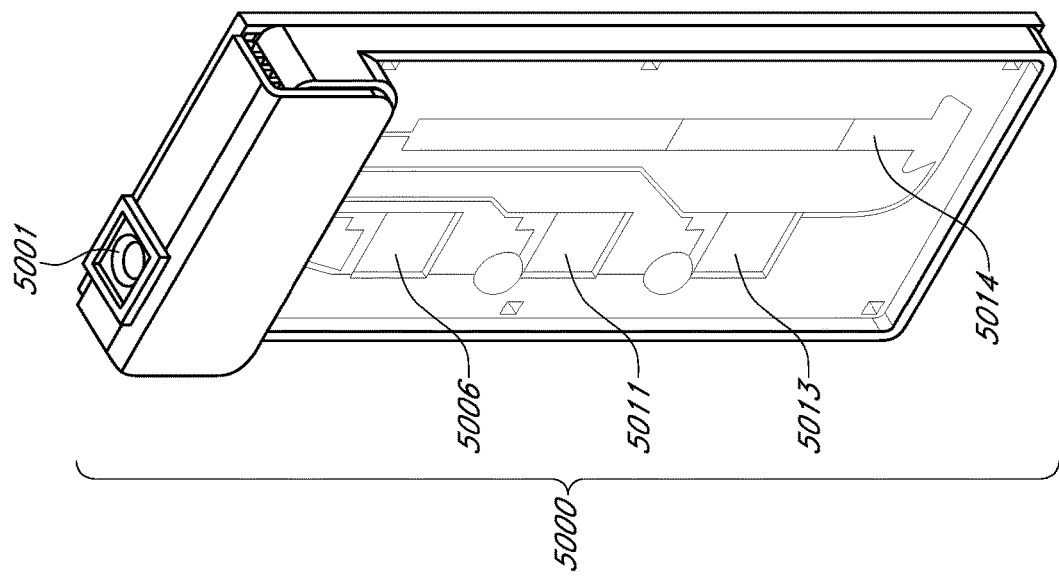
FIG. 37A is a perspective view of a cassette comprising three chambers.
Figure 37B:
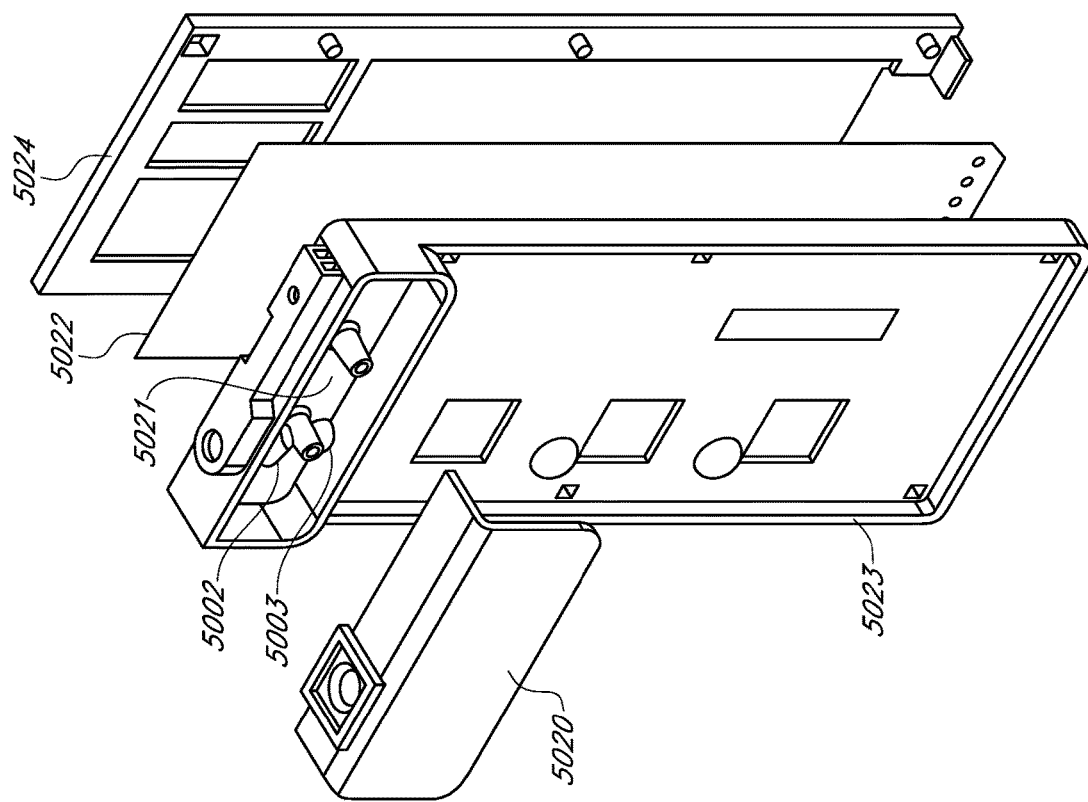
FIG. 37B is an exploded view of the cassette of FIG. 37A.
Figure 38:
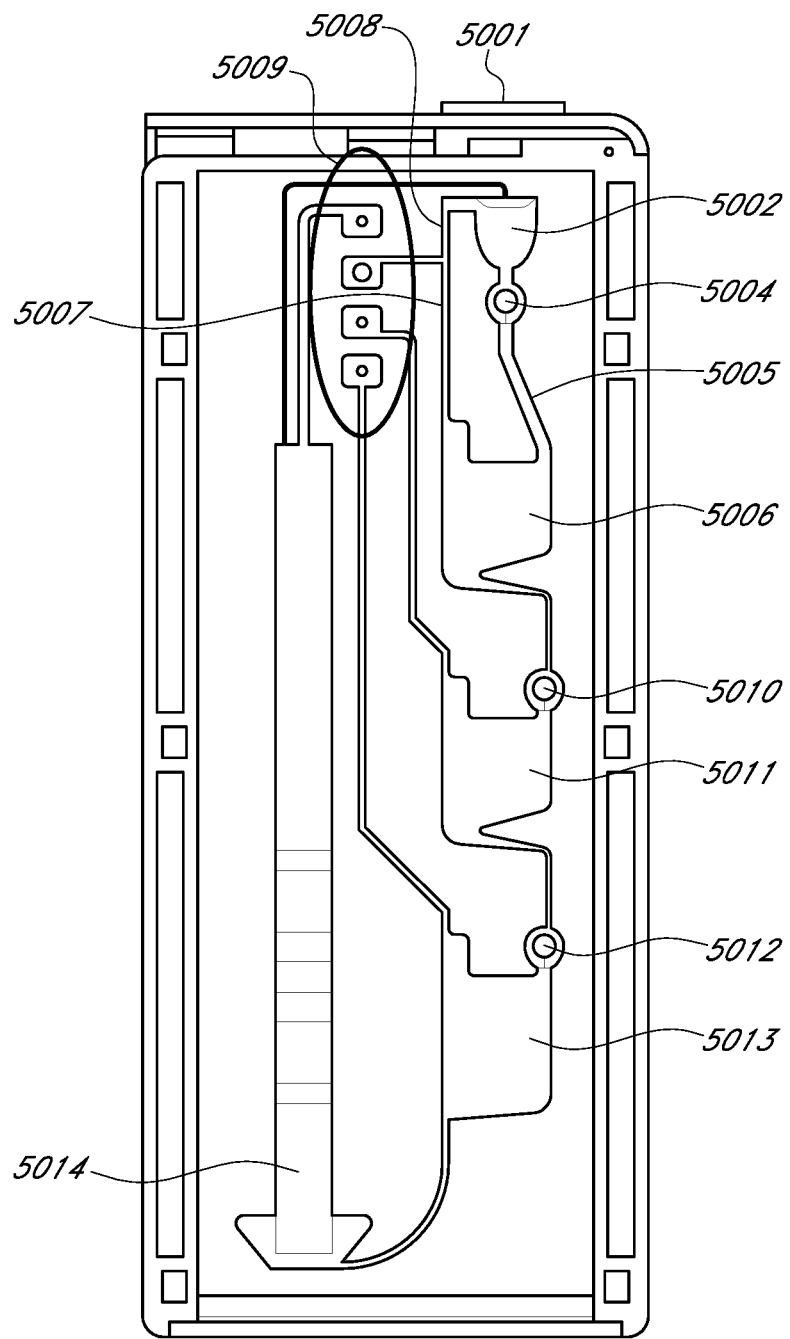
FIG. 38 is a transparent view of the cassette of FIG. 37A showing fluidic features.

In some embodiments of the invention, additional reaction chambers and/or additional recesses for dried or lyophilized reagents may be incorporated. In some embodiments such a design facilitates tests in which it is desirable to provide for an initial separate lysis reaction prior to reverse transcription and amplification. As shown in FIGS. 37A, 37B, and 38, cassette 5000 comprises cover 5020 sealing expansion chamber 5021, flexible heater circuit 5022 preferably disposed in intimate contact with fluidic component 5023, and rear cover 5024 which conceals the circuitry from the user. A sample containing nucleic acids is introduced into sample cup 5002 through sample port 5001. The sample flows freely into recess 5003 where it reconstitutes the first lyophilized bead 5004, preferably comprising lysis reagents, prior to flowing down channel 5005 into first reaction chamber 5006. This free flow is facilitated by vent channel 5007 which connects to the top of the sample cup 5002. Vent channel 5007 may additionally connect to expansion chamber 5021 via hole 5008. The sealed air space below first reaction chamber 5006 pressurizes slightly due to the fluid flow and causes the flow to stop just below first reaction chamber 5006. First reaction chamber 5006 is then preferably heated to a temperature to facilitate proper reaction with the lysis reagents, lysing the biological particles and/or cells in the sample, exposing any nucleic acids present therein.

Opening of the vent valve 5009 connected to the top of second reaction chamber 5011 then facilitates sample flow into a second recess where second lyophilized bead 5010, preferably comprising reagents for reverse transcription, is reconstituted. The fluid then enters second reaction chamber 5011 where it's flow stops as a result of increased air pressure in the closed air volume below the flow. Second reaction chamber 5011 is then preferably subsequently heated to an appropriate temperature to facilitate the reverse transcription process.

Opening of the next vent valve 5009 connected to the top of third reaction chamber 5013 initiates flow of the sample from second reaction chamber 5011 through a third recess where lyophilized bead 5012, preferably comprising lyophilized PCR amplification reagents, is reconstituted. The sample then flows into third reaction chamber 5013, where it undergoes thermal cycling to amplify targeted analytes present in the sample.

Subsequently, opening of the final vent valve 5009 connected to the far end of lateral flow strip 5014 enables the sample which now contains amplified analytes to flow to lateral flow strip 5014 for detection of the analytes as previously described.

Flow Control Features

The design of the fluidic component may optionally comprise flow control features within, or at the outlets of, the reaction chambers. These features deflect the flow entering the chamber to the side of the chamber opposite from the outlet, prior to the flow entering the outlet. As a result the flow enters the outlet channel at a lower velocity, reducing the distance the fluid flows down the channel before it stops. Furthermore, the horizontal component of the flow path adds length to the channel without adding vertical spacing between the chambers, increasing the effective length of the flow path so it is sufficient to stop the flow at the desired location based on the reduced velocity of the flow. This enables closer vertical spacing between chambers of the cassette since less vertical channel is required. In addition, the redirection of the flow across the reaction chamber creates a swirling action in the flow within the chamber, improving mixing of the reagents with the sample fluid. The flow control feature may comprise any shape.

Figure 39:
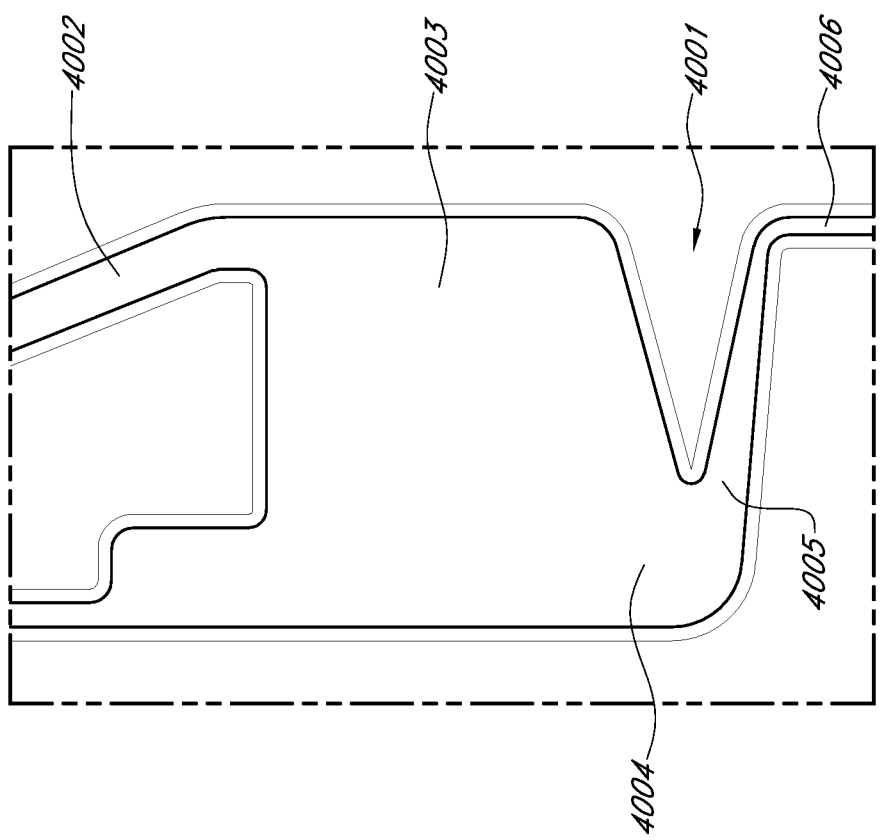
FIG. 39 shows an embodiment of a chamber of the present invention comprising a triangular protruding flow feature and a tapered outlet.

In the embodiment shown in FIG. 39, the fluid enters reaction chamber 4003 from inlet channel 4002 and flows to the bottom of the reaction chamber, where it is redirected to the side of reaction chamber 4003 opposite the opening to inlet channel 4002 by triangular flow control feature 4001. As the flow proceeds to opposite corner 4004, the flow divides, with some entering outlet 4005, while the rest contacts the wall and is directed upward, creating a swirling effect which improves mixing. The flow into the outlet preferably forms a meniscus and travels through outlet channel 4006 towards the next reaction chamber or lyophilized bead recess. Since outlet channel 4006 is sealed below reaction chamber 4003, as the fluid travels along outlet channel 4006 the air pressure increases in the channel below the flow until reaching equilibrium with the fluidic pressure head, thus stopping the flow. In this embodiment outlet 4005 tapers from reaction chamber 4003 to outlet channel 4006 in order to effectively form a meniscus which can subsequently increase pressure in the closed air space downstream of the flow. This larger opening to the outlet channel preferably provides increased compressible air volume so that a meniscus may be reliably formed at the wider opening.

Figure 40:
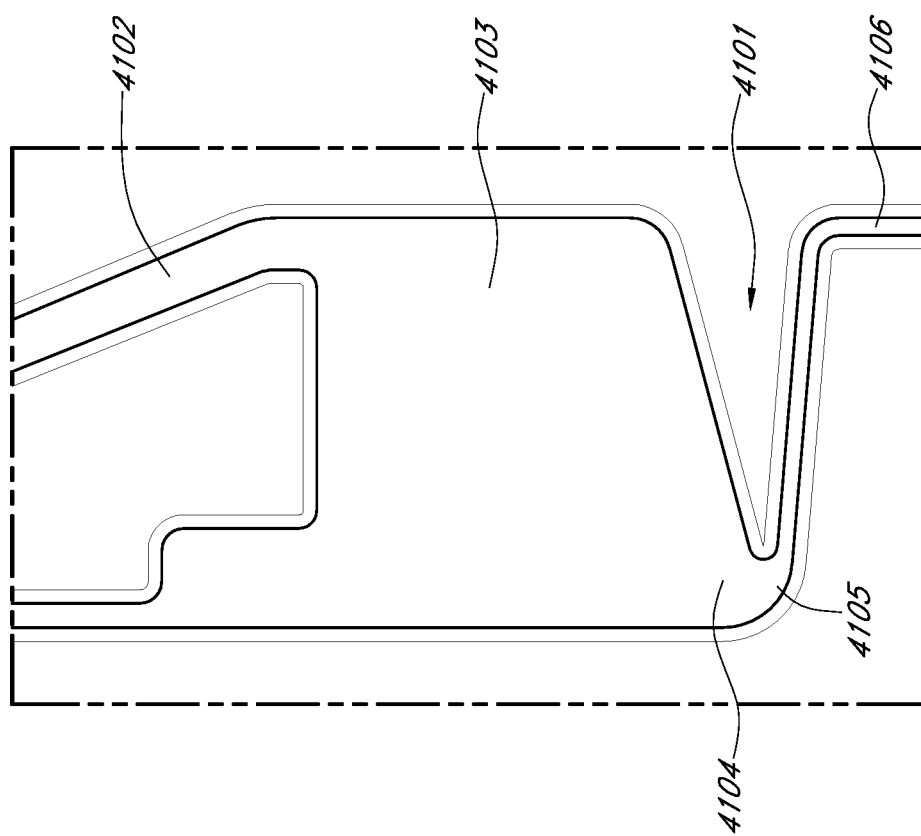
FIG. 40 shows an embodiment of a chamber of the present invention comprising a triangular protruding flow feature and a parallel outlet.

In the embodiment shown in FIG. 40, the fluid enters reaction chamber 4103 from inlet channel 4102 and flows to the bottom of the reaction chamber, where it is redirected to the side of reaction chamber 4103 opposite the opening to inlet channel 4102 by triangular flow control feature 4101. As the flow proceeds to opposite corner 4104, the flow divides, with some entering outlet 4105, while the rest contacts the wall and is directed upward, creating a swirling effect which improves mixing. The flow into the outlet preferably forms a meniscus and travels through outlet channel 4106 towards the next reaction chamber or lyophilized bead recess. Since outlet channel 4106 is sealed below reaction chamber 4103, as the fluid travels along outlet channel 4106 the air pressure increases in the channel below the flow until reaching equilibrium with the fluidic pressure head, thus stopping the flow. In this embodiment outlet 4105 and outlet channel 4106 have uniform width. In this embodiment formation of a meniscus at the reaction chamber may be somewhat more reliable as a result of the narrower channel. The meniscus subsequently increases pressure in the closed air space downstream of the flow.

Figure 41:
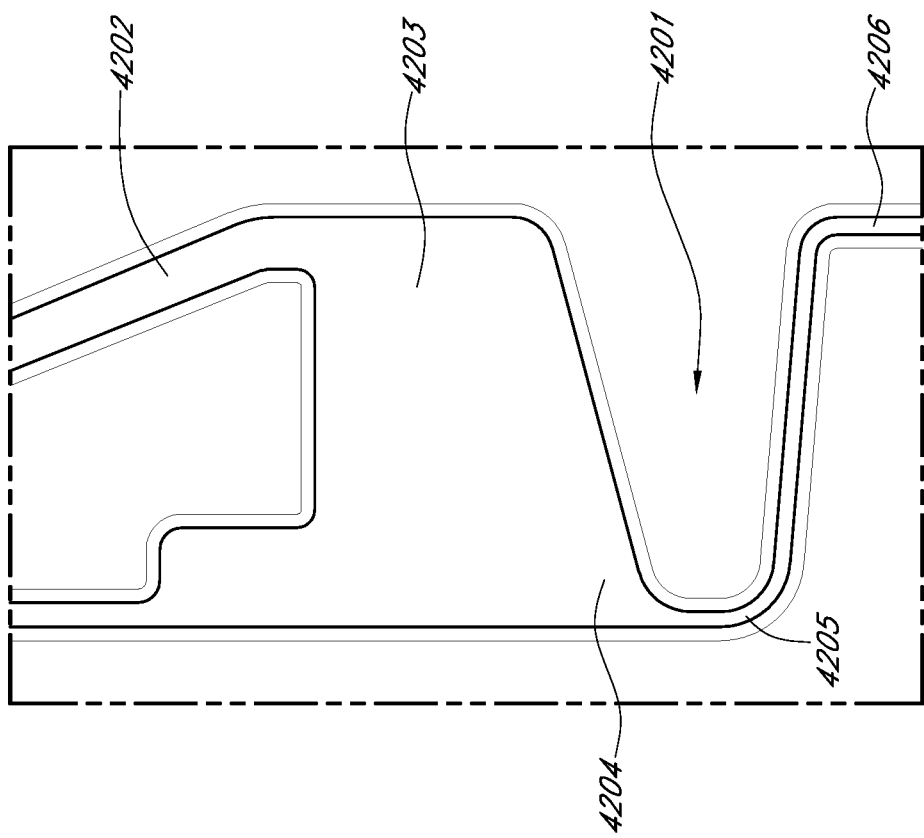
FIG. 41 shows an embodiment of a chamber of the present invention comprising a trapezoidal protruding flow feature and a parallel outlet.

In the embodiment shown in FIG. 41, the fluid enters reaction chamber 4103 from inlet channel 4202 and flows to the bottom of the reaction chamber, where it is redirected to the side of reaction chamber 4203 opposite the opening to inlet channel 4202 by trapezoidal flow control feature 4201. As the flow proceeds to opposite corner 4204, the flow divides, with some entering outlet 4205, while the rest contacts the wall and is directed upward, creating a swirling effect which improves mixing. In this embodiment outlet 4205 is oriented substantially vertically. The flow into the outlet preferably forms a meniscus and travels through outlet channel 4206 towards the next reaction chamber or lyophilized bead recess. Since outlet channel 4206 is sealed below reaction chamber 4203, as the fluid travels along outlet channel 4206 the air pressure increases in the channel below the flow until reaching equilibrium with the fluidic pressure head, thus stopping the flow. In this embodiment outlet 4205 and outlet channel 4206 have uniform width. In this embodiment formation of a meniscus at the reaction chamber may be somewhat more reliable as a result of the narrower channel. The meniscus subsequently increases pressure in the closed air space downstream of the flow.

Figure 42:
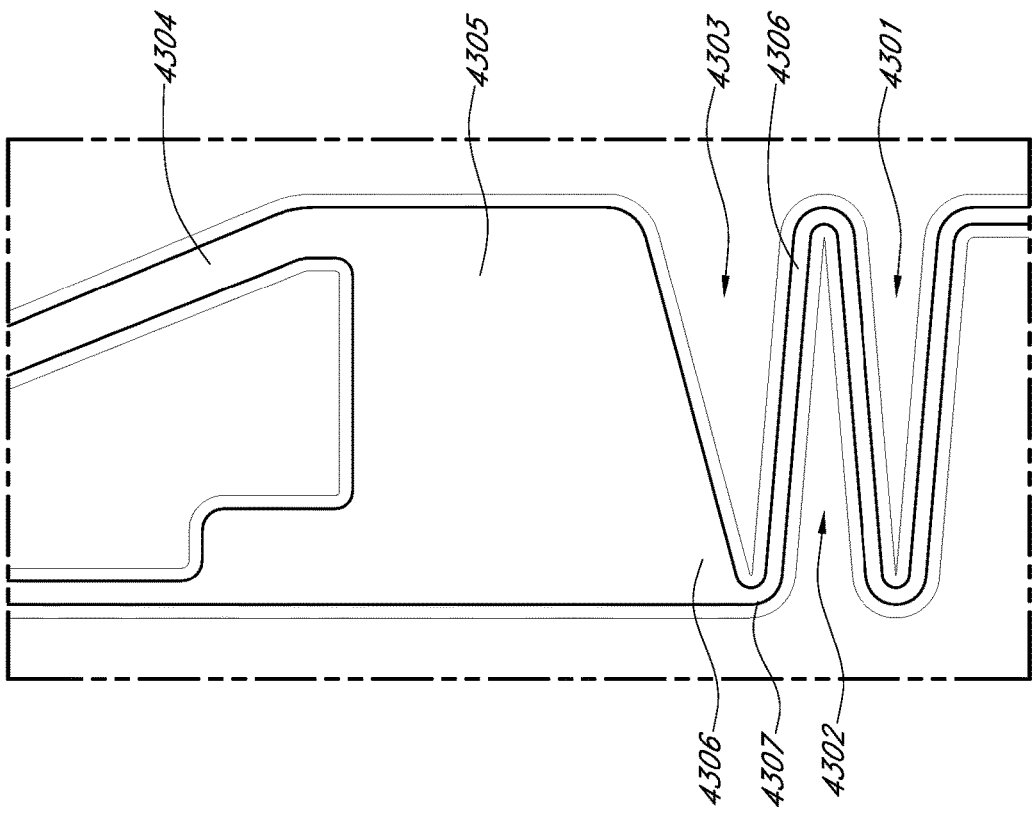
FIG. 42 shows an embodiment of a chamber of the present invention comprising stacked triangular flow features and a parallel outlet.

In the embodiment shown in FIG. 42, the fluid enters reaction chamber 4305 from inlet channel 4304 and flows to the bottom of the reaction chamber, where it is redirected to the side of reaction chamber 4305 opposite the opening to inlet channel 4304 by triangular flow control feature 4303. As the flow proceeds to opposite corner 4306, the flow divides, with some entering outlet 4307, while the rest contacts the wall and is directed upward, creating a swirling effect which improves mixing. The flow into the outlet preferably forms a meniscus and travels through outlet channel 4306 towards the next reaction chamber or lyophilized bead recess. In this embodiment outlet channel 4306 travels through stacked serial flow control features 4303, 4302, and 4301 which provide a tortuous route for the fluid to flow, providing an increased outlet channel length in a small vertical space.

Figure 43:
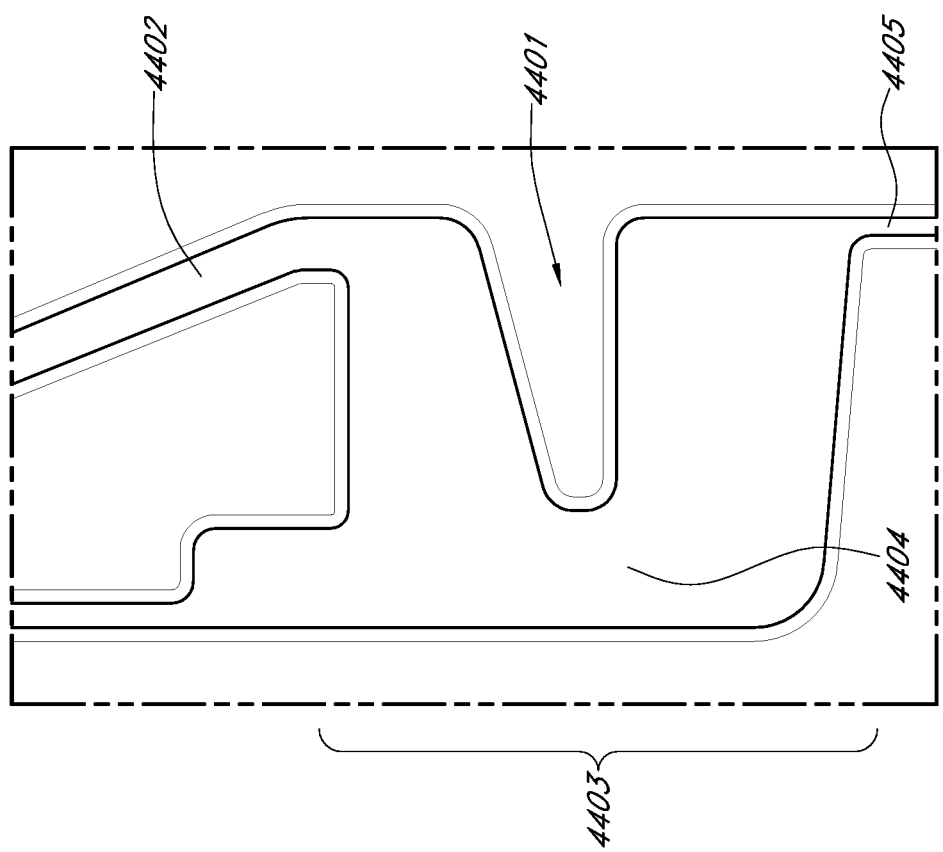
FIG. 43 shows an embodiment of a chamber of the present invention comprising a protruding flow feature in approximately the middle of the chamber.

In the embodiment shown in FIG. 43, the fluid enters reaction chamber 4403 from inlet channel 4402 and is redirected to the side of reaction chamber 4403 opposite the opening to inlet channel 4402 by flow control feature 4401 disposed above the bottom of the reaction chamber, preferably approximately halfway along the length of reaction chamber 4403. In contrast to the previous embodiments, flow control feature 4401 does not form the outlet of reaction chamber 4403. Flow control feature 4401 deflects the flow away from outlet channel 4405 into opposite corner 4404, thereby reducing the flow velocity prior to exiting the chamber. Similar to the previous embodiments the fluidic redirection promotes turbulence and reagent mixing.

Multiplexing of Assays

Figure 10:
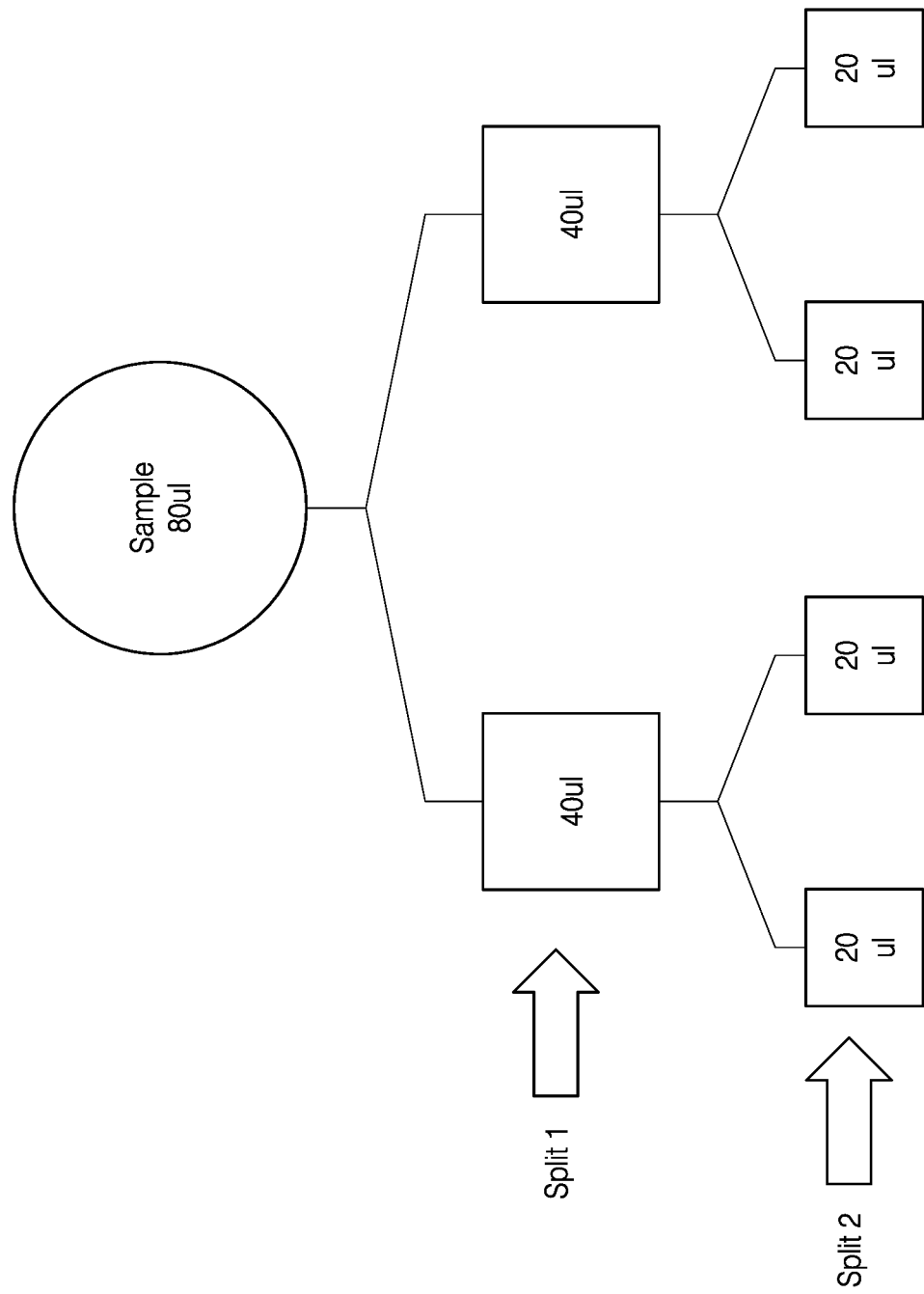
FIG. 10 is a diagram illustrating a hierarchical approach to sample splitting.
Figure 11:
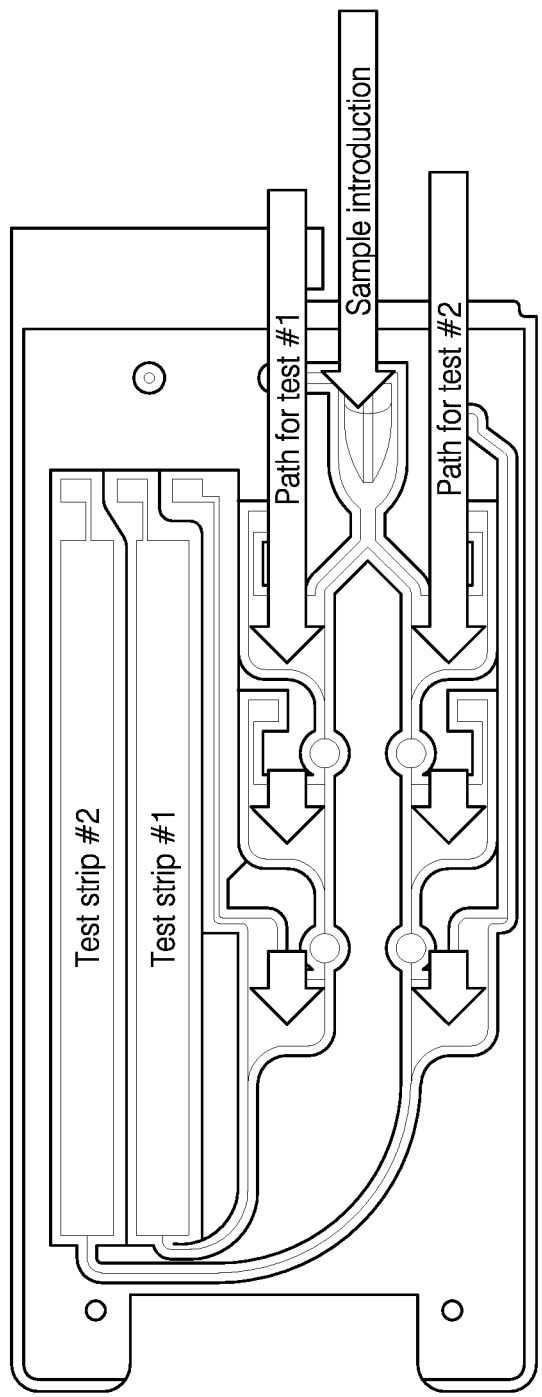
FIG. 11 is an illustration of a multiple channel fluidic network for multiplexing and sample subdivision showing the fluid flow path for each test. Additional fluidic paths or channels can be incorporated into the network to further increase the number of parallel tests that can be performed simultaneously in a single disposable test cassette.
Figure 12:
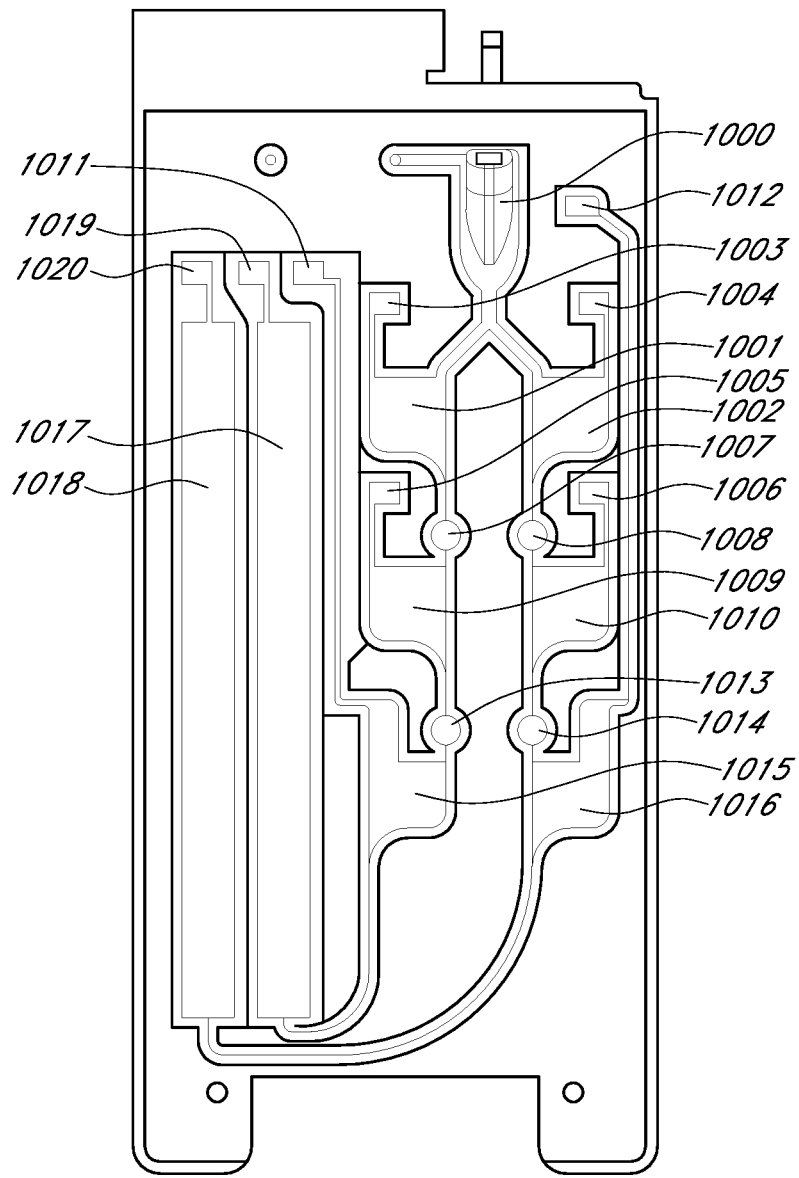
FIG. 12 is a representation of the fluidic network in one embodiment of a test cassette of the invention wherein a sample is split following introduction to the sample cup via the sample port to enable parallel independent tests on the same input sample. A bifurcating fluid path from the sample cup allows sample solution to be split into two distinct fluidic channels or paths of the test cassette to allow simultaneous tests to run in parallel on the split sample.

In some embodiments of the invention, multiple independent assays may be performed in parallel by employing a fluidic design that enables splitting an input fluid sample into two or more parallel fluidic paths through the device. FIG. 10 is a schematic representation of splitting a fluid volume, for example 80 uL, in two sequential steps into first two separate 40 uL volumes and subsequently into four 20 uL volumes. The illustrated scheme is useful to enable separate independent manipulations such as biochemical reactions to be conducted on the split volumes. Such configurations are useful for increasing the number of analytes that can be detected in a single device by facilitating the multiplexed detection of multiple targets such as nucleic acid sequences in multiplexed nucleic acid reverse transcription and/or amplification reactions. Similarly, the use of multiple detection strips at the end of the independent fluid paths can afford enhanced readability of strips for the detection of multiple targets or distinguishing sequence differences or mutations in nucleic acid analytes. Furthermore, providing additional detection strips for independent interrogation of multiple amplification reaction products can enhance specificity by reducing the likelihood of spurious cross-reactivity such as cross hybridization during the detection step of the test. FIG. 11 illustrates a test cassette comprising two fluid paths in a single test cassette. Each fluid path may be independently controlled with respect to timing, reaction type, etc. Referring now to FIG. 12, a sample introduced to sample cup 1000 is divided into approximately equal volumes and flows into volume splitting chambers 1001 and 1002, flow into which is regulated by vent valves 1003 and 1004. Splitting chambers 1001 and 1002 control the volume of sample in each test path by passively equilibrating the amount of sample in each chamber. After volume splitting, solution is allowed to flow through reagent recesses 1007 and 1008 by opening of vents 1005 and 1006. Reagents such as lyophilized reagents are disposed in recesses 1007, 1008 and comingled with the sample as it flows through the recesses and into a first set of preferably temperature controlled chambers 1009 and 1010. Reactions such as heat lysis, reverse transcription, and/or nucleic acid amplification are conducted in each of the first set of heated chambers facilitated by reagents provided in the reagent recesses 1007, 1008. Such reagents may include but are not limited to lyophilized positive control agent (e.g. nucleic acid, virus, bacterial cells, etc.), lyophilized reverse transcriptase and associated accessory reagents such as nucleotides, buffers, DTT, salts, etc. required for reverse transcription of RNA to DNA, and/or DNA amplification using lyophilized DNA polymerase or thermostable lyophilized DNA polymerase and required accessory reagents such as nucleotides, buffers, and salts.

Following the completion of biochemical reactions such as reverse transcription, nucleic acid amplification or concomitant reverse transcription and nucleic acid amplification (e.g. single tube reverse transcription-polymerase chain reaction (RT-PCR) or one-step RT-PCR or one-step RT-Oscar) in the first set of chambers, seals for vent pockets 1011 and 1012 are ruptured to allow fluid to flow from the first set of chambers through a second set of reagent recesses 1013 and 1014 and into a second set of preferably temperature controlled chambers 1015 and 1016. Reagents such as lyophilized reagents may be disposed in recesses 1013 and 1014 such that they comingle with the sample solution as fluid flows from chambers 1009 and 1010 to chambers 1015 and 1016. Reagents such as lyophilized reagents for nucleic acid amplification or dried or lyophilized detection particles such as probe conjugated dyed polystyrene microspheres or probe conjugated colloidal gold may optionally be placed in reagent recesses 1013 and/or 1014. Following completion of reactions or other manipulations such as binding or hybridization to probe conjugated detection particles in heated chambers, solution is allowed to flow into detection strip chambers 1017 and 1018 by opening vent valves 1019 and 1020. In some embodiments, a third set of reagent recesses may be placed in the fluid paths from chambers 1015 and 1016 such that additional reagents, such as detection reagents comprising detection particles, salts and/or surfactants and other substances useful to facilitate hybridization or other detection modalities, may be comingled with the solution flowing into strip chambers 1017 and 1018. Detection strip chambers 1017 and 1018 may be heated and preferably comprise detection strips such as lateral flow strips for the detection of analytes such as amplified nucleic acids. Detection strips may comprise a series of absorbent materials doped or patterned with dried or lyophilized detection reagents such as detection particles (e.g. dyed microsphere conjugates and/or colloidal gold conjugates), capture probes for the capture of analytes such as hybridization capture oligonucleotides for the capture of nucleic acid analytes by sequence specific hybridization, ligands such as biotin or streptavidin for the capture of appropriately modified analytes, and absorbent materials to provide an absorbent capacity sufficient to ensure complete migration of the sample solution volume through the detection strip by such means as capillary action or wicking.

Sample Preparation

Figure 13A:
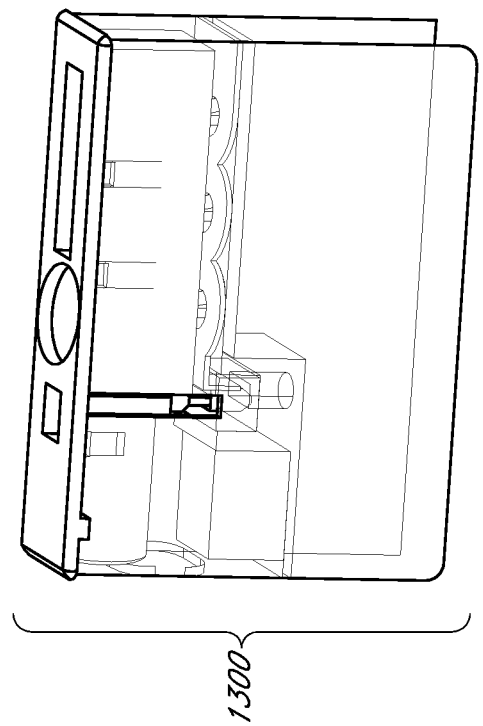
FIG. 13A is a drawing of an assembled sample preparation subsystem showing the internal component arrangement.
Figure 13B:
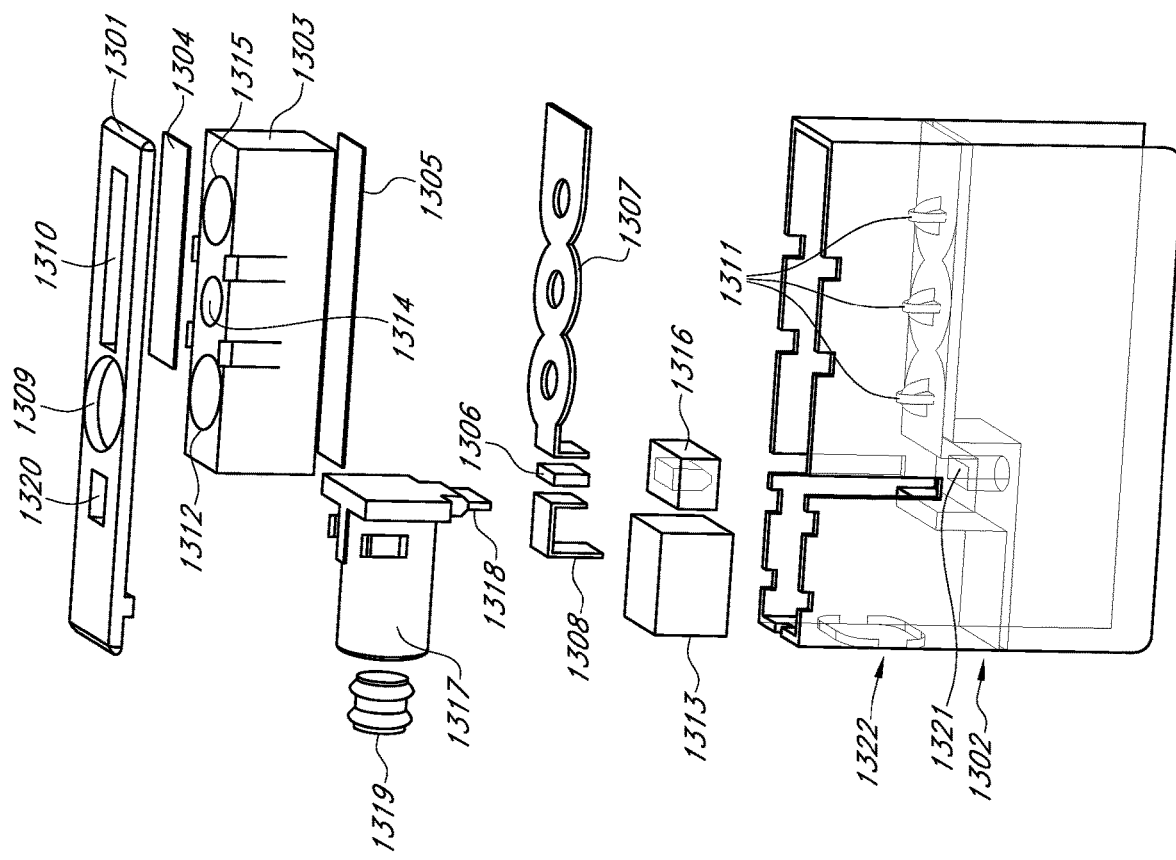
FIG. 13B is an exploded view of the sample preparation subsystem showing components of the nucleic acid purification apparatus configured for integration with a test cassette.

In some embodiments of the invention, it may be desirable to incorporate a sample preparation system into the cassette. A sample preparation system, such as a nucleic acid purification system, may comprise encapsulated solutions for accomplishing sample preparation and elution of purified molecules such as purified DNA, RNA or proteins into the test cassette. FIG. 13 depicts a nucleic acid sample preparation subsystem 1300 designed for integration with a test cassette. The sample preparation subsystem comprises a main housing 1302 and housing lid 1301 to house components of the subsystem. A solution compartmentalization component 1303 comprises crude sample reservoir 1312 which is preferably open on the upper face but sealed underneath by lower seal 1305. Solution compartmentalization component 1303 also preferably comprises reservoir 1314 containing a first wash buffer and reservoir 1315 containing a second wash buffer, both of which are preferably sealed by means of upper seal 1304 and lower seal 1305. A nucleic acid binding matrix 1306 is placed in the solution capillary flow path provided by absorbent materials 1307 and 1308. Glass fiber or silica gel exhibiting nucleic acid binding properties and wicking properties are examples of materials suitable for use as binding matrix 1306. A wide range of absorbent materials may comprise the absorbent materials 1307 and 1308, including polyester, glass fiber, nitrocellulose, polysulfone, cellulose, cotton or combinations thereof as well as other wicking materials provided they offer adequate capillarity and minimal binding to the molecules to be purified by the subsystem. Any readily ruptured or frangible material capable of being sealed to solution compartmentalization component 1303 and chemically compatible with the encapsulated solutions is suitable for use as seal material 1304 and 1305. Seal material 1305 comes in contact with sample or sample lysate and must additionally be chemically compatible with the sample or sample lysate solution. Examples of suitable seal material are heat sealable metallic film and plastic film. Seal material 1305 is ruptured at the time of use by displacement of the solution compartmentalization component 1303 such that the seal 1305 is pierced by structures 1311 present in housing 1302. Crude sample or crude sample mixed with a lysis buffer such as a buffer comprised of a chaotropic agent is introduced at the time of use to the sample reservoir 1312 via the sample port 1309 in lid 1301. In some embodiments, lysis buffer may optionally be encapsulated in reservoir 1312 by extending seal 1304 to cover the upper orifice of reservoir 1312. In such embodiments it may be desirable to include a tab or other means for the partial removal of that region of seal 1304 covering reservoir 1312 to allow the addition of crude sample to reservoir 1312 such that crude sample may comingle or mix with the lysis buffer contained therein. Sample solution or lysate containing sample material is introduced to the sample addition port 1309 and retained in sample reservoir 1312 of buffer reservoir 1303 until the initiation of the sample preparation process.

At the time of sample preparation initiation, solution compartmentalization component 1303 is pushed onto the seal piercing structures 1311 resulting in the simultaneous release of sample solution or lysate in reservoir 1312 and first and second wash buffers in reservoirs 1314 and 1315 respectively. Mechanical displacement of component 1303 may be accomplished manually or by the use of an actuator or actuators present in a reusable instrument into which the disposable test cassette is placed at the time of use. Actuator access or manual displacement mechanism access to reservoir 1303 is preferably provided through access port 1310 of housing lid 1301. Sample or lysate solution and first and second wash buffers are moved through materials 1307, 1306 and 1308 by capillary action. The physical arrangement of the reservoirs and the geometric configuration of absorbent material 1307 ensure sequential flow of the crude lysate, first wash buffer and second wash buffer through the binding matrix 1306. Additional absorbent capacity to ensure continued capillary transport of all solution volumes through the system is provided by absorbent pad 1313 placed in contact with wick 1308. At the completion of solution transport through the absorbent materials, spent solutions come to rest in absorbent pad 1313. Following exhaustion of capillary transport of all solutions through the system, purified nucleic acids are bound to binding matrix 1306, from which the nucleic acids may be eluted into the sample cup 1402 of the integrated test cassette, as shown in FIG. 15.

Figure 14:
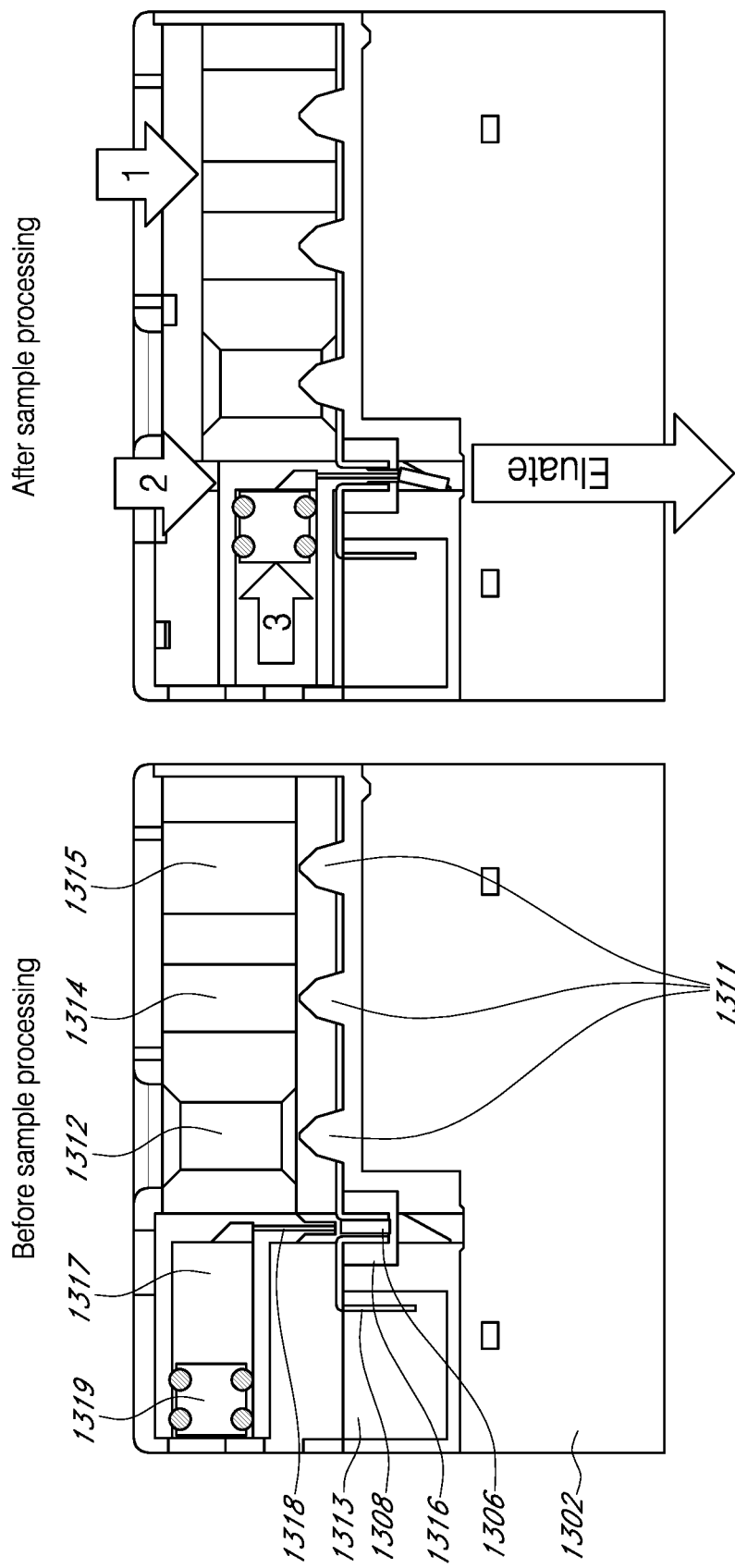
FIG. 14 is a cross-section through the sample preparation subsystem illustrating the movements of components occurring in the course of processing a sample.

Movement of the sample preparation subsystem components occurring during the sample preparation process are shown in FIG. 14, which depicts the sample preparation subsystem embodiment in cross-section before and after sample processing. Elution is preceded by displacement of binding matrix 1306 out of the capillary flow path and through seal component 1316 by the action of an actuator in the associated reusable test instrument. Seal component 1316 forms a seal with a portion of elution buffer conduit 1318 to allow the injection of elution buffer through binding matrix 1306 and into sample cup 1402 without solution loss to the capillary flow path of the sample preparation subsystem. Conduit 1318 is attached to or part of the elution buffer injector component comprised of elution buffer reservoir 1317 and plunger 1319. Plunger 1319 may optionally comprise o-rings to facilitate sealing of elution buffer within reservoir 1317. During elution of purified nucleic acid, an actuator moves elution reservoir component 1317 such that attached conduit 1318 forms a seal with seal component 1316 and displaces binding matrix 1306 into chamber 1321. Mechanical access to depress elution reservoir 1317 is provided through actuator access port 1320. Following displacement of binding matrix 1306 out of the main capillary solution flow path of the sample preparation subsystem, binding matrix 1306 resides in elution chamber 1321. Elution of purified nucleic acid into sample cup 1402 is accomplished by forcing elution buffer from elution buffer reservoir 1317 by an actuator acting through actuator port 1322 to move plunger 1319 through reservoir 1317 in a syringe-like action. Elution buffer proceeds via conduit 1318 through binding matrix 1306, resulting in the injection of elution buffer containing eluted purified nucleic acids into sample cup 1402.

Figure 15:
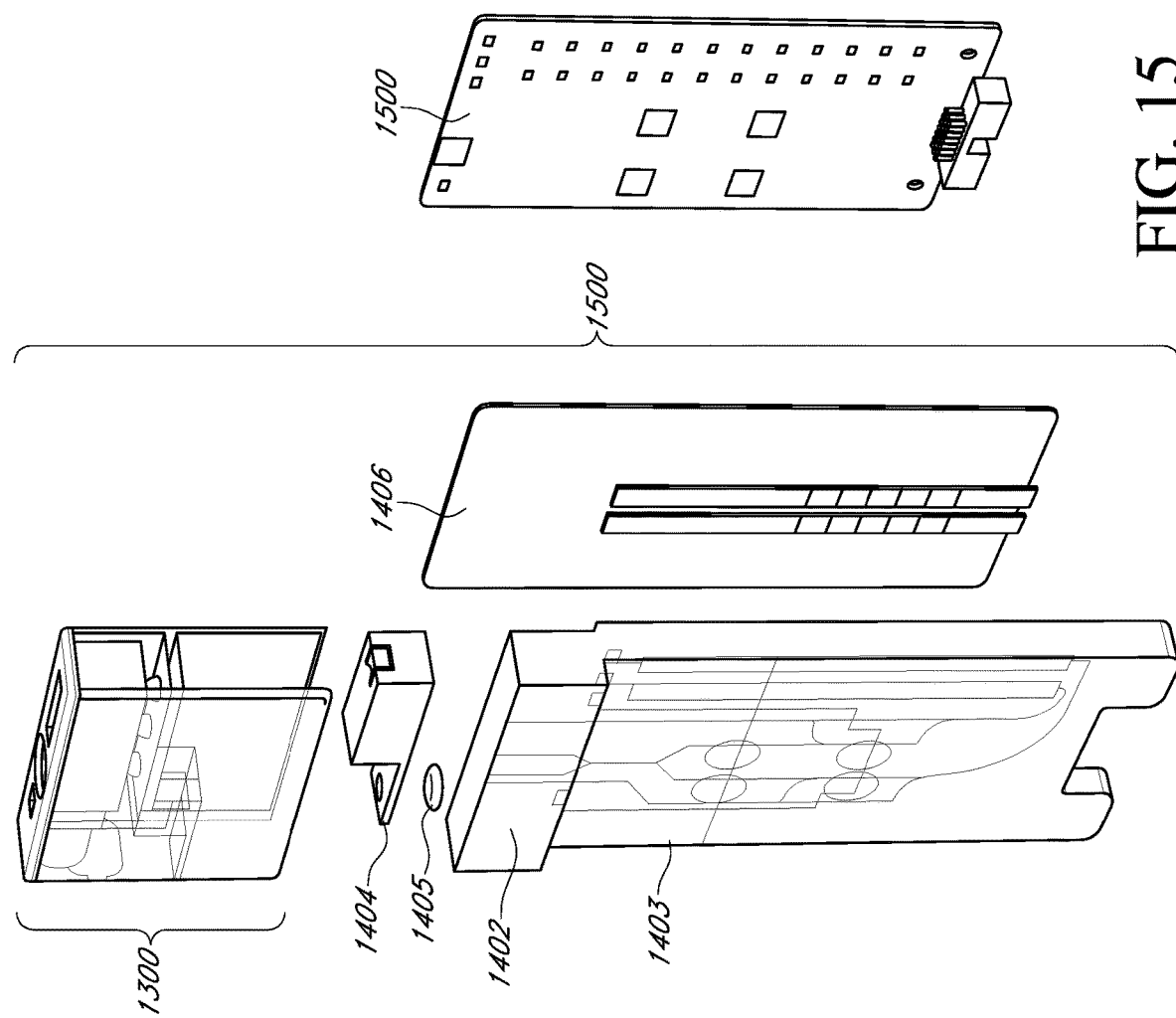
FIG. 15 is an exploded view drawing showing the sample preparation subsystem with hermetic seal components, injection molded fluidic subsystem, corresponding cassette backing and PCA.
Figure 16:
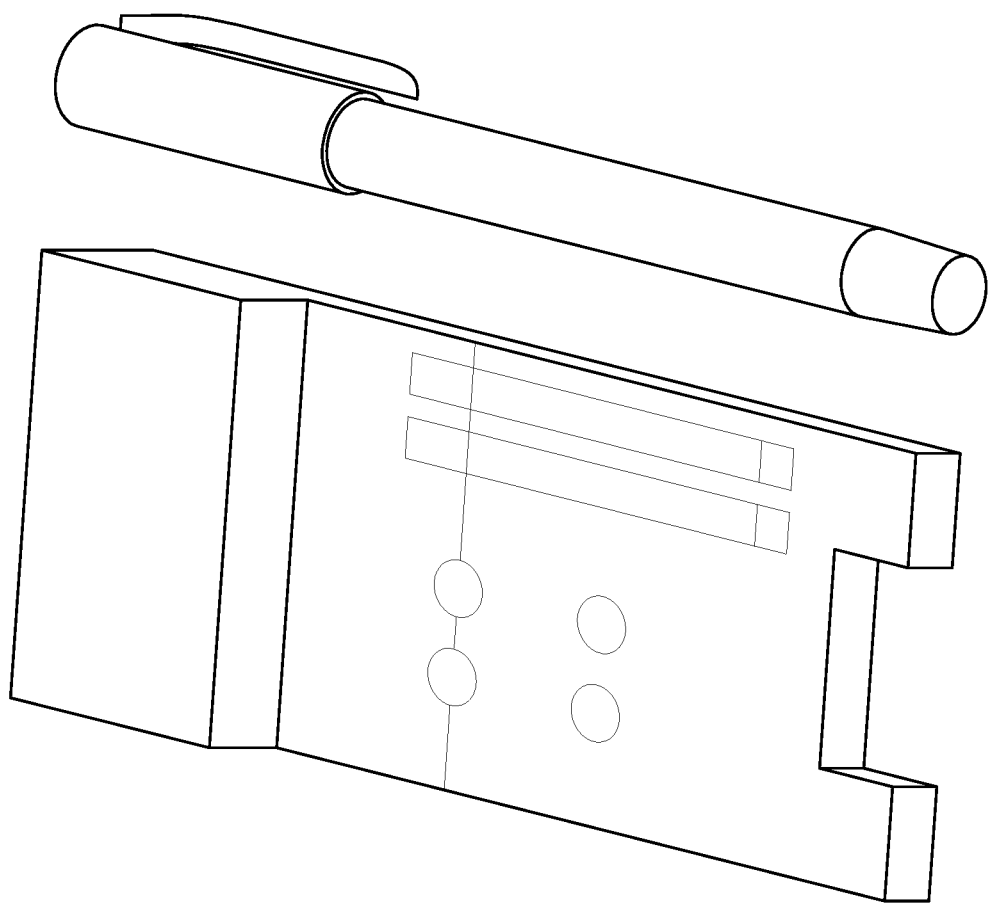
FIG. 16 is a photograph of a test cassette embodiment with an integrated sample preparation subsystem.
Figure 17A:
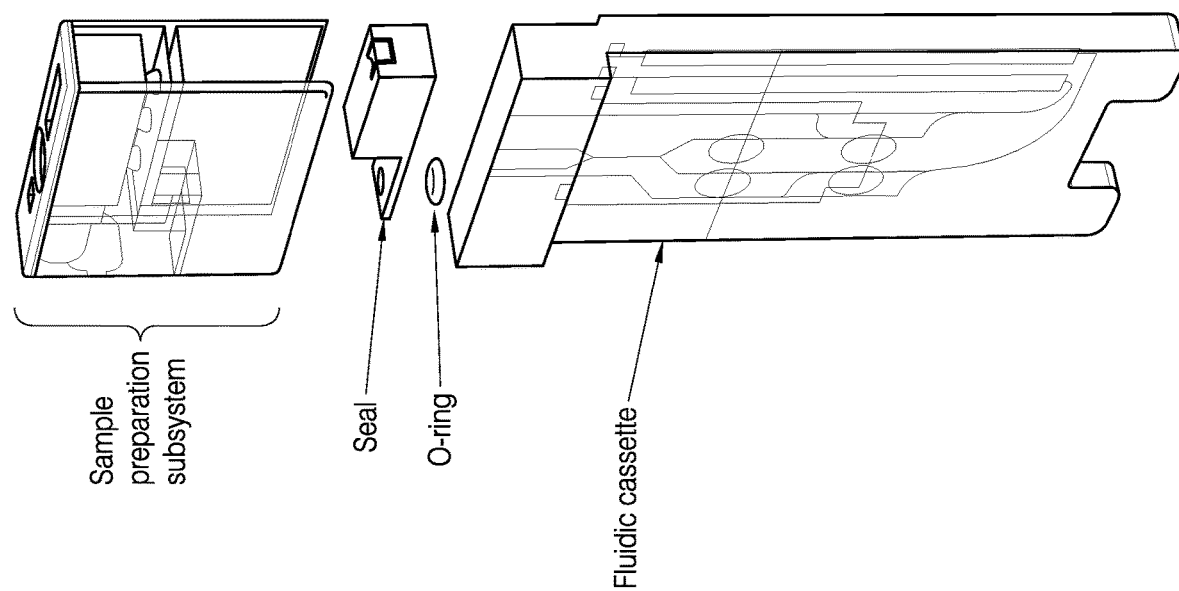
FIG. 17A is an exploded view drawing showing a sample preparation subsystem with hermetic seal components and injection molded fluidic subsystem design.
Figure 17B:
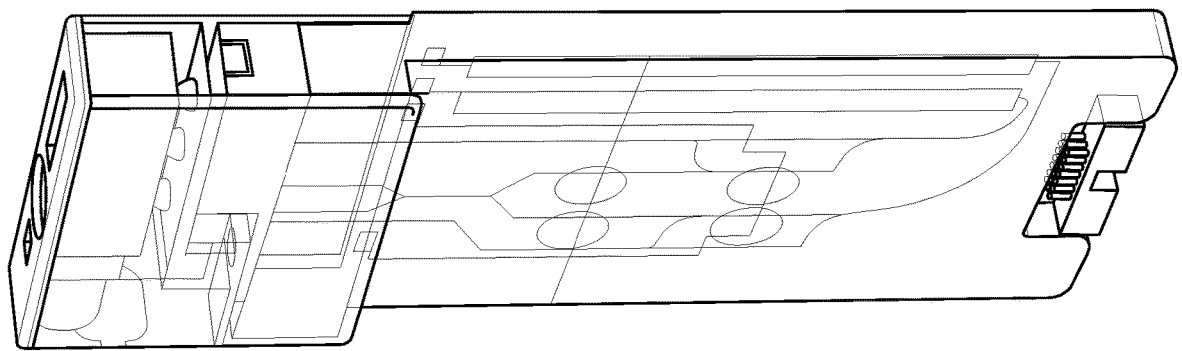
FIG. 17B is a drawing of the test cassette embodiment with integrated sample preparation subsystem shown interfaced to the PCA.
Figure 17C:
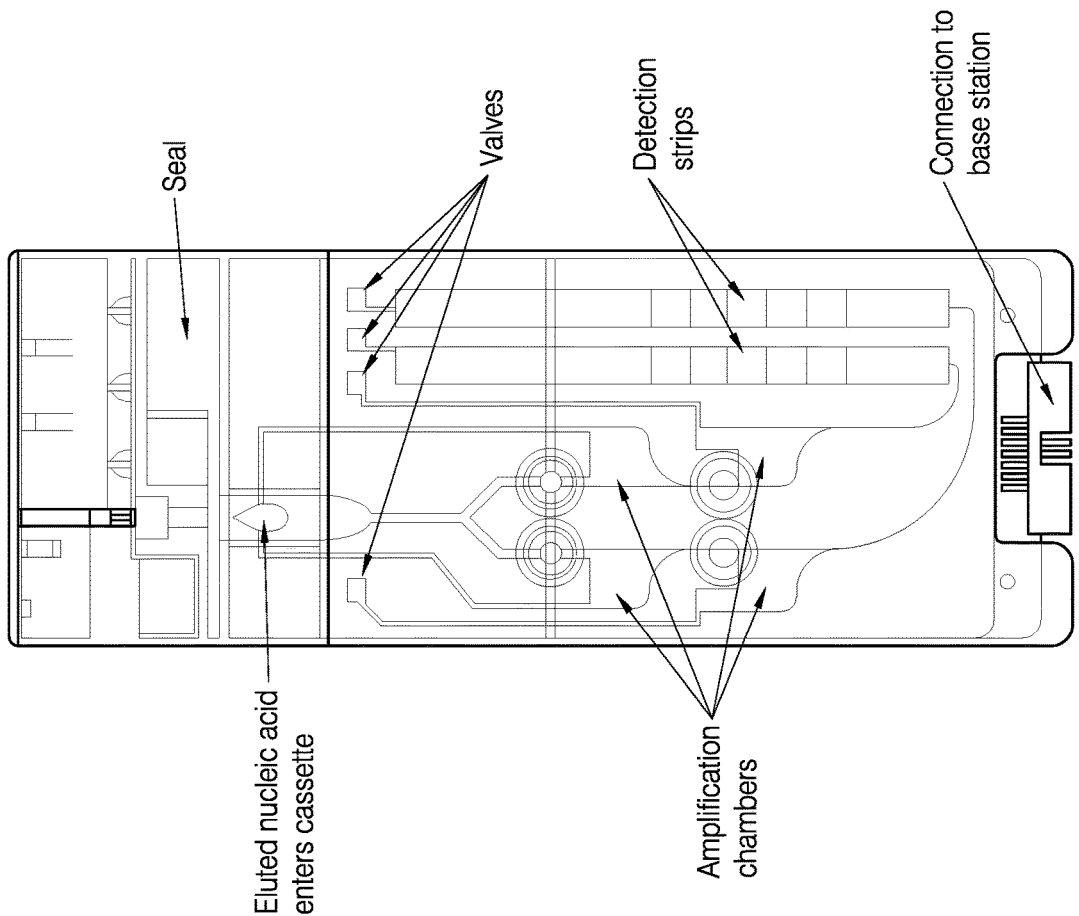
FIG. 17C is a cutaway drawing of the test cassette embodiment depicting the fluidic paths, interfaced electronics and sample preparation components.

Referring now to FIG. 15, sample preparation subsystem 1300 is preferably bonded to fluidic component 1403 of cassette 1500 by widely used manufacturing methods such as ultrasonic welding to form an integrated single use sample-to-result test cassette. In some embodiments, it is desirable to hermetically seal the test cassette fluidics following the introduction of eluate containing purified nucleic acid in order to reduce the likelihood of amplified nucleic acid escape from the cassette. A sliding seal 1404 may optionally but preferably be placed between the sample preparation subsystem and the test cassette fluidic housing 1403 to seal the cassette at the entrance to sample cup 1402. Sliding seal 1404 is moved to the sealed position by the action of an actuator to form a hermetic seal comprising o-ring 1405. Cassette backing 1406 is bonded to the fluidic housing following the introduction of dried reagents and test strips. As described above for the backing of other test cassette embodiments, backing 1406 comprises materials for vent functionality, hermetic seal maintenance, thermal interface, expansion chamber(s) and may optionally comprise a printed circuit board or flexible circuit layer carrying fluid and temperature control electronic components. Electronic components may optionally be housed in a reusable docking unit. PCA 1501 comprising electronic components is preferably constructed of low thermal mass materials and surface mount electronic components. Arrays of surface mount resistors and proximally situated temperature sensors provide one means of regulating chamber temperatures in the test cassette. Surface mount resistors and temperature sensor arrays of PCA 1501 are situated to be in register with the test cassette when the test cassette in loaded into the docking unit. A sample-to-result integrated cassette is shown in FIG. 16. FIG. 17 illustrates the integrated cassette with an underlying electronics layer based on traditional printed circuit board and surface mount components. In some embodiments a flexible circuit may be bonded to the rear of the test cassette.

Electronics

In some embodiments it is desirable to place electronic components in a reusable component such that heaters, sensors and other electronics are interfaced to the disposable test cassette by a means capable of establishing a favorable thermal interface and accurate registration of electronics with overlying elements of the disposable test cassette with which they must interface. In other embodiments it is desirable to use a combination of reusable and disposable components for temperature control. For example, stand-off temperature monitoring can be accomplished with infrared sensors placed in a reusable docking unit, while resistive heaters for temperature control and fluidics control are placed in a flexible circuit integrated into the disposable test cassette.

In some embodiments, the printed circuit board (PCB) comprises a standard 0.062 inch thick FR4 copper clad laminate material, although other standard board materials and thicknesses may be used. Electronic components such as resistors, thermistors, LEDs, and the microcontroller preferably comprise off-the-shelf surface mount devices (SMDs) and are placed according to industry standard methodology.

In alternative embodiments, the PCA could be integrated with the cassette wall and comprise a flexible plastic circuit. Flex circuit materials such as PET and polyimide may be used as shown in FIG. 8. The use of flexible plastic circuitry is well known in the art. In another embodiment, heating elements and temperature sensors may be screen printed onto the plastic fluidic component with technology developed by companies such as Soligie, Inc.

In some embodiments of the invention, the PCB thickness as well as the amount and placement of copper in regions surrounding the resistive heaters are tailored for thermal management of the reaction solution in the fluidic component. This can be accomplished by use of standard manufacturing techniques already mentioned.

In some embodiments of the invention, the resistor is a thick film 2512 package, although other resistors may be used. Heating chambers in the fluidic component are preferentially of dimensions similar to those of the resistor to ensure uniform heating throughout the chamber. A single resistor of this size is sufficient to heat approximately 15 µL of solution, assuming a fluidic component thickness of 0.5 mm. The drawing in FIG. 2D shows two resistors 100 forming a heater sufficient to heat approximately 30 µL of solution, assuming a fluidic component thickness of 0.5 mm. In this case, the resistors are preferably 40 ohm each and arranged in a parallel configuration.

In some embodiments of the invention, temperature sensor 110 preferably comprises a thermistor, such as a 0402 NTC device, or a temperature sensor such as the Atmel AT30TS750, each of which has a height similar to that of the 2512 resistor package. The thermistor is preferably aligned either adjacent to or in between the resistor heaters in the case of a one resistor or two resistor set-up, respectively. By closely aligning these electronic elements, only a very thin air gap results between them. Furthermore, application of a thermal compound before assembling the fluidic with the electronic layer ensures good thermal contact between the fluidic component, resistor, and thermistor.

In some embodiments of the invention, vent resistors 70, 71 comprise a thick film 0805 package, although similar resistors may be used. In place of a resistor, a small gauge nichrome wire heating element, such as a 40 gauge nichrome wire may also be used.

In some embodiments of the invention, the microcontroller is a Microchip Technologies PIC16F1789. The microcontroller is preferably matched to the complexity of the fluidic system. For example, with multiplexing, the number of individual vents and heaters is commensurate with the number of microcontroller I/O lines. Memory size can be chosen to accommodate program size.

In certain embodiments of the invention, N-channel MOSFETs in the SOT-23 package operating in an ON-OFF mode are used to modulate current load to vent and heater resistors. Modulation signals are sent via the microcontroller. In alternative embodiments, a pulse-width-modulation scheme and/or other control algorithms could be used for more advanced thermal management of fluidics. This would typically be handled by the microcontroller and may require additional hardware and/or software features known to those skilled in the art.

Depending on the application, some embodiments comprise a device in which a small controlling docking unit or docking unit operates a smaller disposable unit comprising fluidic systems which come in contact with biological materials, referred to as the test cassette. In one such embodiment, the docking unit comprises the electronic components. Elimination of electric components from the disposable test cassette reduces costs and in some cases environmental impact. In another embodiment, some electronic components are included in both the docking unit and the test cassette. In this particular embodiment, the test cassette preferably comprises a low cost PCA or preferably a flexible circuit to provide some electrical functions such as temperature control, fluid flow control and temperature sensing, which are energized, controlled and/or interrogated by the docking unit through an appropriate interface. As described above, the electronic functions of such a device is preferably split into two separate subassemblies. Disposable cassette 2500 preferably comprises a rear surface designed to interface with resistive heating and sensing elements of the docking unit. Materials comprising the rear face of the test cassette are preferably selected to provide suitable thermal conductivity and stability while enabling fluid flow control via vent rupture. In some embodiments, the rear face of the test cassette or a portion thereof comprises a flexible circuit manufactured on a substrate such as polyimide. Flexible circuits can be employed to provide low cost resistive heating elements with low thermal mass. Flexible circuit substrates may preferably be placed in direct contact with solutions present in the fluid network of the test cassette to enable highly efficient and rapid heating and cooling. Connector 810 as shown in FIG. 8 preferably provides current to the resistive heaters along with a power and signal line to the optional thermistor(s).

If flexible circuit 799 is used, one or more IR sensors located in the docking unit can monitor the temperature of the heated chambers (e.g. amplification or detection chambers) by reading the signal through a window in backing 805 or directly off the rear of flexible circuit 799. Optionally, thermistors on the PCA or flexible circuit 799 can be used to monitor the temperatures. Optionally performing a weighted average of the outputs of the IR sensors and thermistors improves the correlation between the readings and the fluid temperature in the cassette. In addition, sensors can also detect ambient temperature, enabling the system to correct for it to ensure that the sample fluid equilibrates rapidly to the desired temperatures.

Figure 33:
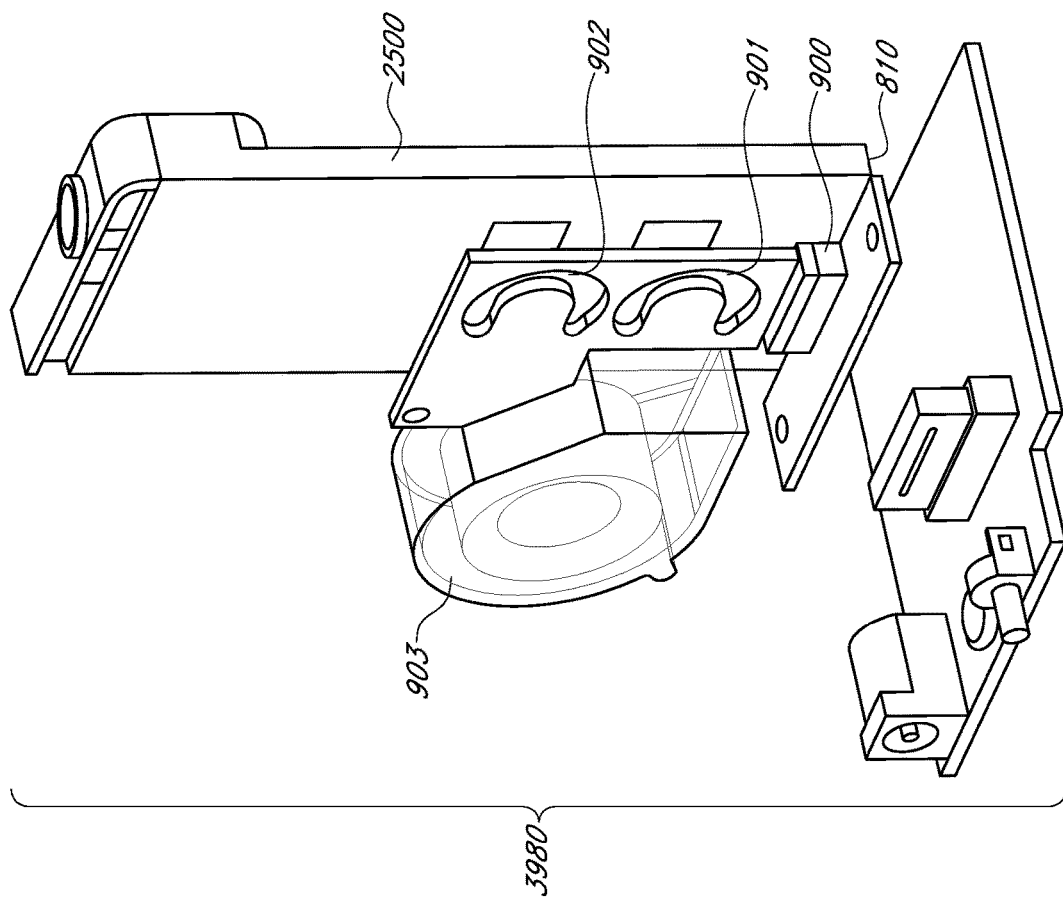
FIG. 33 shows a reusable subassembly for a docking unit of the present invention.

Referring now to FIG. 33, the docking unit preferably comprises a reusable component subassembly 3980 comprising the microcontroller, MOSFETs, switches, power supply or a power jack and/or battery, optional cooling fan 903, optional user interface, infrared temperature sensors 901, 902 and connector 900 compatible with connector 810 of cassette 2500. When the subassemblies are mated via connectors 810 and 900, the docking unit preferably supports disposable cassette 2500 in a substantially vertical or near-vertical orientation. Although a substantially vertical orientation is preferable in some of the embodiments described herein, similar results may be obtained if the device is operated at a tilt, especially if certain pathways are coated to reduce the wetting angle of solutions used.

Another embodiment of the device may be used in order to minimize the operational costs, by reducing the cost of the consumable part of the system by eliminating all electronic circuitry located on the disposable part. The microcontroller, heaters, sensors, power supply, and all other circuitry are located on multiple PCA's and electrically connected to each other via high conductor count industry standard ribbon cables. A display may also be added to aid the user in operation of the device. An optional serial control port may also be utilized in order to allow the user to upload changes in test parameters, and to monitor the progress of any testing. One version of this embodiment comprises five different PCA's. The Main Board PCA contains the control circuitry, serial port, power supply, and connectors to connect to the other boards in the system. The Heater Board PCA contains the heating resistor elements, temperature sensors, and vent burn heating elements. In order to facilitate the thermal interface between this heater board and the disposable fluidic cassette, this board is mounted on a spring loaded carrier which is moved towards the backside of the fluidic cassette by the closing action of the lid, until contact with the fluidic cassette is made. A thin thermally conductive heating pad is affixed on top of the chamber heater resistors and temperature senor, improving heat transfer between the heater board and the fluidic cassette. A durable vent burning heating element may be realized using nichrome wire wrapped around a small ceramic carrier. The IR sensor board PCA is mounted some small distance from the opposite side of the cassette and is used for monitoring the heating chamber temperatures. This allows closed loop temperature control of the heating and cooling process, and accommodates ambient temperature variations. Also mounted on the IR sensor board are multiple reflective sensing optical couplers which allow the sensing of the presence of the cassette, and may be used to identify the type of cassette denoted by the configurable reflective pattern located on the cassette. A Display Board PCA may be located approximately behind the IR Board to allow the user to see the display from the front of the device. A final PCA, the shutter board is located across from the top edge of the cassette and contains a switch and reflective optical coupler which is used to sense whether or not the cassette has already been used, and when the lid closes, holding the cassette in place for testing.

System cooling is optionally augmented using a fan such as a muffin style fan which is turned on by the microcontroller only during the cooling phase of testing. A system of vents is preferably used to direct cooler outside air against the heating chambers and expel it out the sides of the device.

In order to provide a complete sample-to-result molecular test, any of the above embodiments of the invention may be interfaced to a sample preparation system 1300 that provides nucleic acids as output to sample chamber 1402. This has been demonstrated using the sample preparation technology described in International Publication No. WO 2009/137059 A1, entitled "Highly Simplified Lateral Flow-Based Nucleic Acid Sample Preparation and Passive Fluid Flow Control". An embodiment of the resulting integrated device is illustrated in FIG. 15 and FIG. 16.

Docking Unit

Figure 18A:
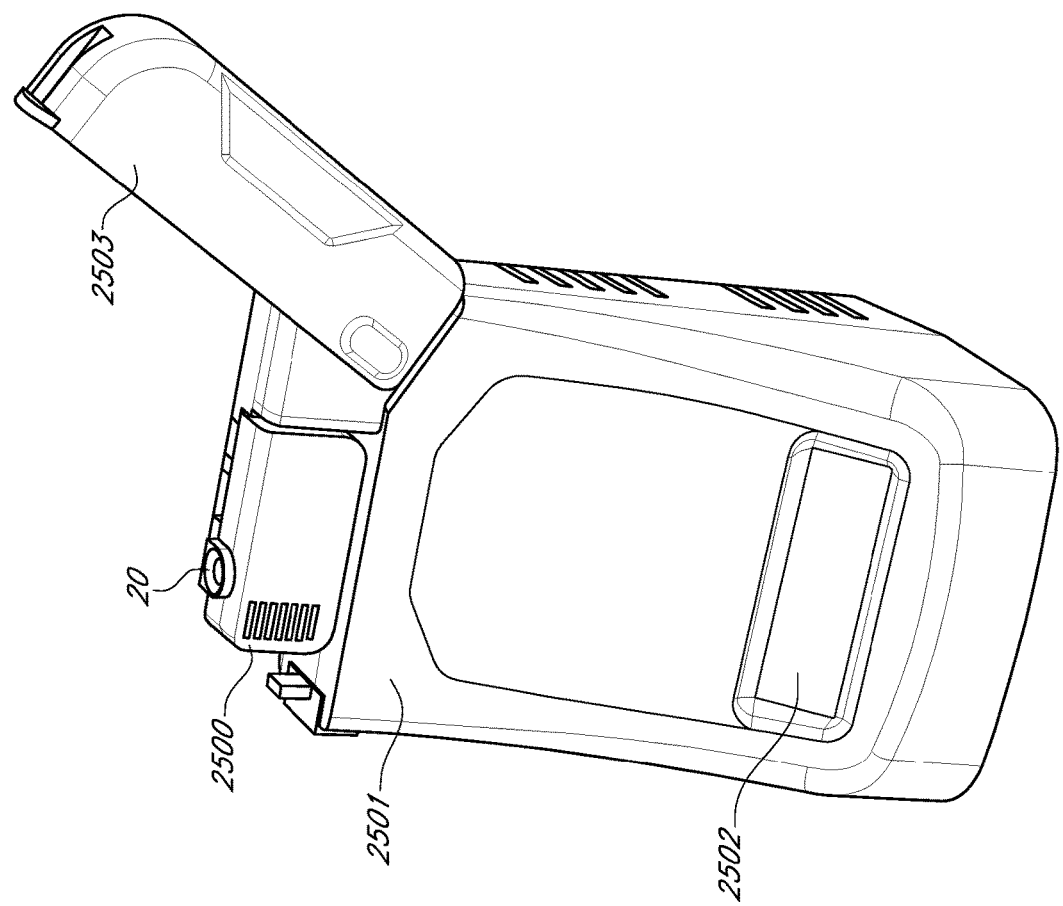
FIG. 18A is a drawing of an embodiment of a docking unit of the present invention shown with the lid in the open position and a test cassette inserted.
Figure 18B:
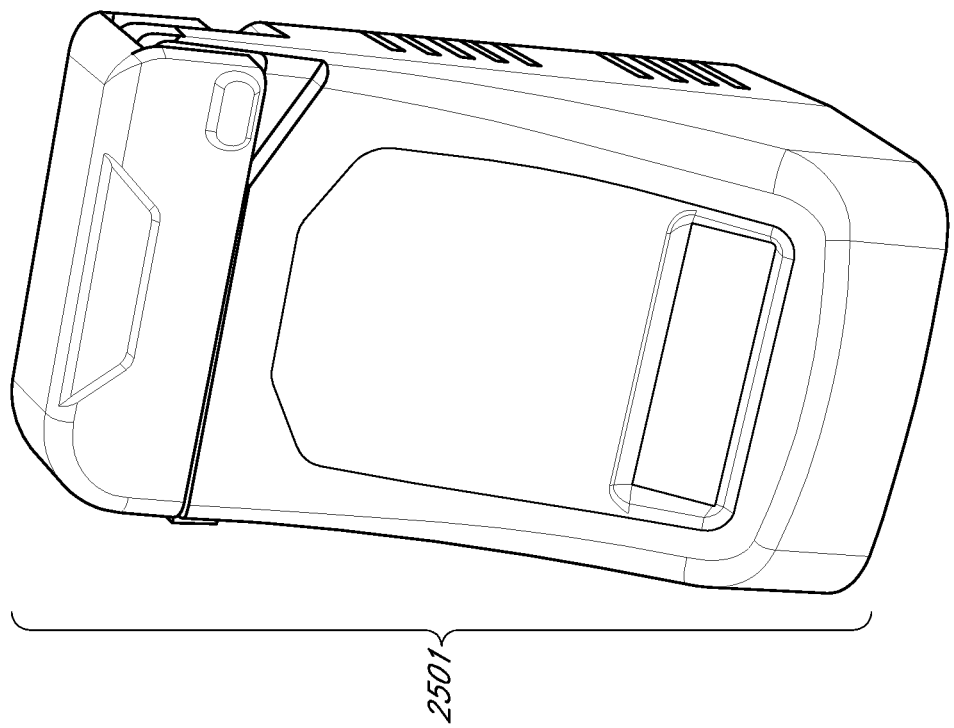
FIG. 18B is a drawing of the docking unit shown with the lid in the closed position.
Figure 19:
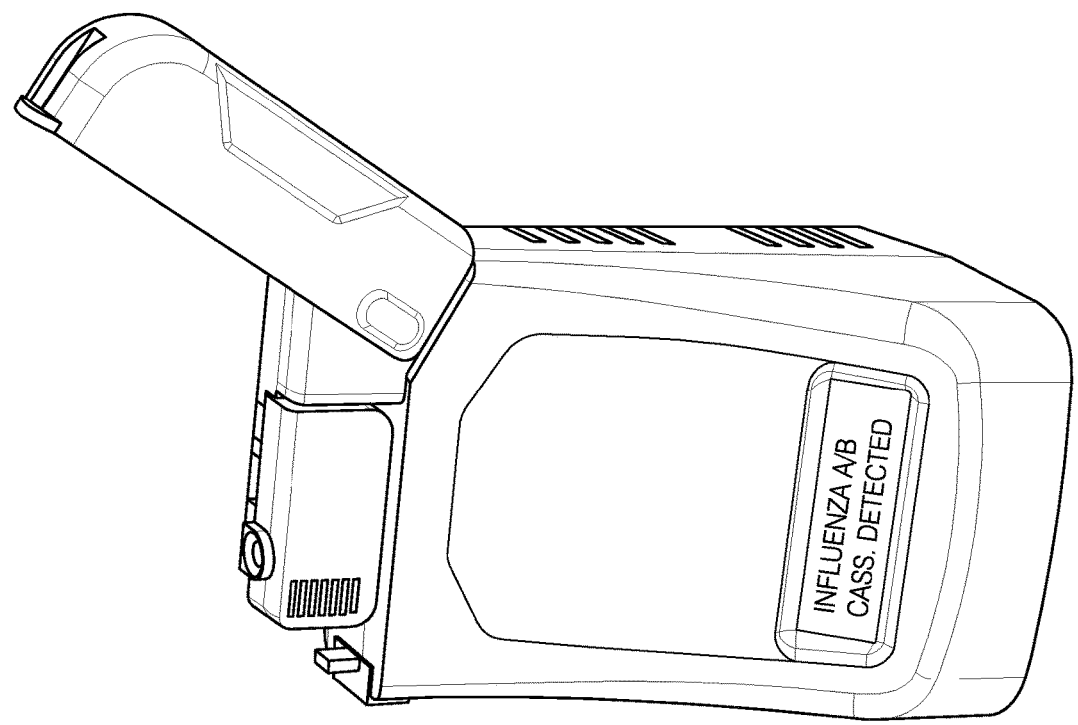
FIG. 19 is a photograph of one embodiment of the docking unit shown with the lid in the open position and a test cassette inserted. The LCD display indicates detection of the insertion of an influenza A/B test cassette.

The reusable docking unit comprises requisite electronic components to achieve test cassette functionality. Various docking unit embodiments have been invented to interface with corresponding variations in test cassette design. In one embodiment, the docking unit, shown in FIG. 18 and FIG. 19, comprises all electronic components required to run a test, eliminating the need for electronic components in the test cassette. Referring now to FIG. 18, prior to sample addition, cassette 2500 is inserted into docking unit 2501. Docking unit 2501 comprises a display such as LCD display 2502 to communicate information such as test protocols and test status to the user. Following cassette insertion into docking unit 2501, sample is introduced to sample port 20 of cassette 2500 and docking unit lid 2503 is closed to initiate the test. A docking unit with inserted test cassette is shown in FIG. 19, and Docking unit 2501 with lid in the closed position is illustrated in FIG. 18B.

Figure 20:
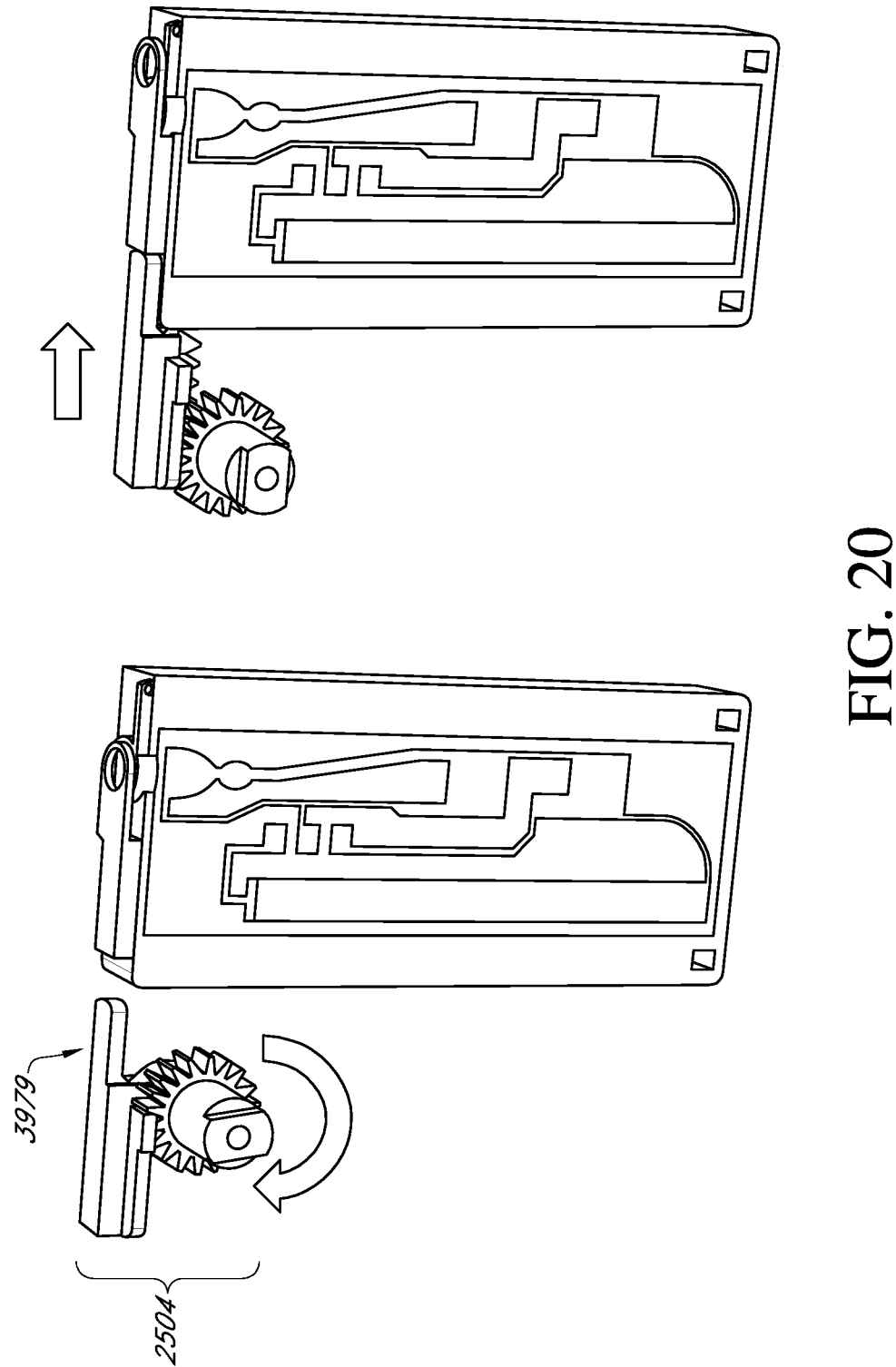
FIG. 20 illustrates an embodiment of a cassette sealing mechanism of the present invention.
Figure 21A:
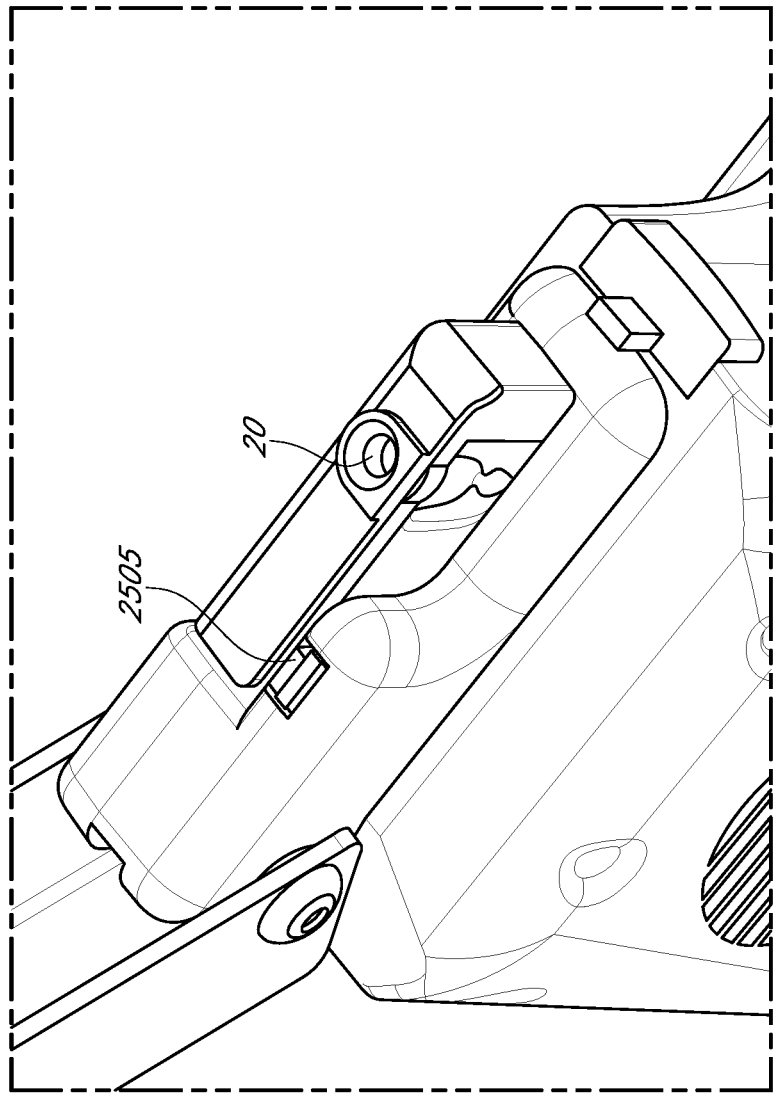
FIG. 21A is a drawing of the cassette seal sensor placement within the docking unit with an inserted cassette with the seal in the open position.
Figure 21B:
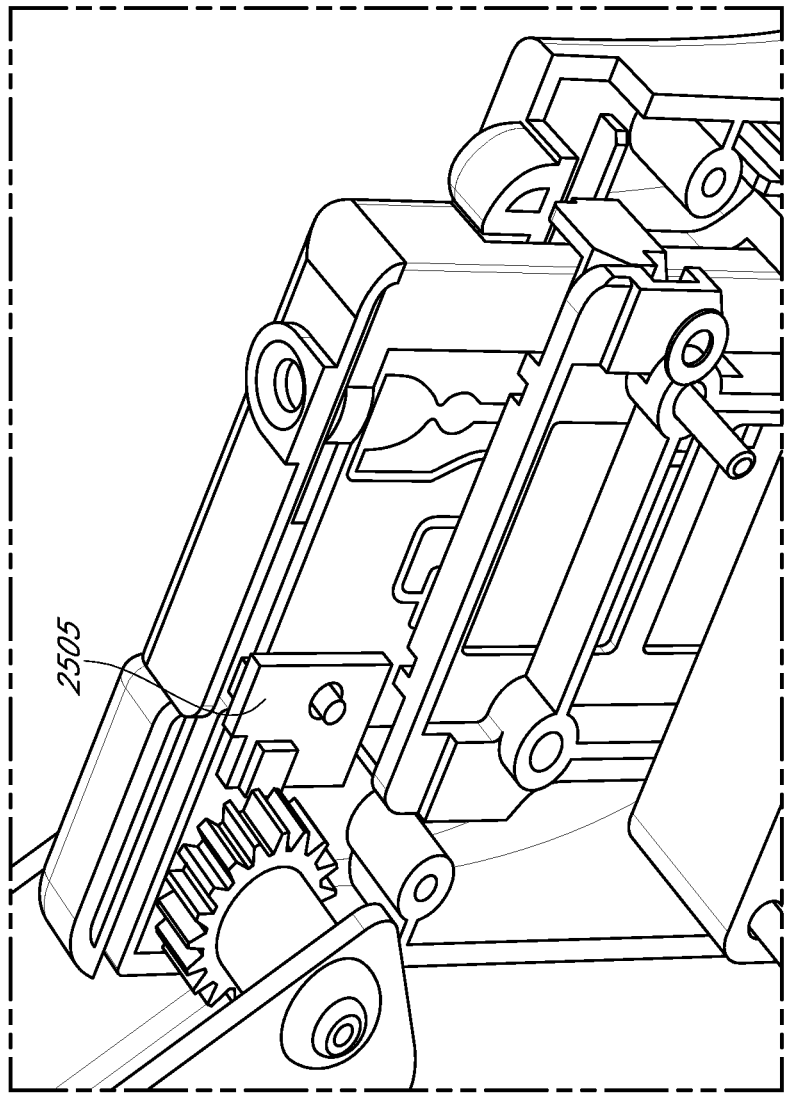
FIG. 21B is a cutaway drawing of the cassette seal sensor placement within the docking unit with an inserted cassette with the seal in the open position.
Figure 21C:
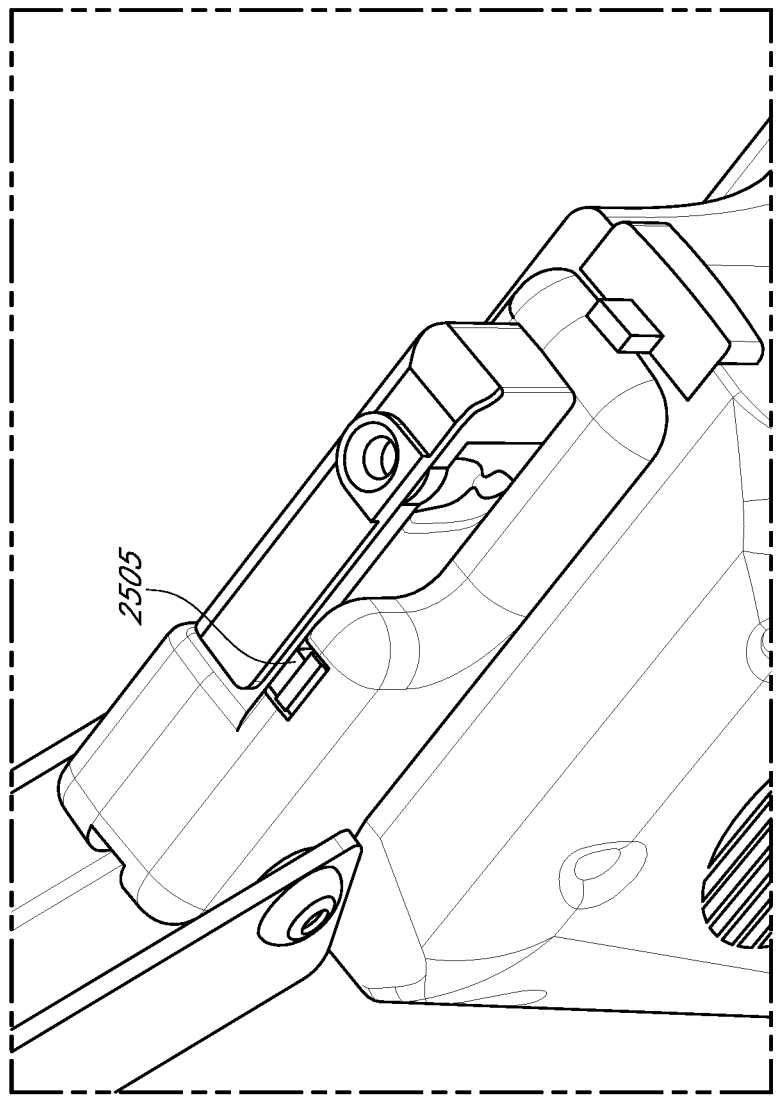
FIG. 21C is a drawing of the cassette seal sensor placement within the docking unit with an inserted cassette with the seal in the closed position.
Figure 21D:
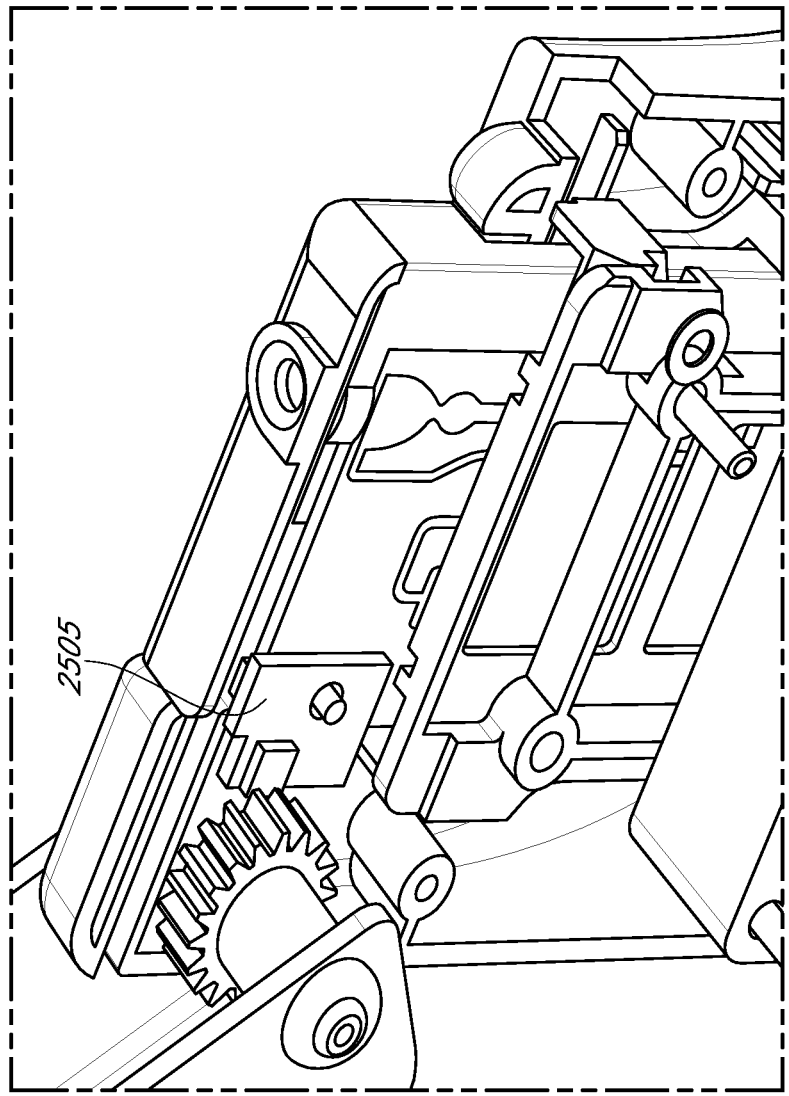
FIG. 21D is a cutaway drawing of the cassette seal sensor placement within the docking unit with an inserted cassette with the seal in the closed position.
Figure 22:
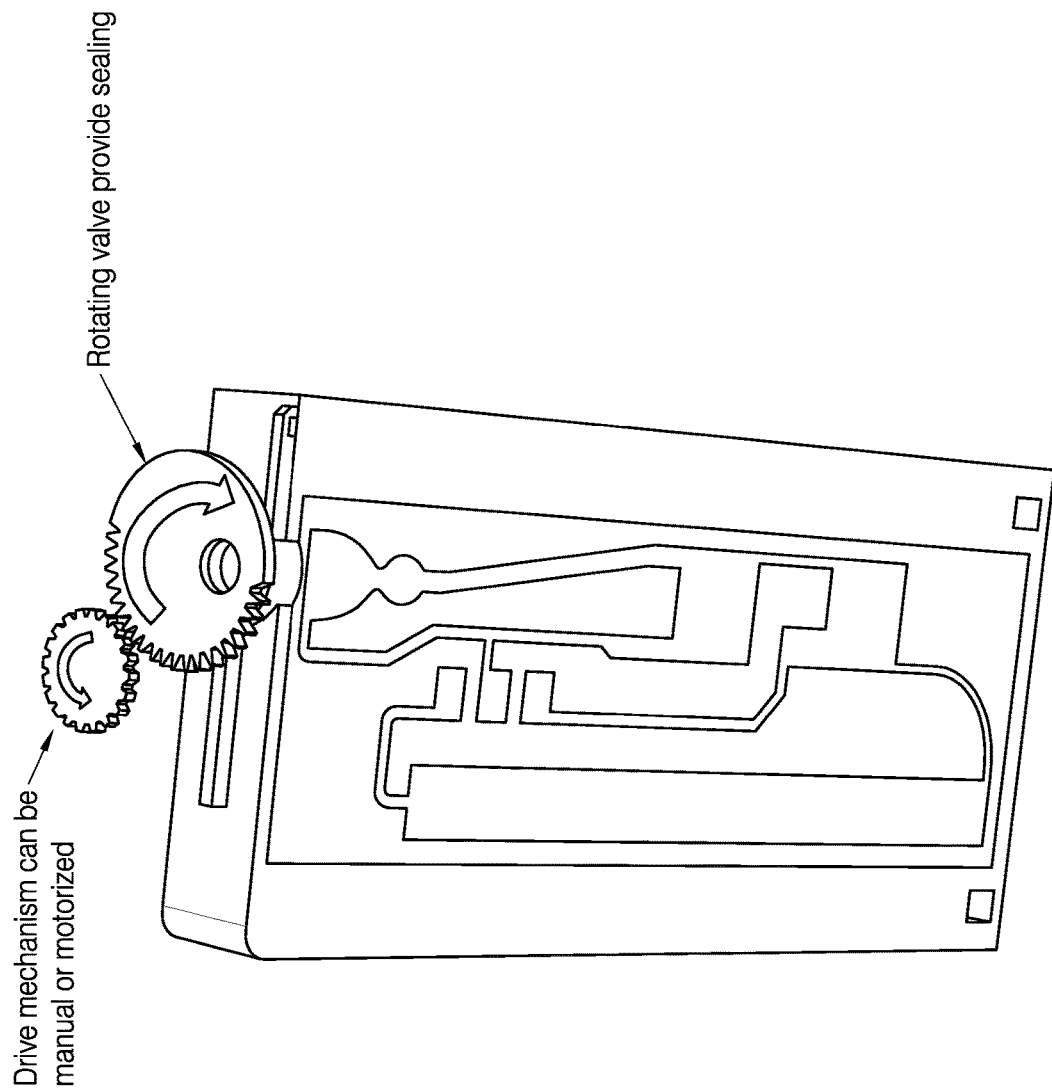
FIG. 22 is a drawing of an embodiment of the cassette sealing mechanism wherein a drive gear is employed to mediate seal closure using a rotating valve.
Figure 23A:
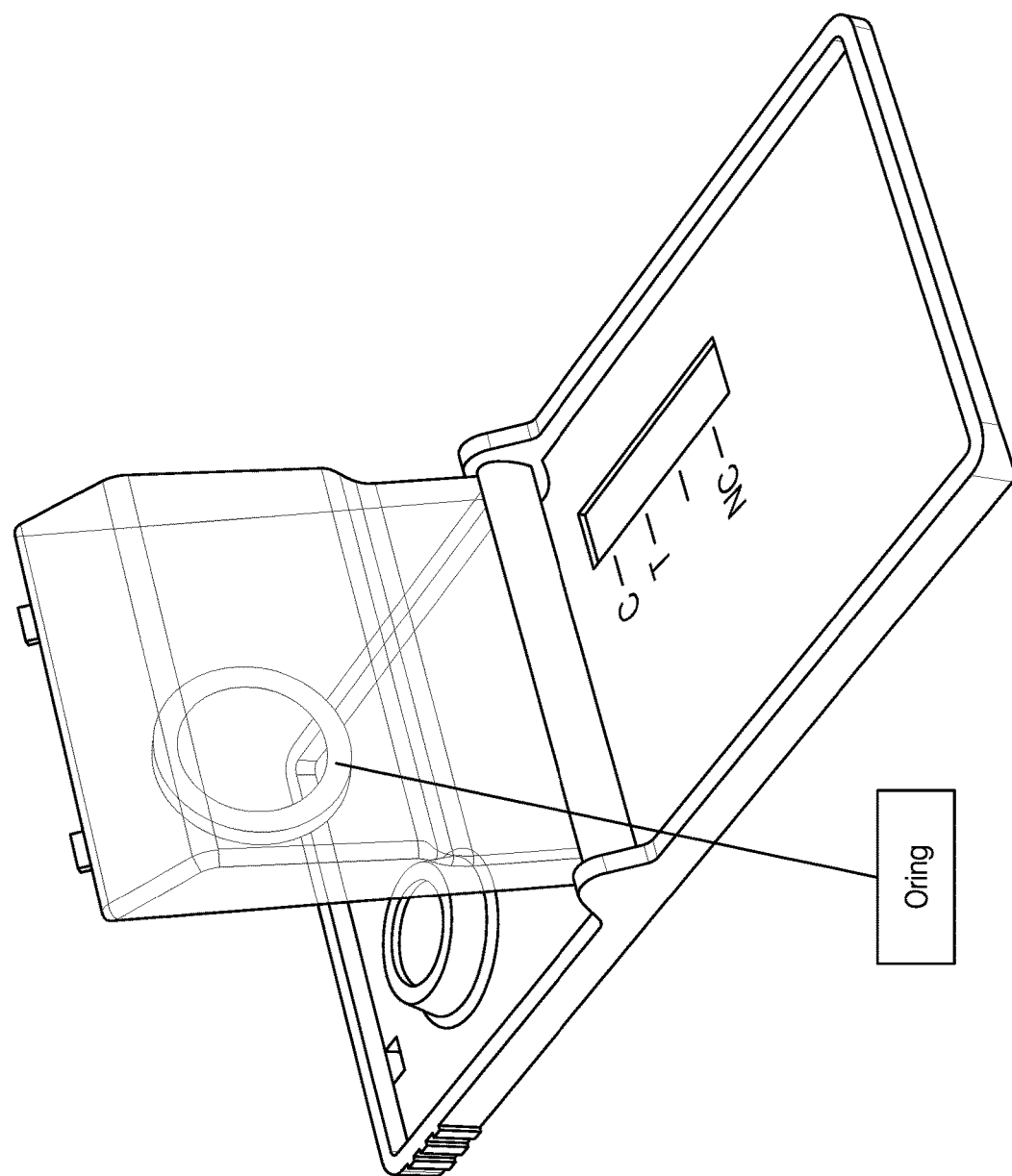
FIG. 23A is a drawing illustrating an embodiment of the test cassette wherein the lid is a hinged lid comprising an o-ring seal and a vacant air volume that serves as an expansion chamber. In this drawing the lid is in the open position.
Figure 23B:
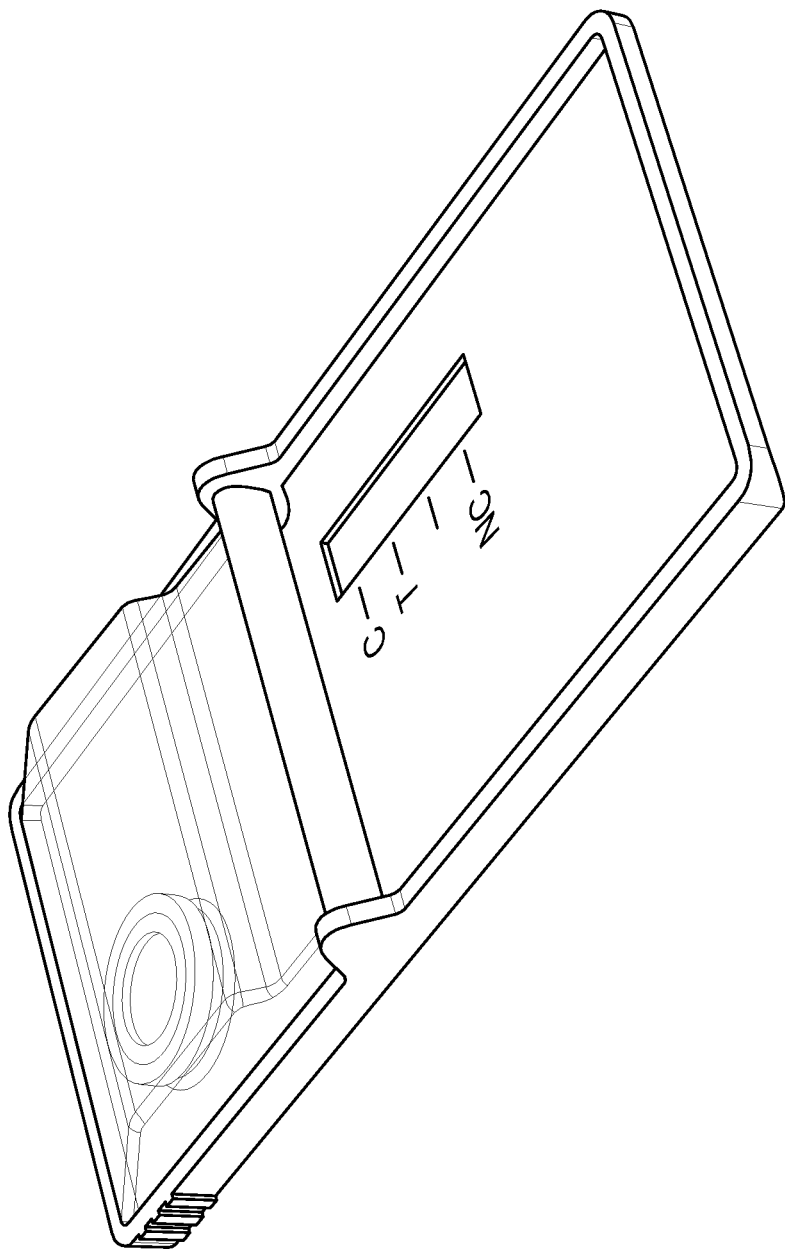
FIG. 23B is a drawing showing the lid in the closed position, where the o-ring forms a hermetic seal with the rim of the sample port.

In some embodiments of the docking unit, a mechanism is incorporated into the hinge of lid 2503 which moves sliding seal 91 of the test cassette to the closed position. A sealed test cassette is helpful to ensure amplified nucleic acids remain contained within the test cassette. Referring now to FIG. 20, either a manual or an automated method may be employed to slide a valve over the sample port to seal the cassette. In some embodiments the slide seals the sample port by engaging an o-ring. The expansion chamber cover holds the valve slide in place above the sample port o-ring. The seal is moved into position by a servo motor or by a manual action such as closing the reusable docking unit lid, which in turn actuates a mechanism to close the cassette seal. In the pictured embodiment rack and pinion mechanism 2504 employs slide seal actuator 3979 to move sliding seal 91 to the closed position. Rack and pinion mechanism 2504 may be motorized or moved by the action of closure of docking unit lid 2503 through a mechanical coupling to lid hinge. Optionally, a sensor such as optical sensor 2505 may be situated to interrogate the position of sliding seal 91 to ensure proper seal placement prior to assay initiation as illustrated in FIG. 21. The optical sensor detects the state (i.e. position) of the cassette sample port seal. The optical sensor allows the docking unit to be programed to detect accidental insertion of a previously used test cassette and to detect the successful closure of the test cassette seal. An error message indicating seal malfunction may be displayed on display 2502 and the test program aborted should sensor 2505 fail to detect seal closure. In other embodiments of the test cassette and docking unit, the sealing mechanism may comprise other means of mechanically sealing the chamber such as a rotating valve as illustrated in FIG. 22. In yet another embodiment, a test cassette seal may be placed in a hinged cassette lid placed such that insertion into the docking unit is not possible without first closing the cassette lid and thus seating the seal. In this embodiment, sample is added to the test cassette prior to insertion into the docking unit. A test cassette comprising a hinged lid with seal is illustrated in FIG. 23. In general, after the cassette is inserted into the docking unit and the sample is loaded into the cassette, it is preferable that closing the lid of the docking unit both seals the cassette automatically and initiates the assay, preferably without the use of servos or other mechanical devices.

Figure 24A:
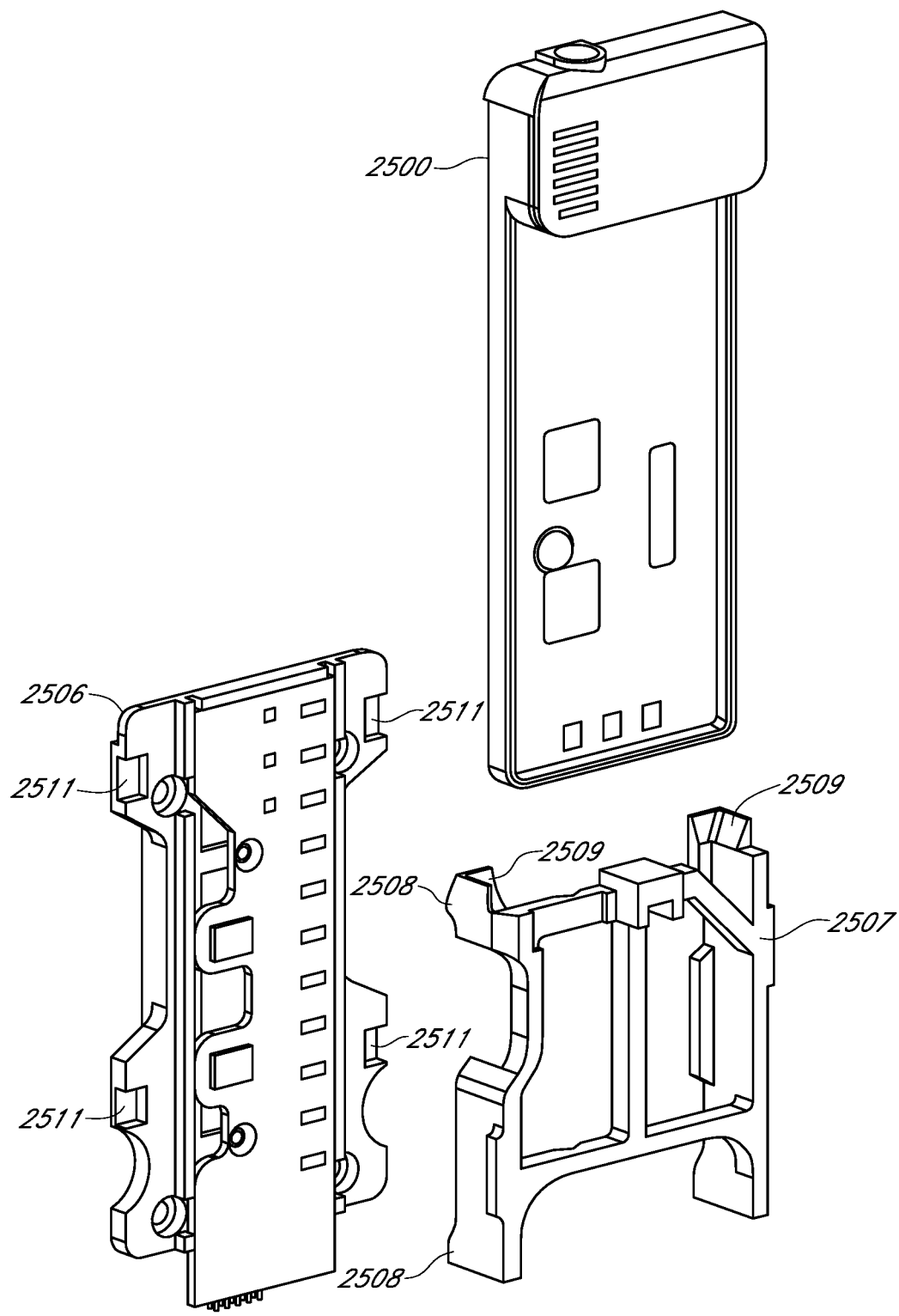
FIG. 24A is an exploded view of the heater board and test cassette holder components of the docking unit forming the test cassette receiving subassembly.
Figure 24B:
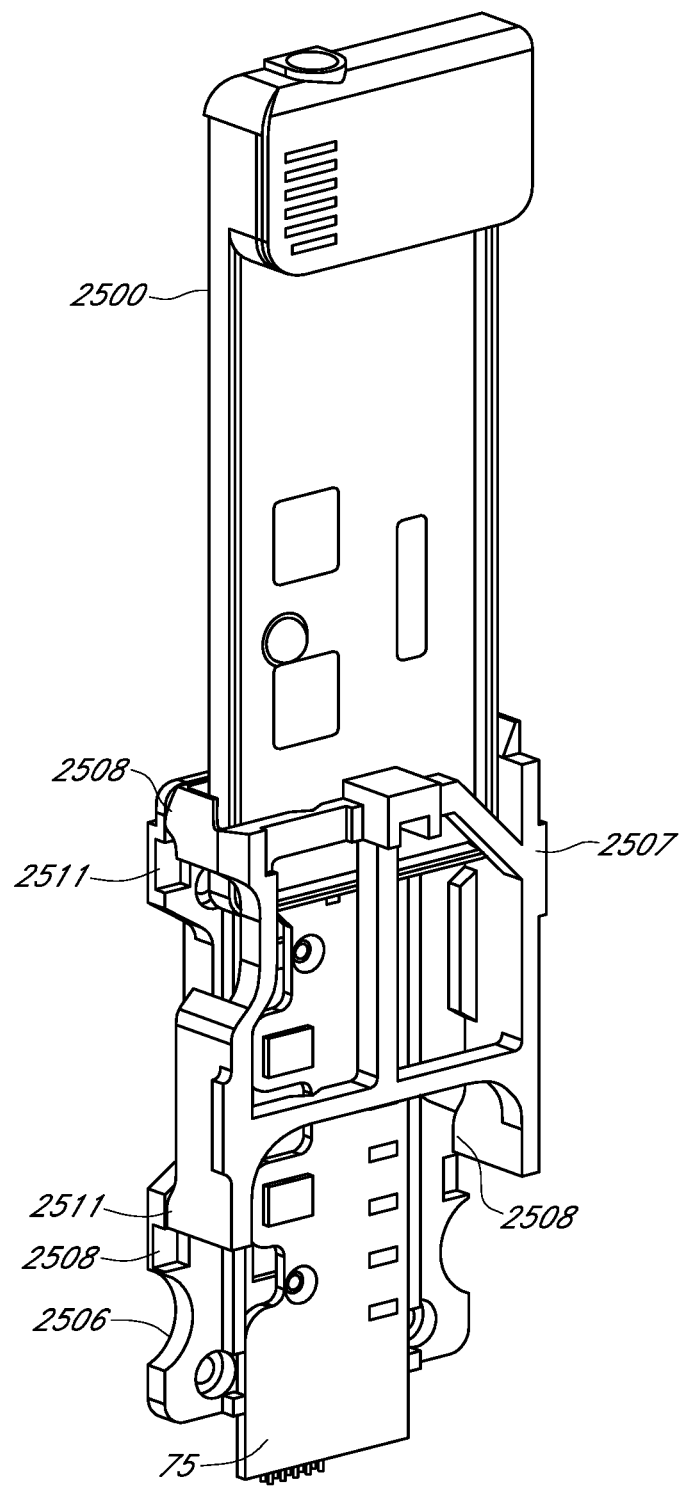
FIG. 24B is a drawing of an embodiment of the test cassette receiving subassembly of the docking unit.
Figure 25:
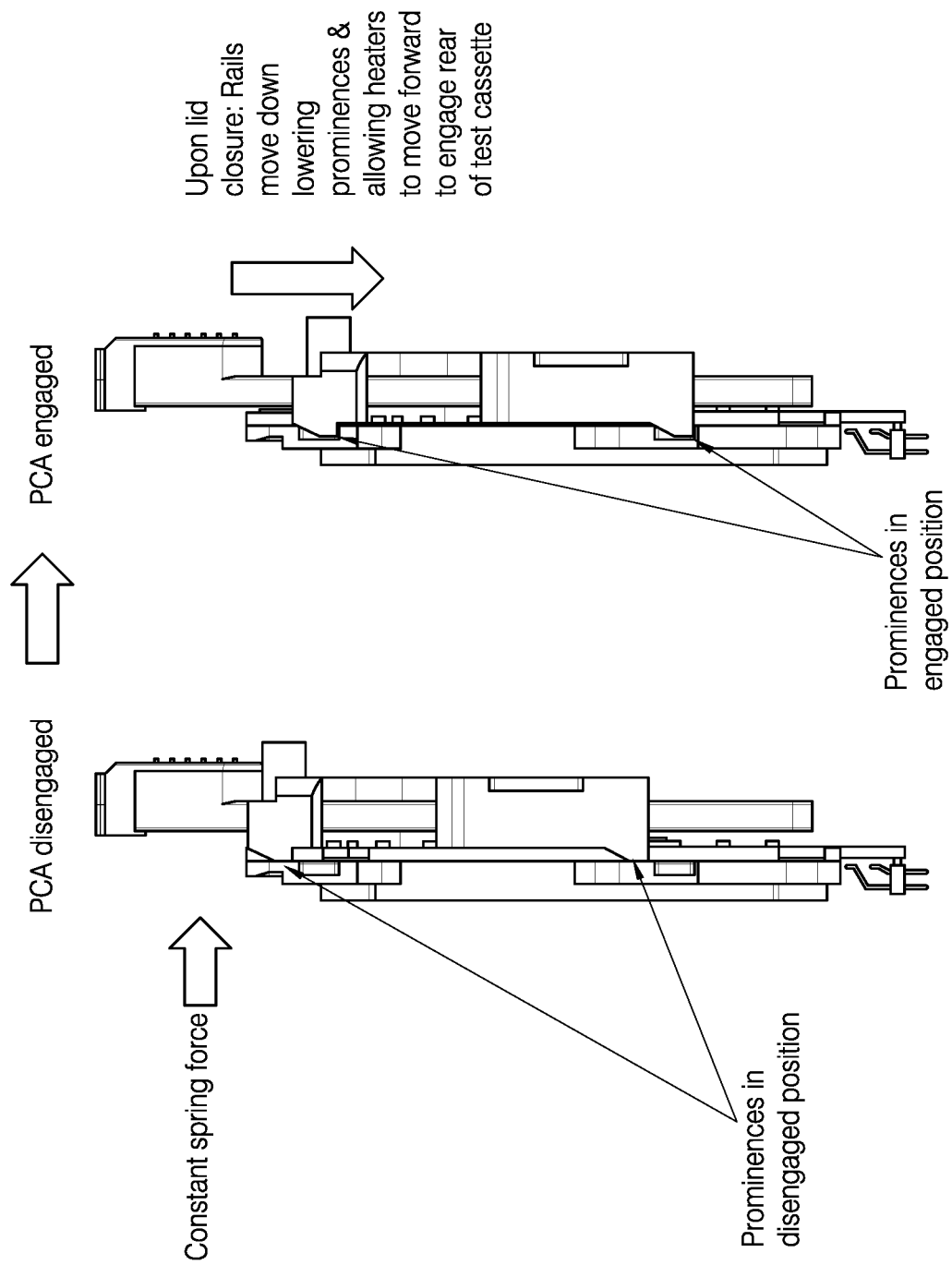
FIG. 25 is a slide view of the test cassette holder and heater board mounting system in the engaged and disengaged positions.

In some docking unit embodiments a set of components preferably facilitate proper test cassette insertion while ensuring electronic components that must interface with the test cassette do not physical interfere with cassette insertion, yet form a reliable thermal interface during testing. These components form a mechanism for holding PCA 75 away from the cassette insertion path until closure of lid 2503. Referring now to FIG. 24, within the docking unit the heater board is mounted on PCA holder 2506, which preferably serves as a low thermal mass scaffold, while the test cassette is loaded into a low thermal mass cassette holder 2507, wherein rails 2509 guide the cassette into the docking unit and hold it in the correct position, such as parallel to the heater board surface, for interfacing with PCA 75 mounted on PCA holder 2506. In the lid open position, prominences 2508 on cassette holder 2507 interfere with PCA holder 2506 to maintain an open path along rails 2509 for cassette insertion. Preferably, a sloped surface spans the distance between the surface of prominences 2508 and the lower elevation of component 2507 to facilitate smooth movement of prominences 2508 into depressions 2511 on PCA holder 2506 during closure of lid 2503. Upon closure of the docking unit lid, prominences 2508 engage with depressions 2511, thereby moving the heater board mount closer to the rear surface of test cassette 2500. Closure of lid 2503 exerts downward force on cassette holder 2507 thereby moving cassette holder 2507 to a position where prominences 2508 come to rest in depressions 2511 resulting in movement of PCA holder 2506 such that PCA 75 is pressed against the rear of cassette 2500. Preferably PCA holder 2506 is under constant force, such as spring force, to enable the exertion of reproducible pressure against the rear of the cassette by PCA 75 after lid closure. Placement of PCA 75 against the rear of cassette 2500 forms the thermal interface which conducts heat from resistive heater elements on the PCA to the temperature controlled chambers and vents of the test cassette. Preferably components 2506 and 2507 are constructed to contribute minimal thermal mass to the system and provide access to test cassette surfaces for cooling apparatus, such as fans, and temperature monitoring by sensors, such as infrared sensors. After lid closure the heater board is thus preferably pressed firmly against the rear of the test cassette, forming a thermal interface that enables the microheaters on the heater board to heat solutions in the fluid chambers of the test cassette and to melt the thermally labile vent films of the test cassette, preferably in accordance with microcontroller or microprocessor control. FIG. 25 illustrates the cassette-PCA interfacing mechanism in cross-section in both disengaged (lid open) and engaged (lid closed) positions.

Figure 26:
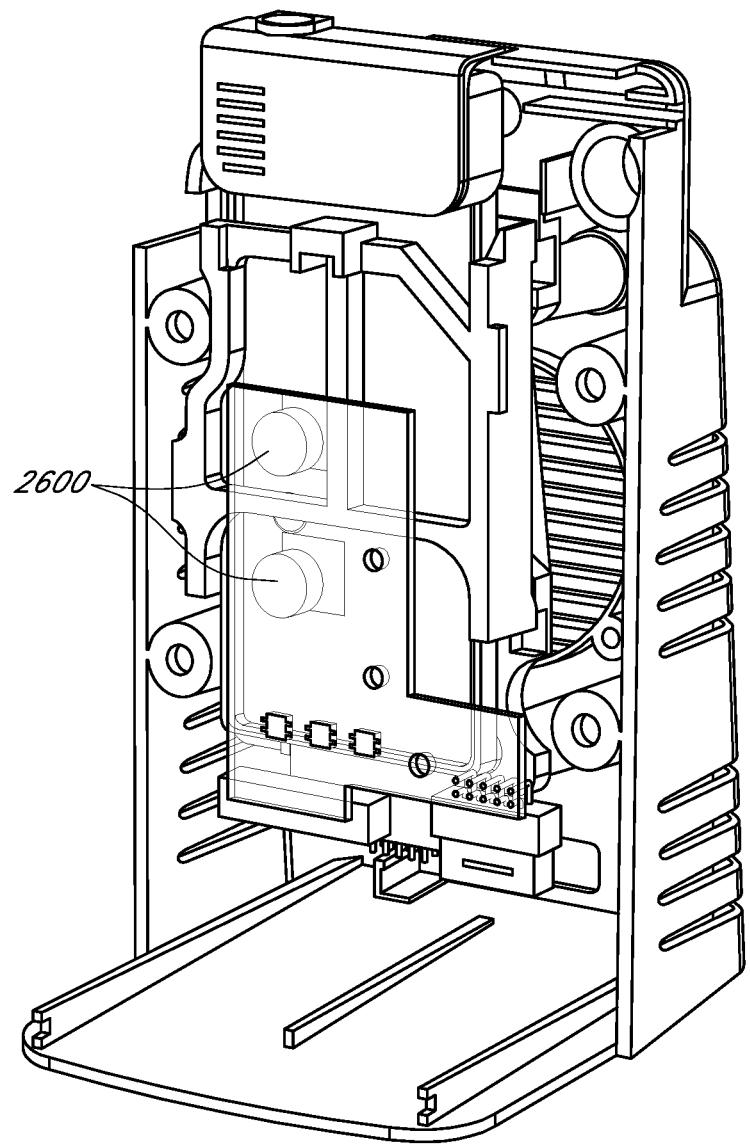
FIG. 26 is a drawing depicting the placement of infrared temperature sensors in one embodiment of the docking unit to monitor the temperature of first and second heated fluidic chambers.
Figure 27A:
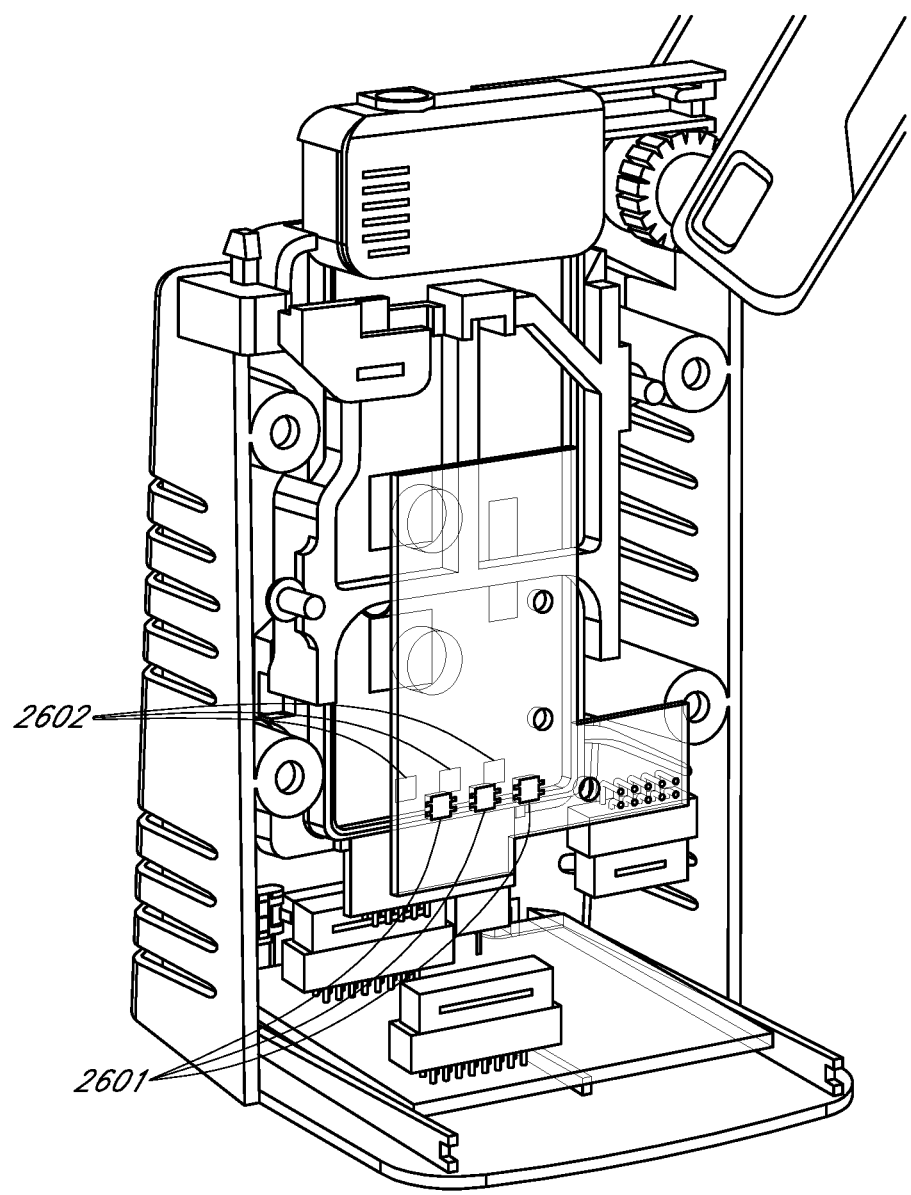
FIG. 27A is a drawing showing optical sensor placement within an embodiment of the docking unit to allow reading of a barcode located near the bottom of the test cassette.
Figure 27B:
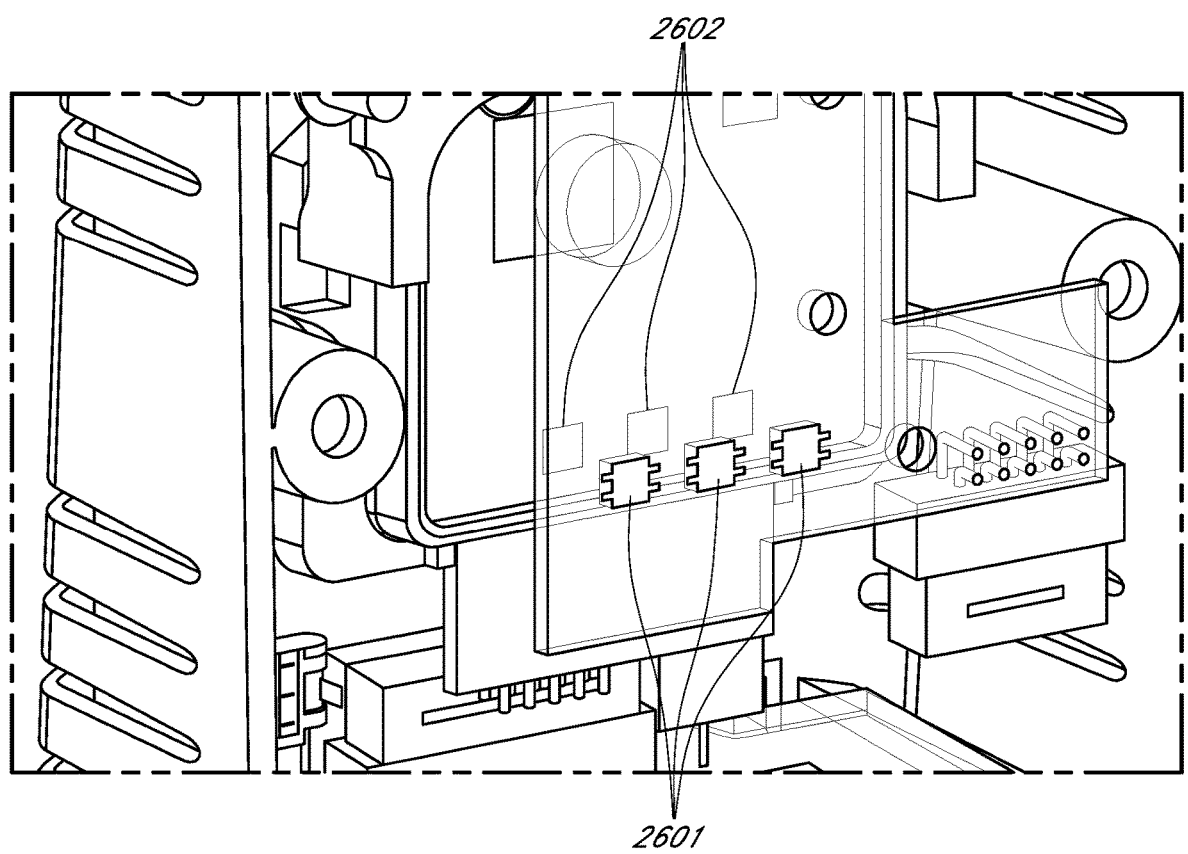
FIG. 27B is a detail of FIG. 27A.

In some embodiments, the docking unit comprises additional sensors for such applications as temperature sensing, detecting the presence of or removal of a test cassette and detecting specific test cassettes for enabling automated selection of testing parameters. Referring now to FIG. 26, infrared sensors 2600 detect the temperature of the test cassette in regions overlying temperature controlled chambers, such as chambers 30 and 90. The sensors enable the collection of temperature data in addition to or in lieu of temperature data collected by PCA 75 localized temperature sensors, such as sensor 110. Optical sensors may optionally but preferably be employed to detect specific test cassettes to identify cassettes for specific diseases or conditions and allow automated selection of temperature profiles suitable for a specific test. Referring now to FIGS. 27A and 27B, an optical sensor or optical sensor array such as optical senor array 2601 may be employed in conjunction with barcode or barcode-like features 2602 on the test cassette to determine the type of test cassette and to confirm complete insertion and correct seating of the test cassette. Sensor array 2602 in concert with sensor 2505 may be employed to detect the insertion of a previously used test cassette by detecting a closed seal prior to lid closure. The docking unit may comprise sensors to detect the type of test cassette inserted into the docking unit and/or to confirm the correct insertion, positioning, and alignment of the cassette within the docking unit. Detection of an influenza A/B test cassette is illustrated in the docking unit and test cassette system depicted in FIG. 19. The docking unit can preferably also read a barcode or other symbol on each cassette and change its programming in accordance with stored programs for different assays.

Figure 28A:
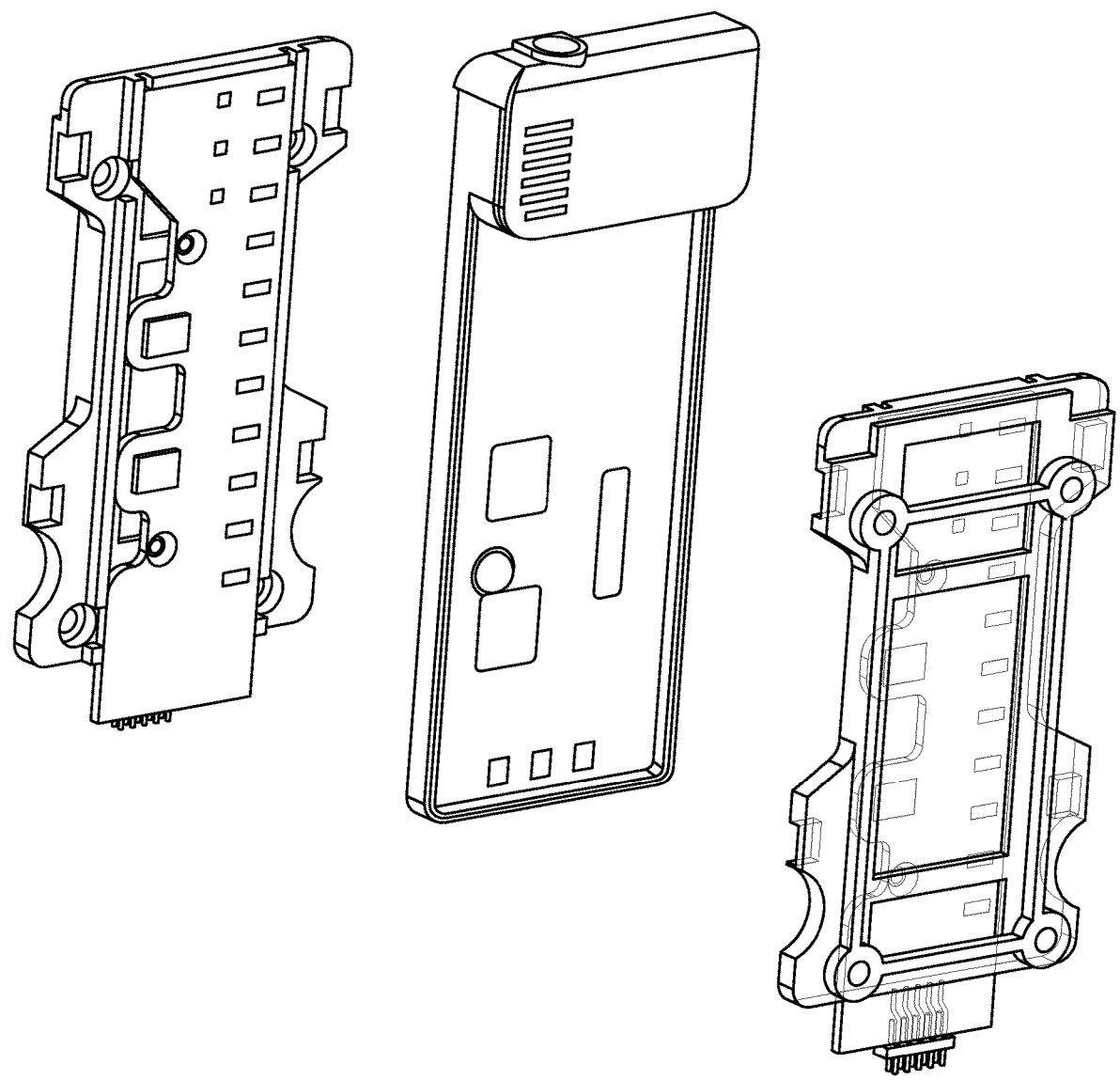
FIGS. 28A and 28B are exploded and assembled drawings, respectively, of a double heat board configuration wherein the test cassette is sandwiched between two heater board assemblies.
Figure 28B:
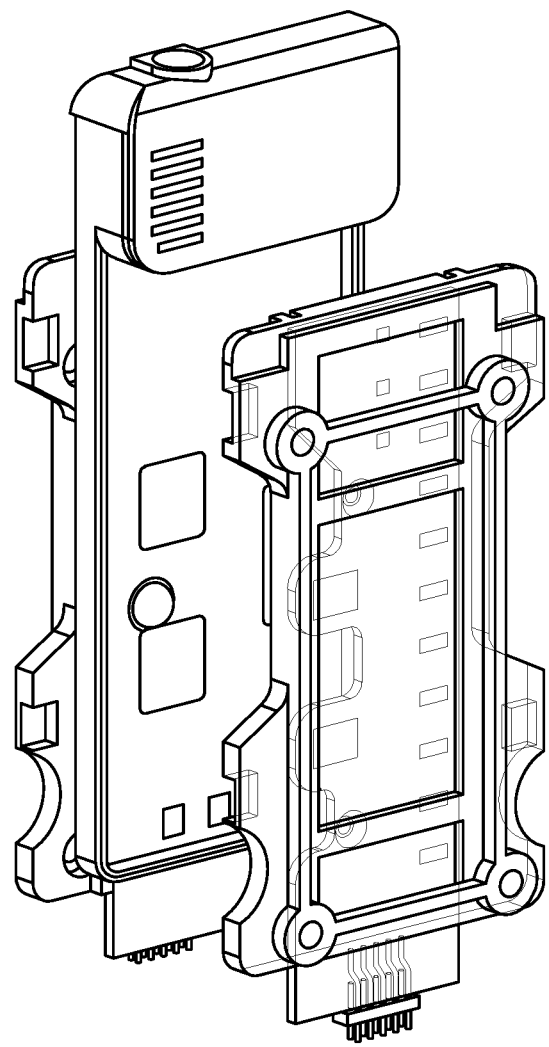

In some embodiments of the invention it is desirable to heat both sides of a test cassette. A dual heater PCA configuration wherein the test cassette is inserted between two heater PCAs is depicted in FIGS. 28A and 28B.

Figure 29A:
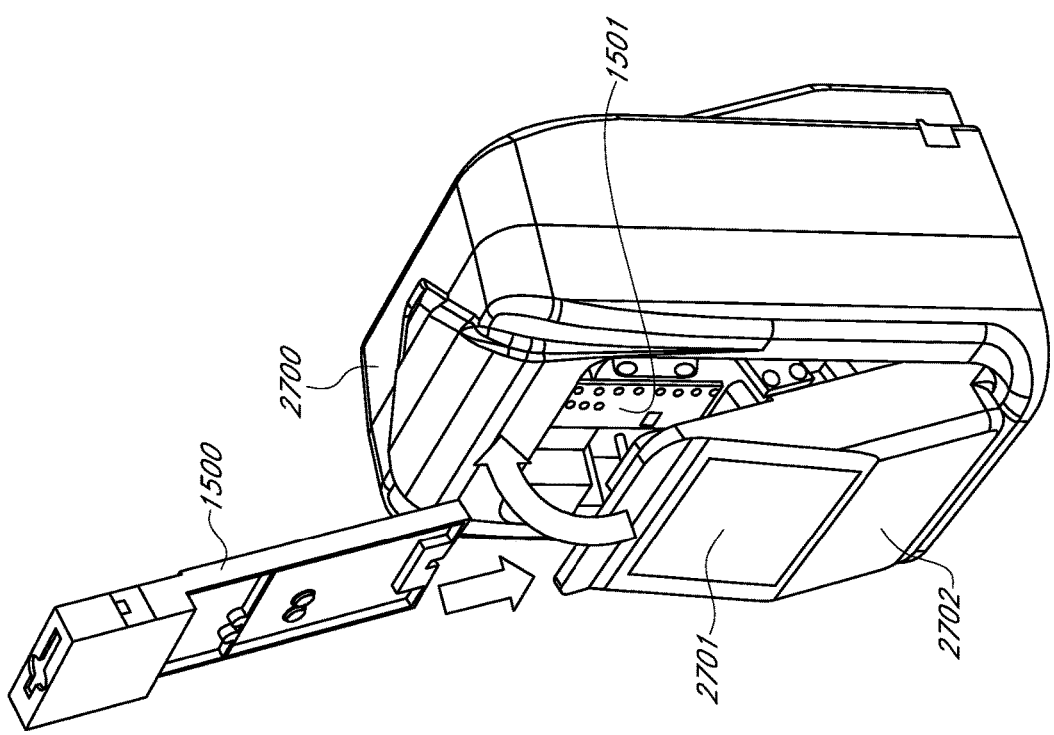
FIGS. 29A and 29B are solid and transparent drawings, respectively, of a docking unit embodiment wherein a pivoting door is used to receive a test cassette. Closure of the pivoting door brings the rear of the test cassette into contact with the heater board mounted within the docking unit.
Figure 29B:
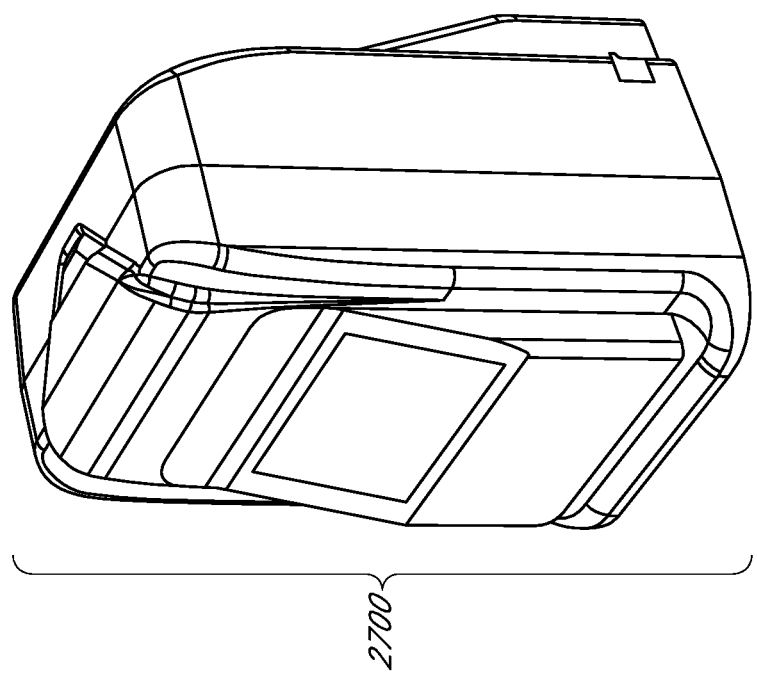
Figure 30A:
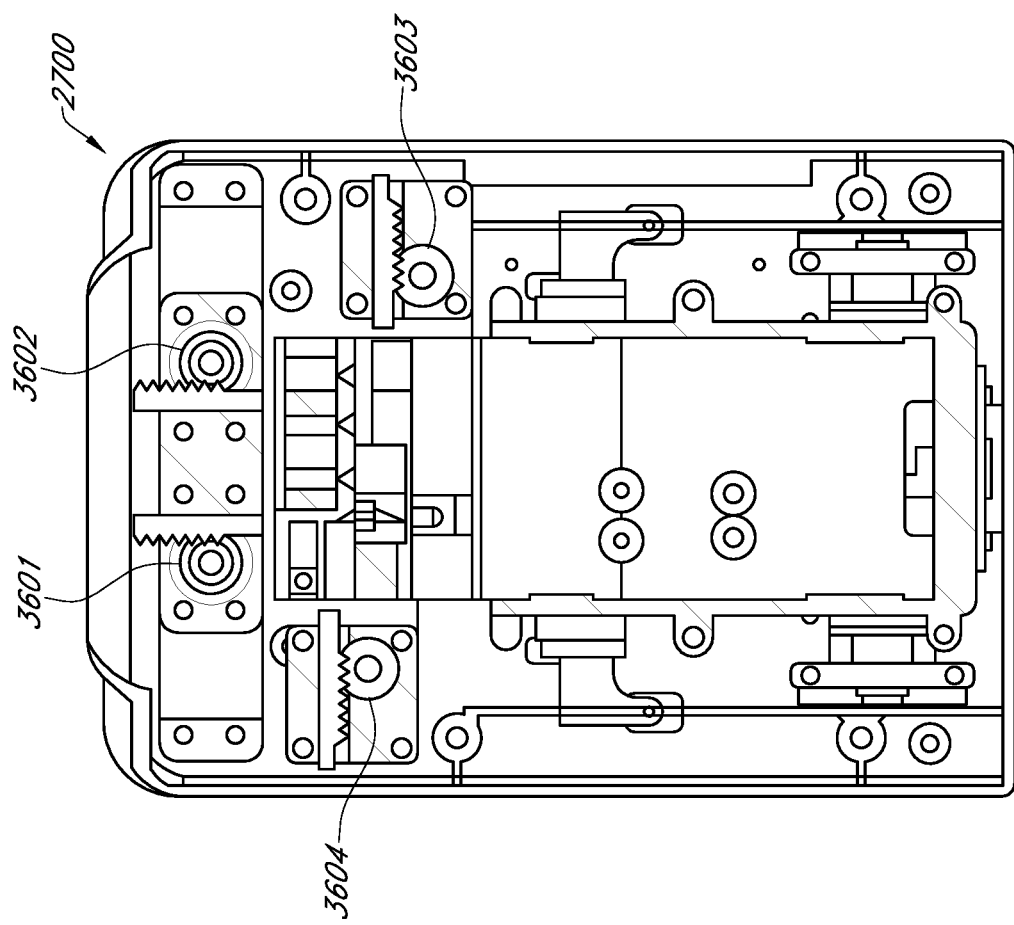
FIGS. 30A and 30B are front and side cutaway views respectively of the internal components of a docking unit comprising servo motors for actuating sample preparation and an optical system for test results collection.
Figure 30B:
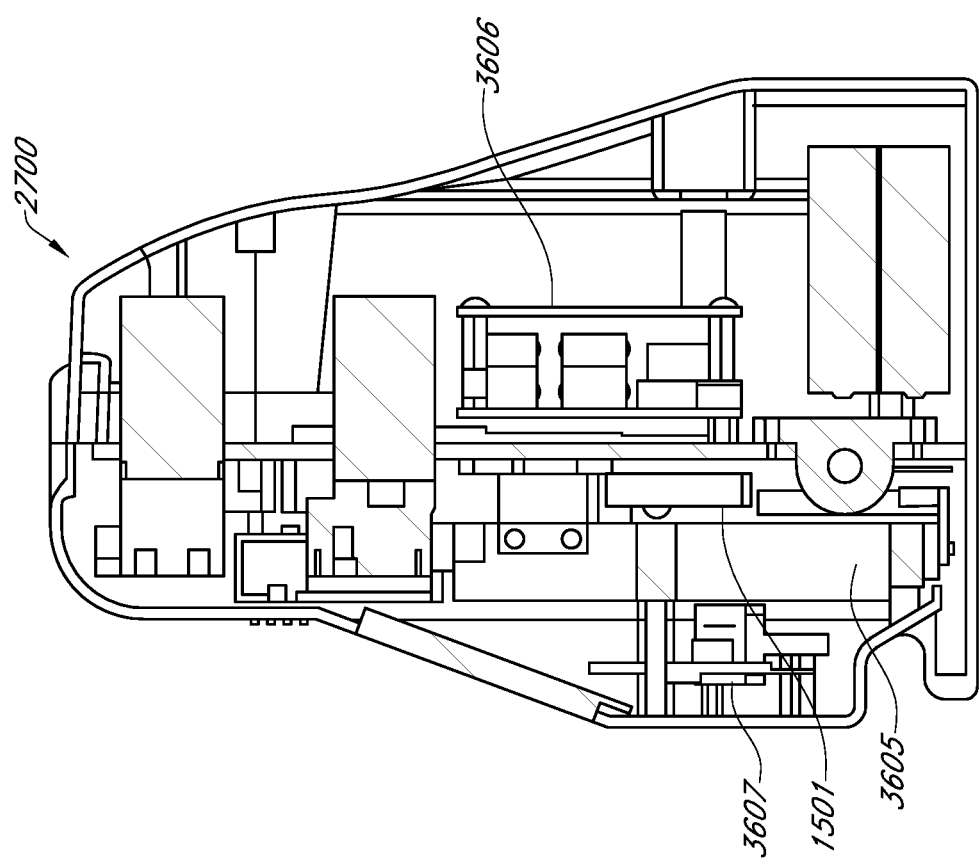
Figure 31B:
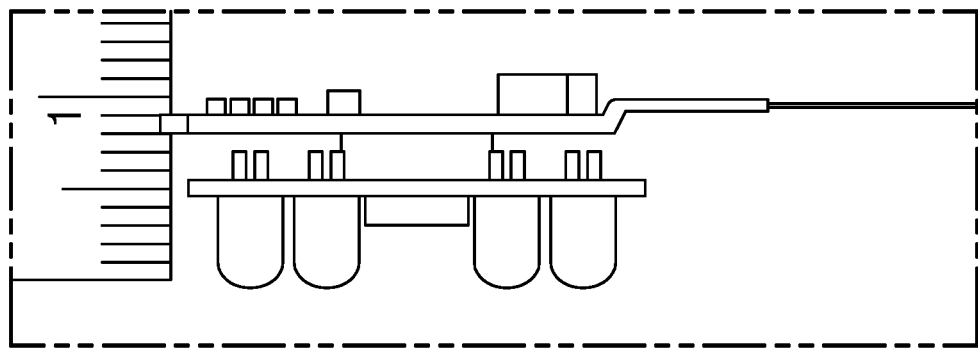
FIGS. 31A and 31B are front and side view photographs of an optical subsystem for an embodiment of the docking unit that incorporates a test reader.
Figure 31A:
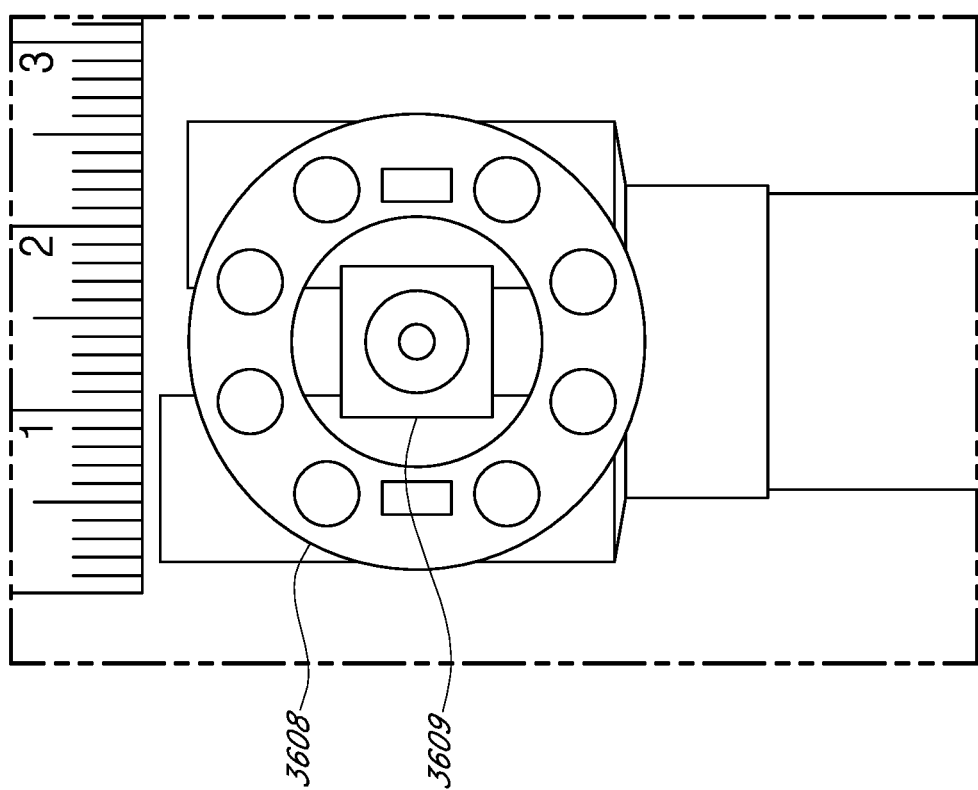

In another embodiment, the docking unit comprises servo actuators, an optical subsystem for automated result readout, a wireless data communication subsystem, a touch screen user interface, a rechargeable battery power source, and a test cassette receiver which accepts a test cassette comprising an integrated sample preparation subsystem. Referring now to FIGS. 29A, 29B, and 30, docking unit 2700 accepts test cassette 1500 and places the test cassette in thermal contact with PCA 1501 to enable temperature control and fluid flow control of the test cassette. Test cassette 1500 is inserted into cassette receiver slot 3605 of pivoting docking unit door 2702. Following the addition of crude sample or lysate to the test cassette, closure of docking unit door places the rear of the test cassette in register and in contact with PCA 1501 and in alignment with servo actuators. Servo actuator 3602 is situated to access solution compartmentalization component 1303 through actuator port 1310 of cassette 1500 and provide mechanical force required to rupture sealing material 1305. Rupture of mechanical seal 1305 releases crude lysate and wash buffers to flow through the sample preparation capillary materials of the sample preparation subsystem as described above. Following completion of capillary fluid transport, servo actuator 3601 which is situated to access elution reservoir 1317 through actuator port 1320 of cassette 1500 provides mechanical force to move component 1317 such that attached conduit 1318 forms a seal with seal 1316 and displaces binding matrix 1306 into elution compartment 1321. Servo actuator 3604 situated to access elution plunger 1319 through actuator port 1322 of cassette 1500 then provides mechanical force to plunger 1319 to expel elution buffer from elution reservoir 1317 though binding matrix 1306, resulting in the elution of nucleic acids into sample cup 1402 of cassette 1500. Servo actuator 3603 seals the cassette after elution as described above. Actuator control is preferably provided by a microcontroller or microprocessor on control electronics PCA 3606 according firmware or software instructions. Similarly, temperature and fluid flow control within the test cassette is according to instructions provided in firmware or software routines stored in microcontroller or microprocessor memory. Optical subsystem 3607 comprising LED light source 3608 and CMOS sensor 3609, shown in FIG. 31, digitizes detection strip signal data. Collected detection strip images are stored into memory within the docking unit where result interpretation can be accomplished using an on-board processor and reported to LCD display 2701. A ring of LEDs provides uniform illumination during image collection with a CMOS-based digital camera. Images collected with the postage stamp-sized device can provide high-resolution data (5 megapixels, bit) suitable for colorimetric lateral flow signal analysis. A preferably low profile design (~1 cm) together with short working distance optics enables the system to be integrated into a thin device housing.

Figure 32A:
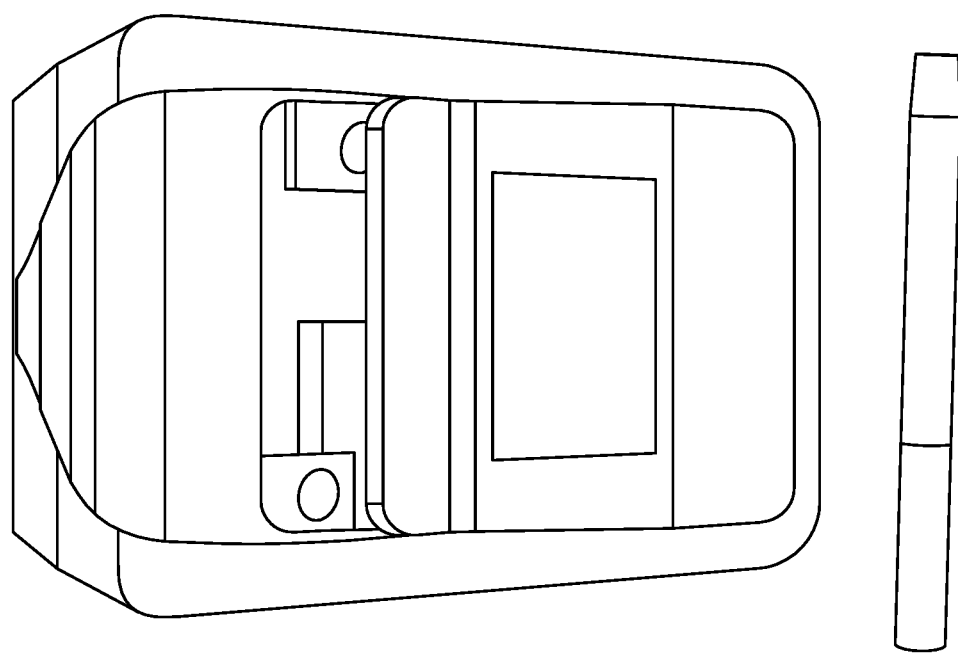
FIGS. 32A and 32B are photographs of a docking unit embodiment with a pivoting test cassette receiving door in the open position and closed position, respectively.
Figure 32B:
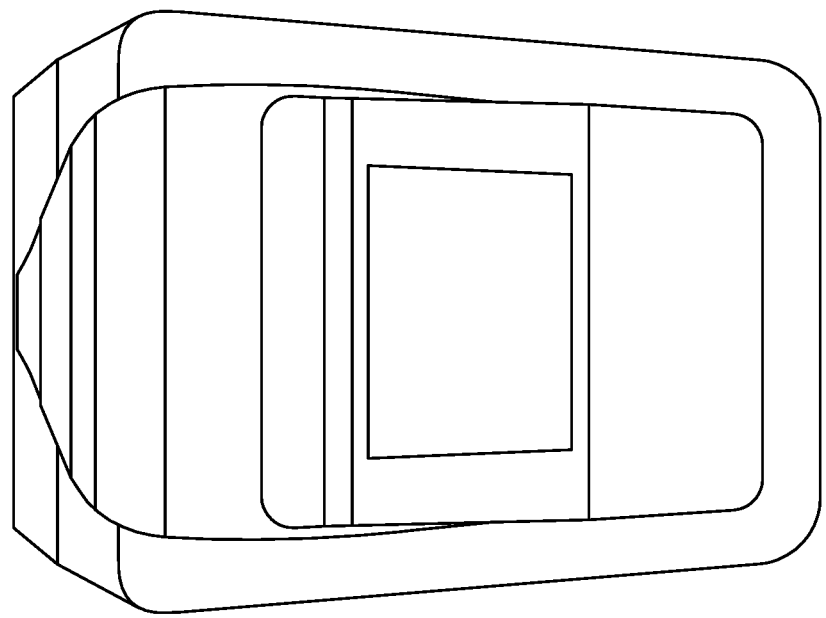

Optionally, digitized results may be transmitted for off-line analysis, storage and/or visualization via a wireless communication system incorporated into the docking unit employing either standard WiFi or cellular communications networks. Photographs of this docking unit embodiment are shown in FIGS. 32A and 32B.

EXAMPLES

Example 1: Method of Multiplexed Amplification and Detection of Purified Viral RNA (infA/B) and an Internal Positive Control Virus An influenza A and B test cassette was placed into the docking unit. 40 µL of a sample solution was added to the sample port. Sample solutions comprised either purified A/Puerto Rico influenza RNA at a concentration equivalent to 5000 $TCID_{50}$/mL, purified B/Brisbane influenza RNA at a concentration equivalent to 500 $TCID_{50}$/mL or molecular grade water (no template control sample). Upon entering the sample port, the 40 µL sample comingles with a lyophilized bead as it flows to a first chamber of the test cassette. The lyophilized bead was comprised of MS2 phage viral particles as a positive internal control and DTT. In the first chamber of the cassette the sample was heated to 90° C. for 1 minute to promote viral lysis then cooled to 50° C. prior to opening the vent connected a second chamber. Opening the vent connected to the second chamber allows the sample to flow into the second chamber by enabling the displacement of the air in the second chamber to an expansion chamber. As the sample moved to the second chamber it coming led with oligonucleotide amplification primers to influenza A, influenza B and MS2 phage, and reverse transcription and nucleic acid amplification reagents and enzymes present as a lyophilized pellet in a recess of the fluid path between first and second chambers.

Figure 34:
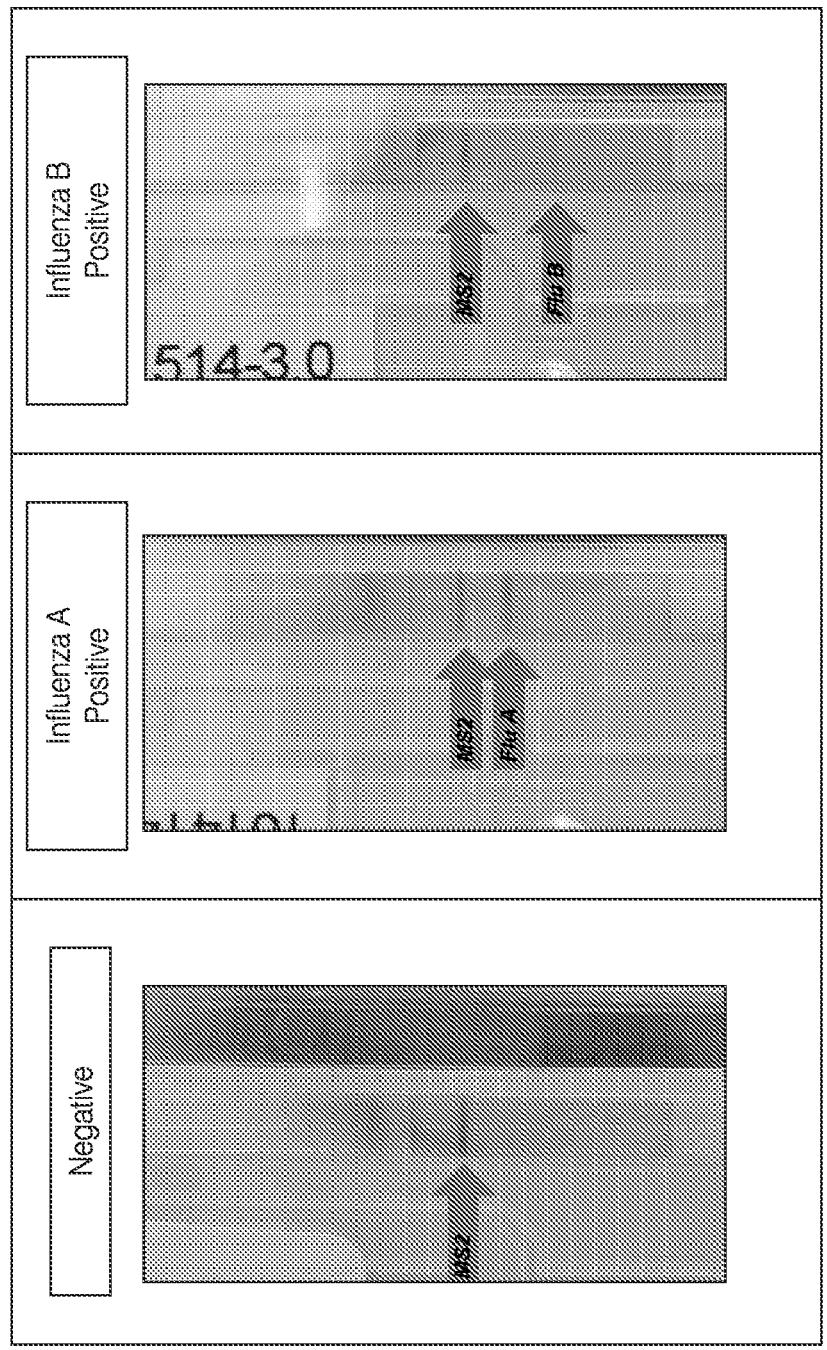
FIG. 34 shows test results obtained in Example 1 described herein.

The amplification chamber was heated to 47° C. for 6 minutes, during which time RNA template was reverse transcribed into cDNA. After completion of reverse transcription, 40 cycles of thermal cycle amplification was conducted in the second chamber. After thermal cycling was complete, a vent connected to a third chamber was opened to allow the reaction solution to flow into the third chamber. The third chamber comprised a test strip and a lyophilized bead comprising three blue-dyed polystyrene microsphere conjugates employed as detection particles. Conjugates were comprised of 300 nm polystyrene microspheres covalently linked to oligonucleotide probes complementary to amplified sequences of influenza A, or influenza B or MS2 phage. The solution reconstituted the lyophilized detection particles as it flowed into the third chamber. Three capture lines were immobilized on the lateral flow membrane, from the bottom of the device they were: A negative control oligonucleotide not complementary to any assayed targets; a capture probe complementary to the amplification product of influenza B; a capture probe complementary to the amplification product of influenza A; and a oligonucleotide complementary to the amplification product of MS2 phage. The lateral flow strip was allowed to develop for six minutes prior to visual interpretation of the results. Upon development of the lateral flow strip, influenza A positive samples displayed the formation of blue test lines at the influenza A and MS2 phage positions, influenza B positive samples displayed the formation of blue test lines at the influenza B and MS2 phage positions, negative samples displayed the formation of blue test lines only at the MS2 phage position as shown in FIG. 34.

Example 2: Method of Multiplexed Amplification and Detection of Viral Lysate in Buffer and an Internal Positive Control Virus An influenza A and B test cassette was placed into the docking unit. 40 µL of a sample solution was added to the sample port. Sample solutions comprised either A/Puerto Rico influenza virus at a concentration equivalent to 5000 TCID$_{50}$/mL, B/Brisbane influenza virus at a concentration equivalent to 500 TCID$_{50}$/mL or molecular grade water (no template control sample). Upon entering the sample port, the 40 µL sample comingles with a lyophilized bead as it flows to a first chamber of the test cassette. The lyophilized bead was comprised of MS2 phage viral particles as a positive internal control and DTT. In the first chamber of the cassette the sample was heated to 90° C. for 1 minute to promote viral lysis then cooled to 50° C. prior to opening the vent connected a second chamber. Opening the vent connected to the second chamber allows the sample to flow into the second chamber by enabling the displacement of the air in the second chamber to an expansion chamber. As the sample moved to the second chamber it coming led with oligonucleotide amplification primers to influenza A, influenza B and MS2 phage, and reverse transcription and nucleic acid amplification reagents and enzymes present as a lyophilized pellet in a recess of the fluid path between first and second chambers.

Figure 35:
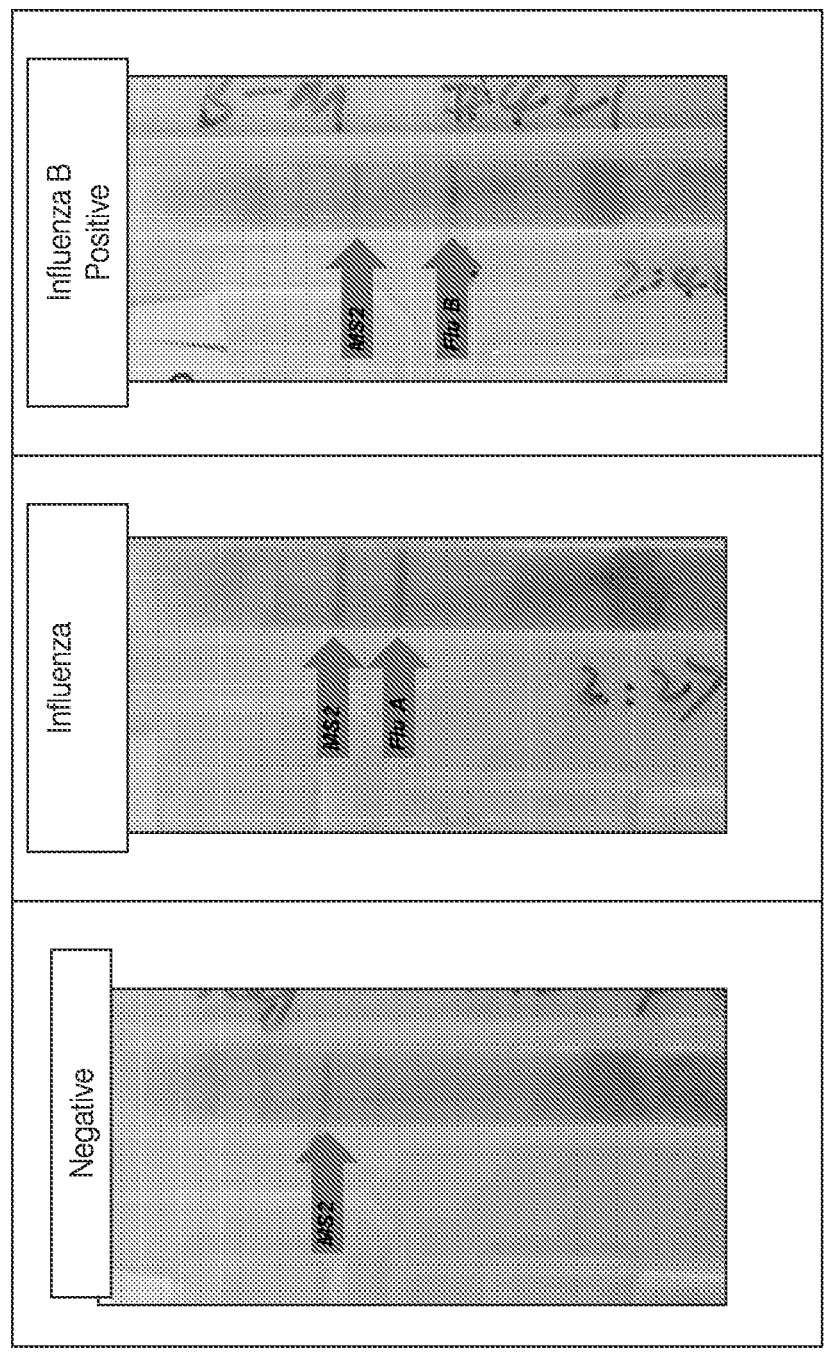
FIG. 35 shows test results obtained in Example 2 described herein.

The amplification chamber was heated to 47° C. for 6 minutes, during which time RNA template was reverse transcribed into cDNA. After completion of reverse transcription, 40 cycles of thermal cycle amplification was conducted in the second chamber. After thermal cycling was complete, a vent connected to a third chamber was opened to allow the reaction solution to flow into the third chamber. The third chamber comprised a test strip and a lyophilized bead comprising three blue-dyed polystyrene microsphere conjugates employed as detection particles. Conjugates were comprised of 300 nm polystyrene microspheres covalently linked to oligonucleotide probes complementary to amplified sequences of influenza A, or influenza B or MS2 phage. The solution reconstituted the lyophilized detection particles as it flowed into the third chamber. Three capture lines were immobilized on the lateral flow membrane, from the bottom of the device they were: A negative control oligonucleotide not complementary to any assayed targets; a capture probe complementary to the amplification product of influenza B; a capture probe complementary to the amplification product of influenza A; and a oligonucleotide complementary to the amplification product of MS2 phage. The lateral flow strip was allowed to develop for six minutes prior to visual interpretation of the results. Upon development of the lateral flow strip, influenza A positive samples displayed the formation of blue test lines at the influenza A and MS2 phage positions, influenza B positive samples displayed the formation of blue test lines at the influenza B and MS2 phage positions, negative samples displayed the formation of blue test lines only at the MS2 phage position as shown in FIG. 35.

Example 3: Method of Multiplexed Amplification and Detection of Influenza Virus (Purified) Spiked into Negative Clinical Nasal Samples and an Internal Positive Control Virus Nasal swab samples collected from human subjects were placed into 3 mL of a 0.025% Triton X-100, 10 mM Tris, pH 8.3 solution and tested for the presence of influenza A and influenza B using an FDA approved real-time RT-PCR test. Samples were confirmed to be negative for influenza A and influenza B prior to use in this study. Confirmed influenza negative nasal sample was spiked with A/Puerto Rico influenza virus at a concentration equivalent to 5000 TCID$_{50}$/mL or employed without the addition of virus as a negative control. 40 µL of the resulting spiked or negative control samples were added to the sample port of a influenza A and B test cassette. Upon entering the sample port, the 40 µL sample comingles with a lyophilized bead as it flows to a first chamber of the test cassette. The lyophilized bead was comprised of MS2 phage viral particles as a positive internal control and DTT. In the first chamber of the cassette the sample was heated to 90° C. for 1 minute to promote viral lysis then cooled to 50° C. prior to opening the vent connected a second chamber. Opening the vent connected to the second chamber allows the sample to flow into the second chamber by enabling the displacement of the air in the second chamber to an expansion chamber. As the sample moved to the second chamber it comingled with oligonucleotide amplification primers to influenza A, influenza B and MS2 phage, and reverse transcription and nucleic acid amplification reagents and enzymes present as a lyophilized pellet in a recess of the fluid path between first and second chambers.

Figure 36:
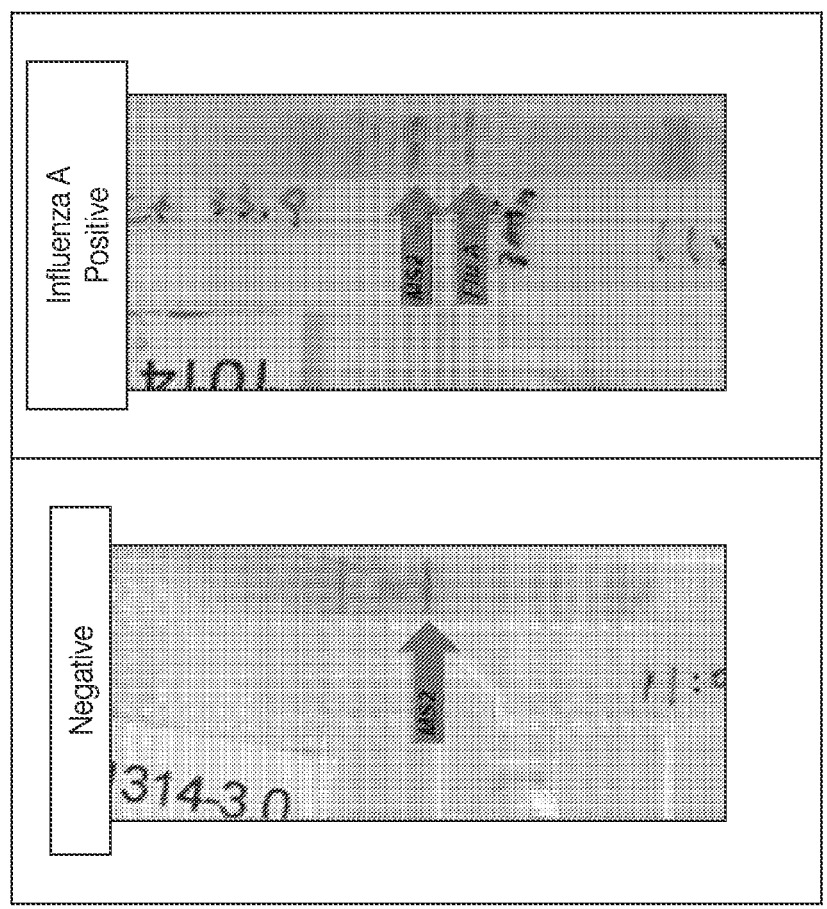
FIG. 36 shows test results obtained in Example 3 described herein.

The amplification chamber was heated to 47° C. for 6 minutes, during which time RNA template was reverse transcribed into cDNA. After completion of reverse transcription, 40 cycles of thermal cycle amplification was conducted in the second chamber. After thermal cycling was complete, a vent connected to a third chamber was opened to allow the reaction solution to flow into the third chamber. The third chamber comprised a test strip and a lyophilized bead comprising three blue-dyed polystyrene microsphere conjugates employed as detection particles. Conjugates were comprised of 300 nm polystyrene microspheres covalently linked to oligonucleotide probes complementary to amplified sequences of influenza A, or influenza B or MS2 phage. The solution reconstituted the lyophilized detection particles as it flowed into the third chamber. Three capture lines were immobilized on the lateral flow membrane, from the bottom of the device they were: A negative control oligonucleotide not complementary to any assayed targets; a capture probe complementary to the amplification product of influenza B; a capture probe complementary to the amplification product of influenza A; and a oligonucleotide complementary to the amplification product of MS2 phage. The lateral flow strip was allowed to develop for six minutes prior to visual interpretation of the results. Upon development of the lateral flow strip, influenza A positive samples displayed the formation of blue test lines at the influenza A and MS2 phage positions, negative control samples displayed the formation of blue test lines only at the MS2 phage position as shown in FIG. 36.

Although the invention has been described in detail with particular reference to the disclosed embodiments, other embodiments can achieve the same results. Variations and modifications of the present invention will be obvious to those skilled in the art and it is intended to cover all such modifications and equivalents. The entire disclosures of all patents and publications cited above are hereby incorporated by reference.

What is claimed is:

1. An automated method of performing an assay in a microfluidic device, comprising:
   introducing a sample into the microfluidic device by flowing the sample from a sample cup to a first chamber;
   opening a first vent to displace air in a second chamber to an expansion chamber, thereby mixing the sample with a reagent pellet comprising amplification reagents by flowing the sample through the reagent pellet in a reagent recess to the second chamber; and
   performing an amplification reaction in the second chamber directed towards a target sequence of the sample to provide an amplification product.

2. The method of claim 1, wherein performing the amplification reaction comprises performing a multiplex amplification reaction.

3. The method of claim 2, wherein the target sequence includes a target sequence for each of influenza A, influenza B, and a control.

4. The method of claim 3, wherein performing the assay comprises performing the assay in a hermetically sealed microfluidic device.

5. The method of claim 3, wherein the target sequence for the control further comprises a target sequence for a positive internal control.

6. The method of claim 5, wherein the target sequence further comprises a target sequence for MS2 phase viral particles.

7. The method of claim 3, wherein performing the amplification reaction comprises:
   heating the second chamber to 47° C. for 6 minutes for performing reverse transcription to transcribe each RNA target sequence to a cDNA target sequence; and
   amplifying cDNA target sequences formed during reverse transcription to provide the amplification product.

8. The method of claim 1, further comprising performing thermocycling on the second chamber using a resistive heating element.

9. The method of claim 3, wherein after performing the amplification reaction, the method further comprises:
   opening a second vent to displace air in a detection chamber to the expansion chamber, thereby allowing the amplification product to flow from the second chamber to a capillary pool proximal to a sample-receiving end of a lateral flow strip in the detection chamber;
   mixing the amplification product in the capillary pool with a second reagent pellet comprising detection particles, thereby labeling each set of target amplicons in the amplification product with a detection label; and
   detecting each target sequence in response to binding of detection-labeled target amplicons to a target-specific capture zone on the lateral flow strip.

10. The method of claim 9, wherein detecting each target sequence comprises:
    detecting influenza A or influenza B or a combination thereof in response to binding of labeled influenza A amplicons and labeled influenza B amplicons to an influenza A target zone and an influenza B target zone, respectively.

11. The method of claim 10, wherein performing the assay comprises performing the assay in a hermetically sealed microfluidic device.

12. The method of claim 10, wherein detecting each target sequence further comprises:
    detecting the control in response to binding of labeled control amplicons to a control zone.

13. The method of claim 12, wherein the control is a positive internal control.

14. The method of claim 13, wherein the positive internal control is comprised of MS2 phage viral particles.

15. The method of claim 9, wherein the opening the first vent and opening the second vent comprises rupturing a membrane.

16. The method of claim 15, wherein rupturing the membrane comprises heating a heat labile membrane.

17. The method of claim 16, wherein the heating the heat labile membrane comprises using a resistive heating element.

18. The method of claim 15, wherein the rupturing the membrane comprises puncturing, tearing, or dissolving the membrane.

19. The method of claim 9, wherein before opening the first vent, while the sample is in the first chamber, the method further comprises:
    heating the sample in the first chamber to 90° C. for 1 minute to effect lysis; and
    cooling the first chamber to 50° C. prior to opening the second vent.

* * * * *